United States Patent
Hinman et al.

(10) Patent No.: US 9,296,712 B2
(45) Date of Patent: Mar. 29, 2016

(54) RESORUFIN DERIVATIVES FOR TREATMENT OF OXIDATIVE STRESS DISORDERS

(71) Applicant: Edison Pharmaceuticals, Inc., Mountain View, CA (US)

(72) Inventors: Andrew W. Hinman, San Francisco, CA (US); Dana Davis, Sunnyvale, CA (US); William D. Shrader, Belmont, CA (US)

(73) Assignee: Edison Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 13/837,872

(22) Filed: Mar. 15, 2013

(65) Prior Publication Data

US 2014/0275054 A1    Sep. 18, 2014

(51) Int. Cl.
| | |
|---|---|
| C07D 265/38 | (2006.01) |
| A61K 31/536 | (2006.01) |
| C07D 413/10 | (2006.01) |

(52) U.S. Cl.
CPC ............ C07D 265/38 (2013.01); C07D 413/10 (2013.01)

(58) Field of Classification Search
CPC ...................................................... C07D 265/38
USPC ...................................... 544/102; 514/229.8
See application file for complete search history.

(56) References Cited

U.S. PATENT DOCUMENTS

| | | | |
|---|---|---|---|
| 4,667,032 A | 5/1987 | Lau et al. | |
| 4,859,667 A | 8/1989 | Lau et al. | |
| 4,939,145 A | 7/1990 | Lau et al. | |
| 5,035,998 A | 7/1991 | Von der Eltz et al. | |
| 5,801,159 A | 9/1998 | Miller et al. | |
| 5,874,461 A | 2/1999 | De Chaffoy de Courcelles et al. | |
| 6,232,060 B1 | 5/2001 | Miller et al. | |
| 6,426,362 B1 | 7/2002 | Miller et al. | |
| 6,528,042 B1 | 3/2003 | Brown et al. | |
| 6,608,196 B2 | 8/2003 | Wang et al. | |
| 6,653,346 B1 | 11/2003 | Wang et al. | |
| 7,034,054 B2 | 4/2006 | Miller et al. | |
| 7,078,541 B2 | 7/2006 | Boddupalli et al. | |
| 7,119,117 B2 | 10/2006 | Beinlich et al. | |
| 7,179,928 B2 | 2/2007 | Smith et al. | |
| 7,393,662 B2 | 7/2008 | Heavner et al. | |
| 7,432,305 B2 | 10/2008 | Miller et al. | |
| 7,470,798 B2 | 12/2008 | Wang et al. | |
| 7,491,312 B2 | 2/2009 | Gilat et al. | |
| 7,514,461 B2 | 4/2009 | Wang et al. | |
| 7,718,176 B2 | 5/2010 | Heavner et al. | |
| 7,875,607 B2 | 1/2011 | Wang et al. | |
| 7,968,746 B2 | 6/2011 | Jankowski et al. | |
| 8,044,097 B2 | 10/2011 | Wang et al. | |
| 8,106,223 B2 | 1/2012 | Wesson et al. | |
| 8,314,153 B2 | 11/2012 | Miller et al. | |
| 8,519,001 B2 | 8/2013 | Jankowski et al. | |
| 8,575,369 B2 | 11/2013 | Wesson et al. | |
| 8,653,144 B2 | 2/2014 | Miller et al. | |
| 8,716,486 B2 | 5/2014 | Hinman et al. | |
| 8,716,527 B2 | 5/2014 | Hinman et al. | |
| 2002/0132845 A1 | 9/2002 | Miller et al. | |
| 2003/0022818 A1 | 1/2003 | Miller et al. | |
| 2003/0144219 A1 | 7/2003 | Phinney et al. | |
| 2005/0065099 A1 | 3/2005 | Walkinshaw et al. | |
| 2005/0067303 A1 | 3/2005 | Wong et al. | |
| 2006/0281809 A1 | 12/2006 | Miller et al. | |
| 2007/0225261 A1 | 9/2007 | Miller et al. | |
| 2009/0162890 A1 | 6/2009 | Gilat et al. | |
| 2009/0163529 A1 | 6/2009 | Gilat et al. | |
| 2009/0291092 A1 | 11/2009 | Miller et al. | |
| 2010/0010100 A1 | 1/2010 | Hinman et al. | |
| 2010/0029784 A1 | 2/2010 | Hinman et al. | |
| 2010/0056429 A1 | 3/2010 | Miller et al. | |
| 2010/0222436 A1 | 9/2010 | Miller et al. | |
| 2010/0249032 A1 | 9/2010 | Heavner et al. | |
| 2010/0266591 A1 | 10/2010 | Bugelski et al. | |
| 2010/0273892 A1 | 10/2010 | Miller et al. | |
| 2010/0273894 A1 | 10/2010 | Miller | |
| 2011/0046156 A1 | 2/2011 | Miller | |
| 2011/0046219 A1 | 2/2011 | Hinman et al. | |
| 2011/0142834 A1 | 6/2011 | Miller | |
| 2011/0172312 A1 | 7/2011 | Miller et al. | |
| 2011/0207828 A1 | 8/2011 | Miller et al. | |
| 2011/0269776 A1 | 11/2011 | Miller | |
| 2012/0088783 A1 | 4/2012 | Wang et al. | |
| 2012/0101169 A1 | 4/2012 | Hawi | |
| 2012/0122969 A1 | 5/2012 | Miller | |

(Continued)

FOREIGN PATENT DOCUMENTS

| | | |
|---|---|---|
| EP | 1 15394 A2 | 8/1984 |
| EP | 1 38481 A2 | 4/1985 |

(Continued)

OTHER PUBLICATIONS

Zaytsev et al. Organic & Biomolecular Chemistry (2008), 6(4), 682-692.*
Barbiroli, B. et al. (1995). "Lipoic (Thioctic) Acid Increases Brain Energy Availability and Skeletal Muscle Performance as Shown by In Vivo $^{31}$P-MRS in a Patient with Mitochondrial Cytopathy," *J. Neurol.* 242(7):472-477.
Bird, C.W. et al. (1980). "A New Synthesis of 3*H*-Phenoxazin-3-Ones," *Tetrahedron* 36(4):529-533 (XP055121040, DOI: 10.1016/0040-4020(80)80030-5).

(Continued)

*Primary Examiner* — Kahsay Habte

(74) *Attorney, Agent, or Firm* — Squire Patton Boggs (US) LLP

(57) ABSTRACT

Disclosed herein are resorufin derivative compounds and methods of using such compounds for treating or suppressing oxidative stress disorders, including mitochondrial disorders, impaired energy processing disorders, neurodegenerative diseases and diseases of aging.

19 Claims, No Drawings

(56) References Cited

U.S. PATENT DOCUMENTS

| | | |
|---|---|---|
| 2012/0136048 A1 | 5/2012 | Miller et al. |
| 2012/0295985 A1 | 11/2012 | Miller et al. |
| 2013/0109759 A1 | 5/2013 | Miller |
| 2013/0116336 A1 | 5/2013 | Shrader |
| 2013/0267538 A1 | 10/2013 | Walkinshaw et al. |
| 2013/0289034 A1 | 10/2013 | Jankowski et al. |
| 2013/0345312 A1 | 12/2013 | Jankowski et al. |
| 2014/0031432 A1 | 1/2014 | Jankowski et al. |
| 2014/0031433 A1 | 1/2014 | Miller et al. |
| 2014/0039065 A1 | 2/2014 | Miller |

FOREIGN PATENT DOCUMENTS

| | | |
|---|---|---|
| EP | 1 55623 A2 | 9/1985 |
| JP | 59-144774 A | 8/1984 |
| WO | WO-84/04679 A1 | 12/1984 |
| WO | WO-00/78296 A2 | 12/2000 |
| WO | WO-00/78296 A3 | 12/2000 |
| WO | WO-02/47680 A2 | 6/2002 |
| WO | WO-02/47680 A3 | 6/2002 |
| WO | WO-02/47680 A9 | 6/2002 |
| WO | WO-03/064403 A1 | 8/2003 |
| WO | WO-03/066618 A1 | 8/2003 |
| WO | WO-2004/003565 A2 | 1/2004 |
| WO | WO-2004/003565 A3 | 1/2004 |
| WO | WO-2004/087160 A1 | 10/2004 |
| WO | WO-2010/014758 A1 | 2/2010 |
| WO | WO-2011/041452 A2 | 4/2011 |
| WO | WO-2011/113018 A1 | 9/2011 |
| WO | WO-2012/019029 A2 | 2/2012 |
| WO | WO-2012/019029 A3 | 2/2012 |
| WO | WO-2012/019032 A1 | 2/2012 |
| WO | WO-2012/138713 A2 | 10/2012 |
| WO | WO-2012/138713 A3 | 10/2012 |
| WO | WO-2012/149478 A2 | 11/2012 |
| WO | WO-2012/149478 A3 | 11/2012 |
| WO | WO-2012/154613 A1 | 11/2012 |
| WO | WO-2012/170773 A1 | 12/2012 |
| WO | WO-2012/174286 A1 | 12/2012 |
| WO | WO-2013/006736 A1 | 1/2013 |
| WO | WO-2013/006737 A1 | 1/2013 |
| WO | WO-2013/013078 A1 | 1/2013 |
| WO | WO-2014/039862 A1 | 3/2014 |
| WO | WO-2014/039917 A1 | 3/2014 |

OTHER PUBLICATIONS

Brockmann, H. et al. (Apr. 1, 1958). "Actinomycine, XVIII. Antibiotica aus Actinomyceten, XXXIX. Abbau von Actinomycin C zu Actinocinin and Desamino-actinocinyl-threonin," *Chemische Berichte* 91(4):773-781. (Translation of Chemical Abstract only: Caplus Abstract No. 1960:2249.).

Cadenas, E. et al. (2000). "Mitochondrial Free Radical Generation, Oxidative Stress and Aging," *Free Radical Biology & Medicine* 29(3/4):222-230.

Cavill, G.W.K. et al. (1961). "The Chemistry of Mould Metabolites—IV. Reductive Acetylation and Reoxidation of Some Phenoxazin-3-ones," *Tetrahedron* 12:139-145.

Chariot, P. et al. (Apr. 1994). "Determination of the Blood Lactate:Pyruvate Ratio As a Noninvasive Test for the Diagnosis of Zidovudine Myopathy," *Arthritis & Rheumatism* 37(4):583-586.

Chariot, P. et al. (Jul. 1994). "Optimal Handling of Blood Samples for Routine Measurement of Lactate and Pyruvate," *Arch. Pathol. Lab. Med.* 118(7):695-697.

Corbett, J.F. (1965). "The Spectra of Polycyclic Oxazines and Azines—III. The Infrared Spectra of Phenoxazinones," *Spectrochimica Acta* 21:1411-1417.

Crescenzi, O. et al. (2004). "Observed and Calculated $^1$H- and $^{13}$C-NMR Chemical Shifts of Substituted 5H-pyrido[3,2-a]- and 5H-pyrido[2,3-a]phenoxazin-5-ones and of Some 3H-phenoxazin-3-one Derivatives," *Org. Biomol. Chem.* 2:1577-1581.

Descalzo, A.B. et al. (2003, e-pub. Feb. 27, 2003). "Coupling Selectivity with Sensitivity in an Integrated Chemosensor Framework: Design of a Hg$^{2+}$Responsive Probe, Operating Above 500 nm," *J. Am. Chem. Soc.* 125:3418-3419.

Deschauer, M. et al. (2005). "A Novel *ANT1* Gene Mutation with Probable Germline Mosaicism in Autosomal Dominant Progressive External Ophthalmoplegia," *Neuromuscular Disorders* 15:311-315.

Dimauro, S. (1999). "Exercise Intolerance and the Mitochondrial Respiratory Chain," *Ital. J. Neurol. Sci.* 20:387-393.

Erhola, M. et al. (1997). "Biomarker Evidence of DNA Oxidation in Lung Cancer Patients: Association of Urinary 8-Hydroxy-2'-Deoxyguanosine Excretion with Radiotherapy, Chemotherapy, and Response to Treatment," *FEBS Letters* 409(2):287-291.

Fabrizi, G.M. et al. (1996). "Autosomal Dominant Limb Girdle Myopathy with Ragged-Red Fibers and Cardiomyopathy. A Pedigree Study by In Vivo $^{31}$P-MR Spectroscopy Indicating a Multisystem Mitochondrial Defect," *Journal of the Neurological Sciences* 137(1)20-27.

Gempel, K. et al. (2007). "The Myopathic Form of Coenzyme Q10 Deficiency is Caused by Mutations in the Electron-Transferring-Flavoprotein Dehydrogenase (*ETFDH*) Gene," *Brain* 130(8):2037-2044.

Harman, D. (Jul. 1956), "Aging—A Theory Based on Free-Radical and Radiation Chemistry," *J. Gerontol.* 11(3):298-300.

Hasegawa, K-I. et al. (1985). "The Carbon-13 NMR Spectra and Electronic Structure of 3H-Phenoxazin-3-ones," *Bulletin of the Chemical Society of Japan* 58(10):2832-2839.

Haynes, R.K. et al, (1972). "Amine Oxidation and the Chemistry of Quinone Imines. Part II. 2,5-Di-methoxy-4-t-butylanHine," *Journal of the Chemical Society, Perkin Transactions 1.* pp. 408-413 (XP055120706, DOI: 10.1039/P19720000408).

Honda, M. et al. (2000). "Correlation of Urinary 8-Hydroxy-2'-Deoxyguanosine (8-OHdG), a Biomarker of Oxidative DNA Damage, and Clinical Features of Hematological Disorders: A Pilot Study," *Leukemia Research* 24(6):461-468.

Jauslin, M.L. et al. (2002). "A Cellular Model for Friedreich Ataxia Reveals Small-Molecule Glutathione Peroxidase Mimetics as Novel Treatment Strategy," *Human Molecular Genetics* 11(24):3055-3063.

Jauslin, M.L. et al. (Oct. 2003, e-pub. Aug. 15, 2003). "Mitochondria-Targeted Antioxidants Protect Friedreich Ataxia Fibroblasts from Endogenous Oxidative Stress More Effectively Than Untargeted Antioxidants" *The FASEB Journal* 17(13):1972-1974.

Jones, D.P. et al (Nov. 15, 2009). "Measuring the Poise of Thiol/Disulfide Couples in vivo," *Free Radical Biology & Medicine* 47(10):1329-1338, twenty-four pages.

Kaufmann, P. et al. (Apr. 27, 2004). "Cerebral Lactic Acidosis Correlates with Neurological Impairment in MELAS," *Neurology* 62(8):1297-1302.

Kehrmann, F. (Jan. 1, 1902). "Ueber die Constitution der Oxazin und Thiazinfarbstoffe und ihre Beziehungen zu den Azoniumkorpern," *Justus Liebigs Annalen Der Chemie* 322(1):1-77. (Translation of Chemical Abstract only: Caplus Abstract No. 1906:222661.).

Kim, J.Y. et al. (May 2004). "Urinary 8-Hydroxy-2'-Deoxyguanosine as a Biomarker of Oxidative DNA Damage in Workers Exposed to Fine Particulates," *Environmental Health Perspectives* 112(6):666-671.

Kinjo, J. et al. (1987). "Structures of Phytotoxic Metabolites from the Fungus of Zonate Leaf Spot Disease on Mulberry," *Tennen Yuki Kagobutsu Toronkai Koen Yoshishu* 29:623-628. (p. 628 in English).

Kinjo, J-E. et al. (1987). "Structures of Phytotoxins, AV-Toxins C, D and E, Produced by Zonate Leaf Spot Fungus of Mulberry," *Tetrahedron Letters* 28(32):3697-3698.

Lamperti, C. et al. (2003), "Cerebellar Ataxia and Coenzyme Q10 Deficiency," *Neurology* 60:1206:1208.

Lee, P.I. (1992). "Diffusion-Controlled Matrix Systems," Chapter 3 in *Treatise on Controlled Dug Delivery*, Kydonieus, A. ed., Marcel Dekker, Inc., New York, NY, pp. 155-197.

Lynch, D.R. et al. (May 2002, e-pub. Feb. 25, 2002). "Near Infrared Muscle Spectroscopy in Patients with Friedreich's Ataxia," *Muscle Nerve* 25(5):664-673.

Matthews, P.M. et al. (Apr. 1991). "In Vivo Magnetic Resonance Spectroscopy of Brain and Muscle in a Type of Mitochondrial Encephalomyopathy (MERRF)," *Annals of Neurology* 29(4):435-438.

McClean, M.R. et al. (1990). "A. Photophysical and Structural Study on Dye-Type Organic Molecules with Potentially Useful Nonlinear Optical Properties," *J. Phys. Chem.* 94:4386-4387.

(56) References Cited

OTHER PUBLICATIONS

Munnich, A. et al. (1992). "Clinical Aspects of Mitochondrial Disorders," *Journal of Inherited Metabolic Disease* 15(4):448-455.
Musso, H. et al. (Sep. 1, 1957). "Uber Orceinfarbstoffe, V. IR- und UV-Spektren Hydroxy- und Amino-Substituierter Phenoxazone," *Chemische Berichte* 90(9):1814-1827. (Translation of Chemical Abstract only: Caplus Abstract No. 1959:53796.).
Musso, H. et al. (Mar. 1, 1961). "Uber Orceinfarbstoffe, XII: Synthesen des α-Oxy-orceins," *Chemische Berichte* 94(3):585-600. (Translation of Chemical Abstract only: Caplus Abstract No. 1961:76175.).
Musso, H. et al. (Dec. 1, 1962). "Uber Orceinfarbstoffe, XVI. Die Autoxydation von Resorcinderivaten, insbesondere des 4.5-Dimethyl-resorcins," *Chemische Berichte* 95(12):2831-2836. (Translation of Chemical Abstract only: Caplus Abstract No. 1963:53852.).
Musso, H. et al. (Jun. 1, 1963). "Uber Orceinfarbstoffe, XX. Die Autoxydationsprodukte des 2.5-Dimethyl-resorcins in Ammoniak und Kalilauge," *Chemische Berichte* 96(6):1593-1609. (Translation of Chemical Abstract only: Caplus Abstract No. 1963:436058.).
Musso, H. et al, (May 1, 1966). "Phenoxazine, IX. Synthese und Lichtabsorption von 8-Hydroxy-phenoxazonen-(3)," *Chemische Berichte* 99(5):1470-1478. (Translation of Chemical Abstract only: Caplus Abstract No. 1966:412290.).
Musumeci, O. et al. (2001). "Familial Cerebellar Ataxia with Muscle Coenzyme Q10 Deficiency," *Neurology* 56:849-855.
Nakazawa, H. et al. (1981). "Chemical Reduction of Actinomycin D and Phenoxazone Analogues to Free Radicals," *The Journal of Organic Chemistry* 46(7):1493-1496.
Pilger, A. et al. (2001). "Longitudinal Study of Urinary 8-Hydroxy-2'-Deoxyguanosine Excretion in Healthy Adults," *Free Radical Research* 35(3):273-280.
Piña, I.L. et al. (2003). "Exercise and Heart Failure: A Statement from the American Heart Association Committee on Exercise, Rehabilitation, and Prevention," *Circulation* 107:1210-1225.
Rolfe, P. (2000). "In Vivo Near-Infrared Spectroscopy," *Annual Review of Biomedical Engineering* 2:715-754.
Ron, E. et al. (1992). "Erodible Systems," Chapter 4 in *Treatise on Controlled Drug Delivery*, Kydonieus, A. ed., Marcel Dekker, Inc., New York, NY, pp. 199-224.
Ruzicka, E. et al. (1964). "Uber Ather des Resazurins." *Collection of Czechoslovak Chemical Communications* 29(9):2244-2249. (Translation of Chemical Abstract only: Caplus Abstract No. 1965:12079.).
Sridharan, V. et al. (2007). "One-Pot Synthesis of Symmetrically Disubstituted 3H-Phenoxazin-3-ones by Selective Oxidative Condensation with LTA," *J. Heterocyclic Chem.* 44:491-493.
Strangman, G. et al. (2002). "Non-Invasive Neuroimaging Using Near-Infrared Light," *Biol. Psychiatry* 52:679-693.
Taivassalo, T. et al. (Jan. 2002, e-pub. Nov. 15, 2001). "Venous Oxygen Levels During Aerobic Forearm Exercise: An Index of Impaired Oxidative Metabolism in Mitochondrial Myopathy," *Ann. Neurol.* 51(1):38-44.
Taivassalo, T. et al. (2003). "The Spectrum of Exercise Tolerance in Mitochondrial Myopathies: A Study of 40 Patients," *Brain* 126:413-423.
Ueda, K. et al. (Feb. 1997). "Evaluation of Changes in Hepatic Energy Metabolism During Exercise by Ketone Body Ratio in Humans," *J. Cardiol.* 29(2):95-102. (Translation of Abstract Only).
Ueno, Y. (1982). "The Alkylation of 3H-Phenoxazin-3-one Derivatives," *J. Heterocyclic Chem.* 19:1579-1580.
Valko, M. et al. (2004). "Role of Oxygen Radicals in DNA Damage and Cancer Incidence," *Molecular and Cellular Biochemistry* 266:37-56.
Van Beekvelt, M.C.P. et al. (Oct. 1999). "Quantitative Near-Infrared Spectroscopy Discriminates Between Mitochondrial Myopathies and Normal Muscle," *Annals of Neurology* 46(4):667-670.
Zaytsev, A.V. et al. (Feb. 21, 2008, e-pub. Jan. 4, 2008). "Synthesis and Testing of Chromogenic Phenoxazinone Substrates for β-alanyl Amynopeptidase," *Organic & Biomolecular Chemistry* 6(4):682-692.

International Search Report mailed on Jun. 16, 2014 for PCT Patent Application No. PCT/US2014/029809 filed on Mar. 14, 2014, 10 pages.
Written Opinion mailed on Jun. 16, 2014 for PCT Patent Application No. PCT/US2014/029809 filed on Mar. 14, 2014, 10 pages.
International Search Report mailed on Jul. 15, 2014 for PCT Patent Application No. PCT/US2014/029811 filed on Mar. 14, 2014, 3 pages.
Written Opinion mailed on Jul. 15, 2014 for PCT Patent Application No. PCT/US2014/029811 filed on Mar. 14, 2014, 5 pages.
Bird et al. "Further Studies on The Cyclisation of 3-Hydroxy-2'-Nitrodiphenyl Ethers and Related Compounds," Tetrahedron, 1980, vol. 36, pp. 1813-1816.
Burger et al. "Crystal structure of the predicted phospholipase LYPLAL1 reveals unexpected functional plasticity despite close relationship to acyl protein thioesterases," Journal of Lipid Research, 2012, vol. 53, pp. 43-50.
Cairns-Smith, "Tautomerism in the Solid State. Part I. Thermochromism of Heterocyclic Phenols." Journal of Chemical Society, 1961, vol. 182-188.
Corbett, "The infra-red and ultra-violet spectra of hydroxyphenazines," Spectrochimica Acts, 1964, vol. 20, pp. 1665-1678.
Hasegawa et al. "The Carbon-13 NMR Spectra and Electronic Structure of 3H-Phenothiazin-3-one and Its Methyl Derivatives," Bull. Chem. Soc. Jpn., 1984, vol. 57, No. 2, pp. 510-517.
Hasegawa et al."The Carbon-13 NMR Spectra and Electronic Structure of 3H-Phenoxazin-3-ones," Bull.. Chem. Soc. Jpn., 1985, 58, 2832-2839.
John, Angewandte Cehmie, 1947, vol. 59, No. 7-8, pp. 188-194.
John, W. Reichsamt Wirtschaftsausbau, Chem Ber. Pruf-Nr. (1942), 15(PB-52014), pp. 353-382. (Abstract only).
Kajimoto et al. "A Short Step Synthesis of AV-toxin D," Chemistry Letters, 1988, pp. 1113-1114.
Kinjo et al. "Structures of Phytotoxins, AV-Toxins C, D and E, Produced by Zonate Leaf Spot Fungus of Mulberry, " Tetrahedron Letters, 1987, vol. 28, No. 32, pp. 3697-3698.
Kinjo, Tennen Yuki Kagobutsu Toronkai Koen Yoshishu (1987), 29, 623-628 (p. 628 in English).
Mash et al. "Synthesis of 7-Alkoxyquinolines, Coumarins and Resorufins," Synthetic Communications, 2000, vol. 30, No. 2, pp. 367-375.
Perkampus et al. Zeitschrift fur Elektrochemie und Angewandte Physikalische Chemie, 1958, vol. 62, pp. 94-105.
Perkampus, Zeitschrift für Physikalische Chemie, 1954, vol. 2, pp. 290-311.
Perkampus, Zeitschrift für Physikalische Chemie, 1956, vol. 6, pp. 18-44.
CAS Registry No: 1356116-71-6 (Date entered in CAS Registry database: Feb. 9, 2012).
10H-phenothiazin-3-ol 5-oxide, CAS No: 38015-17-7 (Date entered in CAS Registry database: Nov. 16, 1984).
Ampliflu Red, CAS No: 119171-73-2 (Date entered in CAS Registry database: Feb. 17, 1989).
Methylene Violet (Bernthsen), CAS No: 2516-05-4 (Date entered in CAS Registry database: Nov. 16, 1984).
Phenothiazine, CAS No: 92-84-2 (Date entered in CAS Registry database: Nov. 16, 1984).
Phenothiazine-5-Oxide, CAS No: 1207-71-2 (Date entered in CAS Registry database: Nov. 16, 1984).
Phenoxazine, CAS No. 135-67-1 (Date entered in CAS Registry database: Nov. 16, 1984).
Resazurin sodium salt, CAS No: 62758-13-8 (Date entered in CAS Registry database: Nov. 16, 1984).
Resorufin acetate, CAS No: 1152-14-3 (Date entered in CAS Registry database: Nov. 16, 1984).
Resorufin benzyl ether, CAS No: 87687-02-3 (Date entered in CAS Registry database: Nov. 16, 1984).
Resorufin ethyl ether, CAS No. 5725-91-7 (Date entered in CAS Registry database: Nov. 16, 1984).
Resorufin methyl ether, CAS No: 5725-89-3 (Date entered in CAS Registry database: Nov. 16, 1984).

(56) References Cited

OTHER PUBLICATIONS

Resorufin pentyl ether, CAS No: 87687-03-4 (Date entered in CAS Registry database: Nov. 16, 1984).
Resorufin β-D-galactopyranoside, CAS No: 95079-19-9 (Date entered in CAS Registry database: Mar. 3, 1985).
Resorufin β-D-glucopyranoside, CAS No. 101490-85-1 (Date entered in CAS Registry database: Apr. 12, 1986).
Resorufin β-D-glucuronide sodium salt, CAS No: 125440-91-7 (Date entered in CAS Registry database: Feb. 16, 1990).
Resorufin, CAS No: 635-78-9 (Date entered in CAS Registry database: Nov. 16, 1984).
Suhrmann, Zeitschrift fur Elektrochemie und Angewandte Physikalische Chemie (1952) vol. 56, pp. 743-745.
Suhrmann, Zur Deutung der Solvatochromie, Naturwissenschaften, 1951, vol. 38, No. 16, pp. 382.
Ueno "The Polarographi Reduction of 3H-Phenothiazin-3-ones in Non-aqueous Media," Aromatikkusu 1986, vol. 38, pp. 299-304.
Ueno, Y. "Polarographic Investigation of 3H-Phenothiazin-3-ones," Pharmazie, 1985, vol. 40, No. 3, pp. 198199.
Ueno, Y. "Synthesis of Dimethyl- and Trimethyl-3H-phenothiazin-3-ones," Pharmazie, 1984, vol. 39, No. 5, pp. 355-356.
Ueno, Y. "The Alkylation of 3H-Phenoxazin-3-one Derivatives," J. Het. Chem., 1962, 19, 1579.
Zaytsev et la. "Synthesis and testing of chromogenic phenoxazinone substrates for β-alanyl aminopeptidase," Org. Biomol. Chem, 2008, vol. 6, pp. 682-692.
Bird et al. "A New Synthesis of 3H-Phenoxazin-3-ones," Tetrahedron 1980, 36(4), p. 529-533.
Corbett et al. "The Spectra of Polycyclic Oxazines and Azines—III. The Infrared Spectra of Phenoxazinones," Spectrochimica Acts, 1965, vol. 21, pp. 1411-1417.

\* cited by examiner

RESORUFIN DERIVATIVES FOR TREATMENT OF OXIDATIVE STRESS DISORDERS

TECHNICAL FIELD

The application discloses compositions and methods useful for treatment or suppression of diseases, developmental delays and symptoms related to oxidative stress disorders. Examples of such disorders include mitochondrial disorders, impaired energy processing disorders, neurodegenerative diseases and diseases of aging.

BACKGROUND

Oxidative stress is caused by disturbances to the normal redox state within cells. An imbalance between routine production and detoxification of reactive oxygen species such as peroxides and free radicals can result in oxidative damage to the cellular structure and machinery. The most important source of reactive oxygen species under normal conditions in aerobic organisms is probably the leakage of activated oxygen from mitochondria during normal oxidative respiration. Impairments associated with this process are suspected to contribute to mitochondrial disease, neurodegenerative disease, and diseases of aging.

Mitochondria are organelles in eukaryotic cells, popularly referred to as the "powerhouse" of the cell. One of their primary functions is oxidative phosphorylation. The molecule adenosine triphosphate (ATP) functions as an energy "currency" or energy carrier in the cell, and eukaryotic cells derive the majority of their ATP from biochemical processes carried out by mitochondria. These biochemical processes include the citric acid cycle (the tricarboxylic acid cycle, or Krebs cycle), which generates reduced nicotinamide adenine dinucleotide (NADH+H+) from oxidized nicotinamide adenine dinucleotide (NAD+), and oxidative phosphorylation, during which NADH+H+ is oxidized back to NAD+. (The citric acid cycle also reduces flavin adenine dinucleotide, or FAD, to FADH2; FADH2 also participates in oxidative phosphorylation.)

The electrons released by oxidation of NADH+H+ are shuttled down a series of protein complexes (Complex I, Complex II, Complex III, and Complex IV) known as the mitochondrial respiratory chain. These complexes are embedded in the inner membrane of the mitochondrion. Complex IV, at the end of the chain, transfers the electrons to oxygen, which is reduced to water. The energy released as these electrons traverse the complexes is used to generate a proton gradient across the inner membrane of the mitochondrion, which creates an electrochemical potential across the inner membrane. Another protein complex, Complex V (which is not directly associated with Complexes I, II, III and IV) uses the energy stored by the electrochemical gradient to convert ADP into ATP.

When cells in an organism are temporarily deprived of oxygen, anaerobic respiration is utilized until oxygen again becomes available or the cell dies. The pyruvate generated during glycolysis is converted to lactate during anaerobic respiration. The buildup of lactic acid is believed to be responsible for muscle fatigue during intense periods of activity, when oxygen cannot be supplied to the muscle cells. When oxygen again becomes available, the lactate is converted back into pyruvate for use in oxidative phosphorylation.

Oxygen poisoning or toxicity is caused by high concentrations of oxygen that may be damaging to the body and increase the formation of free-radicals and other structures such as nitric oxide, peroxynitrite, and trioxidane. Normally, the body has many defense systems against such damage but at higher concentrations of free oxygen, these systems are eventually overwhelmed with time, and the rate of damage to cell membranes exceeds the capacity of systems which control or repair it. Cell damage and cell death then results.

Qualitative and/or quantitative disruptions in the transport of oxygen to tissues result in energy disruption in the function of red cells and contribute to various diseases such as haemoglobinopathies. Haemoglobinopathy is a kind of genetic defect that results in abnormal structure of one of the globin chains of the hemoglobin molecule. Common haemoglobinopathies include thalassemia and sickle-cell disease. Thalassemia is an inherited autosomal recessive blood disease. In thalassemia, the genetic defect results in reduced rate of synthesis of one of the globin chains that make up hemoglobin. While thalassemia is a quantitative problem of too few globins synthesized, sickle-cell disease is a qualitative problem of synthesis of an incorrectly functioning globin. Sickle-cell disease is a blood disorder characterized by red blood cells that assume an abnormal, rigid, sickle shape. Sickling decreases the cells' flexibility and results in their restricted movement through blood vessels, depriving downstream tissues of oxygen.

Mitochondrial dysfunction contributes to various disease states. Some mitochondrial diseases are due to mutations or deletions in the mitochondrial genome. If a threshold proportion of mitochondria in the cell is defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved. Some examples of mitochondrial diseases are Friedreich's ataxia (FRDA), Leber's Hereditary Optic Neuropathy (LHON), mitochondrial myopathy, encephalopathy, lactacidosis, and stroke (MELAS), Myoclonus Epilepsy Associated with Ragged-Red Fibers (MERRF) syndrome, Leigh's disease, and respiratory chain disorders. Most mitochondrial diseases involve children who manifest the signs and symptoms of accelerated aging, including neurodegenerative diseases, stroke, blindness, hearing impairment, vision impairment, diabetes, and heart failure.

Friedreich's ataxia is an autosomal recessive neurodegenerative and cardiodegenerative disorder caused by decreased levels of the protein Frataxin. The disease causes the progressive loss of voluntary motor coordination (ataxia) and cardiac complications. Symptoms typically begin in childhood, and the disease progressively worsens as the patient grows older; patients eventually become wheelchair-bound due to motor disabilities.

Leber's Hereditary Optic Neuropathy (LHON) is a disease characterized by blindness which occurs on average between 27 and 34 years of age. Other symptoms may also occur, such as cardiac abnormalities and neurological complications.

Mitochondrial myopathy, encephalopathy, lactacidosis, and stroke (MELAS) can manifest itself in infants, children, or young adults. Strokes, accompanied by vomiting and seizures, are one of the most serious symptoms; it is postulated that the metabolic impairment of mitochondria in certain areas of the brain is responsible for cell death and neurological lesions, rather than the impairment of blood flow as occurs in ischemic stroke.

Myoclonus Epilepsy Associated with Ragged-Red Fibers (MERRF) syndrome is one of a group of rare muscular disorders that are called mitochondrial encephalomyopathies. Mitochondrial encephalomyopathies are disorders in which a defect in the genetic material arises from a part of the cell structure that releases energy (mitochondria). This can cause a dysfunction of the brain and muscles (encephalomyopathies). The mitochondrial defect as well as "ragged-red fibers" (an abnormality of tissue when viewed under a microscope) are always present. The most characteristic symptom of MERRF syndrome is myoclonic seizures that are usually sudden, brief, jerking, spasms that can affect the limbs or the entire body, difficulty speaking (dysarthria), optic atrophy, short stature, hearing loss, dementia, and involuntary jerking of the eyes (nystagmus) may also occur.

Leigh's disease is a rare inherited neurometabolic disorder characterized by degeneration of the central nervous system where the symptoms usually begin between the ages of 3 months to 2 years and progress rapidly. In most children, the first signs may be poor sucking ability and loss of head control and motor skills. These symptoms may be accompanied by loss of appetite, vomiting, irritability, continuous crying, and seizures. As the disorder progresses, symptoms may also include generalized weakness, lack of muscle tone, and episodes of lactic acidosis, which can lead to impairment of respiratory and kidney function. Heart problems may also occur.

Co-Enzyme Q10 Deficiency is a respiratory chain disorder, with syndromes such as myopathy with exercise intolerance and recurrent myoglobin in the urine manifested by ataxia, seizures or mental retardation and leading to renal failure (Di Mauro et al., (2005) Neuromusc. Disord., 15:311-315), childhood-onset cerebellar ataxia and cerebellar atrophy (Masumeci et al., (2001) Neurology 56:849-855 and Lamperti et al., (2003) 60:1206:1208); and infantile encephalomyopathy associated with nephrosis. Biochemical measurement of muscle homogenates of patients with CoQ10 deficiency showed severely decreased activities of respiratory chain complexes I and II+III, while complex IV (COX) was moderately decreased (Gempel et al., (2007) Brain, 130(8):2037-2044).

Complex I Deficiency or NADH dehydrogenase NADH-CoQ reductase deficiency is a respiratory chain disorder, with symptoms classified by three major forms: (1) fatal infantile multisystem disorder, characterized by developmental delay, muscle weakness, heart disease, congenital lactic acidosis, and respiratory failure; (2) myopathy beginning in childhood or in adult life, manifesting as exercise intolerance or weakness; and (3) mitochondrial encephalomyopathy (including MELAS), which may begin in childhood or adult life and consists of variable combinations of symptoms and signs, including ophthalmoplegia, seizures, dementia, ataxia, hearing loss, pigmentary retinopathy, sensory neuropathy, and uncontrollable movements.

Complex II Deficiency or Succinate dehydrogenase deficiency is a respiratory chain disorder with symptoms including encephalomyopathy and various manifestations, including failure to thrive, developmental delay, hypotonia, lethargy, respiratory failure, ataxia, myoclonus and lactic acidosis.

Complex III Deficiency or Ubiquinone-cytochrome C oxidoreductase deficiency is a respiratory chain disorder with symptoms categorized in four major forms: (1) fatal infantile encephalomyopathy, congenital lactic acidosis, hypotonia, dystrophic posturing, seizures, and coma; (2) encephalomyopathies of later onset (childhood to adult life): various combinations of weakness, short stature, ataxia, dementia, hearing loss, sensory neuropathy, pigmentary retinopathy, and pyramidal signs; (3) myopathy, with exercise intolerance evolving into fixed weakness; and (4) infantile histiocytoid cardiomyopathy.

Complex IV Deficiency or Cytochrome C oxidase deficiency is a respiratory chain disorder with symptoms categorized in two major forms: (1) encephalomyopathy, where patients typically are normal for the first 6 to 12 months of life and then show developmental regression, ataxia, lactic acidosis, optic atrophy, ophthalmoplegia, nystagmus, dystonia, pyramidal signs, respiratory problems and frequent seizures; and (2) myopathy with two main variants: (a) Fatal infantile myopathy—may begin soon after birth and accompanied by hypotonia, weakness, lactic acidosis, ragged-red fibers, respiratory failure, and kidney problems: and (b) Benign infantile myopathy—may begin soon after birth and accompanied by hypotonia, weakness, lactic acidosis, ragged-red fibers, respiratory problems, but (if the child survives) followed by spontaneous improvement.

Complex V Deficiency or ATP synthase deficiency is a respiratory chain disorder including symptoms such as slow, progressive myopathy.

CPEO or Chronic Progressive External Ophthalmoplegia Syndrome is a respiratory chain disorder including symptoms such as visual myopathy, retinitis pigmentosa, or dysfunction of the central nervous system.

Kearns-Sayre Syndrome (KSS) is a mitochondrial disease characterized by a triad of features including: (1) typical onset in persons younger than age 20 years; (2) chronic, progressive, external ophthalmoplegia; and (3) pigmentary degeneration of the retina. In addition, KSS may include cardiac conduction defects, cerebellar ataxia, and raised cerebrospinal fluid (CSF) protein levels (e.g., >100 mg/dL). Additional features associated with KSS may include myopathy, dystonia, endocrine abnormalities (e.g., diabetes, growth retardation or short stature, and hypoparathyroidism), bilateral sensorineural deafness, dementia, cataracts, and proximal renal tubular acidosis.

Maternally inherited diabetes and deafness (MIDD) is a mitochondrial disorder characterized by maternally transmitted diabetes and sensorineural deafness. In most cases, MIDD is caused by a point mutation in the mitochondrial gene MT-TL1, encoding the mitochondrial tRNA for leucine, and in rare cases in MT-TE and MT-TK genes, encoding the mitochondrial tRNAs for glutamic acid, and lysine, respectively.

In addition to congenital disorders involving inherited defective mitochondria, acquired mitochondrial dysfunction contributes to diseases, particularly neurodegenerative disorders associated with aging like Parkinson's, Alzheimer's, and Huntington's Diseases. The incidence of somatic mutations in mitochondrial DNA rises exponentially with age; diminished respiratory chain activity is found universally in aging people. Mitochondrial dysfunction is also implicated in excitotoxic, neuronal injury, such as that associated with cerebrovascular accidents, seizures and ischemia.

Some of the above diseases appear to be caused by defects in Complex I of the respiratory chain. Electron transfer from Complex I to the remainder of the respiratory chain is mediated by the compound coenzyme Q (also known as Ubiquinone). Oxidized coenzyme Q ($CoQ_{ox}$ or Ubiquinone) is reduced by Complex I to reduced coenzyme Q ($CoQ_{red}$ or Ubiquinol). The reduced coenzyme Q then transfers its electrons to Complex III of the respiratory chain, where it is re-oxidized to $CoQ_{ox}$ (Ubiquinone). $CoQ_{ox}$ can then participate in further iterations of electron transfer.

Very few treatments are available for patients suffering from these mitochondrial diseases. Recently, the compound Idebenone has been proposed for treatment of Friedreich's ataxia. While the clinical effects of Idebenone have been relatively modest, the complications of mitochondrial diseases can be so severe that even marginally useful therapies are preferable to the untreated course of the disease. Another compound, MitoQ, has been proposed for treating mitochondrial disorders (see U.S. Pat. No. 7,179,928); clinical results for MitoQ have not yet been reported. Administration of coenzyme Q10 (CoQ10) and vitamin supplements has shown only transient beneficial effects in individual cases of KSS. CoQ10 supplementation has also been used for the treatment of CoQ10 deficiency with mixed results.

Oxidative stress is suspected to be important in neurodegenerative diseases such as Motor Neuron Disease, Amyotrophic Lateral Sclerosis (ALS), Creutzfeldt-Jakob disease, Machado-Joseph disease, Spino-cerebellar ataxia, Multiple sclerosis(MS), Parkinson's disease, Alzheimer's disease, and Huntington's disease. Oxidative stress is thought to be linked to certain cardiovascular disease and also plays a role in the ischemic cascade due to oxygen reperfusion injury following hypoxia. This cascade includes both strokes and heart attacks.

Damage accumulation theory, also known as the free radical theory of aging, invokes random effects of free radicals produced during aerobic metabolism that cause damage to DNA, lipids and proteins and accumulate over time. The concept of free radicals playing a role in the aging process was first introduced by Himan D (1956), Aging—A theory based on free-radical and radiation chemistry J. Gerontol. 11, 298-300.

According to the free radical theory of aging, the process of aging begins with oxygen metabolism (Valko et al, (2004) Role of oxygen radicals in DNA damage and cancer incidence, Mol. Cell. Biochem., 266, 37-56). Even under ideal conditions some electrons "leak" from the electron transport chain. These leaking electrons interact with oxygen to produce superoxide radicals, so that under physiological conditions, about 1-3% of the oxygen molecules in the mitochondria are converted into superoxide. The primary site of radical oxygen damage from superoxide radical is mitochondrial DNA (mtDNA) (Cadenas et al., (2000) Mitochondrial free radical generation, oxidative stress and aging, Free Radic. Res, 28, 601-609). The cell repairs much of the damage done to nuclear DNA (nDNA) but mtDNA repair seems to be less efficient. Therefore, extensive mtDNA damage accumulates over time and shuts down mitochondria causing cells to die and the organism to age.

Some of the diseases associated with increasing age are cancer, diabetes mellitus, hypertension, atherosclerosis, ischemia/reperfusion injury, rheumatoid arthritis, neurodegenerative disorders such as dementia, Alzheimer's and Parkinson's. Diseases resulting from the process of aging as a physiological decline include decreases in muscle strength, cardiopulmonary function, vision and hearing as well as wrinkled skin and graying hair.

The ability to adjust biological production of energy has applications beyond the diseases described above. Various other disorders can result in suboptimal levels of energy biomarkers (sometimes also referred to as indicators of energetic function), such as ATP levels. Treatments for these disorders are also needed, in order to modulate one or more energy biomarkers to improve the health of the patient. In other applications, it can be desirable to modulate certain energy biomarkers away from their normal values in an individual that is not suffering from disease. For example, if an individual is undergoing an extremely strenuous undertaking, it can be desirable to raise the level of ATP in that individual.

BRIEF SUMMARY OF THE INVENTION

In one aspect of the invention is a compound of the formula:

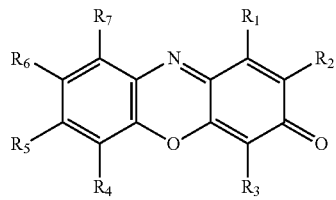

wherein: $R_1$ and $R_2$ are independently selected from the group consisting of: —H, —$C_1$-$C_4$ alkyl, —O—$C_1$-$C_4$ alkyl, and —$C_1$-$C_4$ haloalkyl, and $R_3$ is selected from the group consisting of: —H, —$C_1$-$C_{12}$ alkyl, —O—$C_1$-$C_{12}$ alkyl, and —$C_1$-$C_{12}$ haloalkyl; or $R_1$ and $R_2$ are both —$CH_3$ or $R_1$ and $R_2$ are both —$OCH_3$, and $R_3$ is selected from the group consisting of:

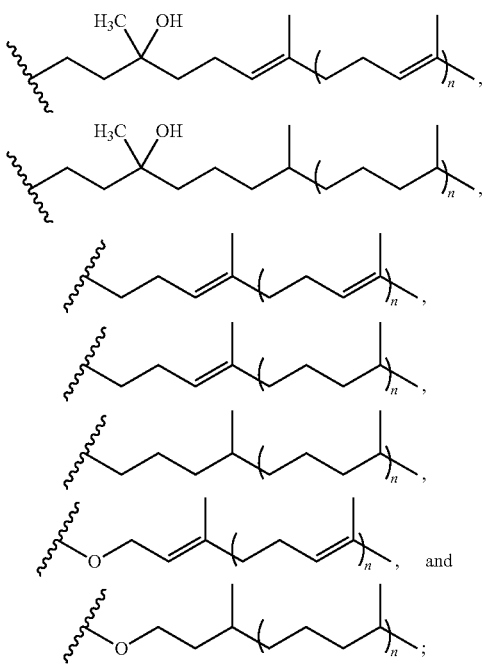

n is 0, 1, 2, 3, or 4; $R_4$, $R_5$, $R_6$, and $R_7$ are independently selected from the group consisting of: —H, —$C_1$-$C_{12}$ alkyl, —$C_2$-$C_{12}$ alkenyl, —$C_1$-$C_{12}$ haloalkyl, —O—$C_1$-$C_{12}$ alkyl, —O—$C_1$-$C_{12}$ haloalkyl, —$C_6$-$C_{10}$ aryl, —O—$C_6$-$C_{10}$ aryl, —$C_1$-$C_6$ alkyl-$C_6$-$C_{10}$ aryl, —O—$C_1$-$C_6$ alkyl-$C_6$-$C_{10}$ aryl, —N—($R_8$)($R_9$),

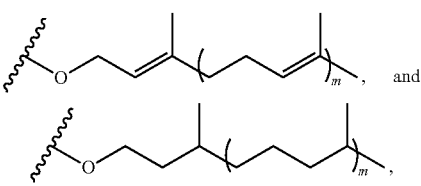

with the proviso that at least two of $R_4$, $R_5$, $R_6$, and $R_7$ are independently selected from the group consisting of: —H and —$CH_3$; $R_8$ and $R_9$ are independently —H or —$C_1$-$C_{12}$ alkyl; and m is 0, 1, 2, or 3; or a stereoisomer, mixture of stereoisomers, solvate, hydrate, or pharmaceutically acceptable salt thereof; with the proviso that the compound is not:

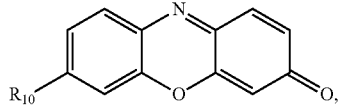

wherein $R_{10}$ is —H, —OH, —O-alkyl, or —O-benzyl, or a stereoisomer, mixture of stereoisomers, solvate, hydrate, or pharmaceutically acceptable salt thereof. In some embodiments, one of $R_1$, $R_2$, and $R_3$ is not —H. In some embodiments, two of $R_1$, $R_2$, and $R_3$ are not —H. In some embodiments, $R_1$, $R_2$, and $R_3$ are not —H. In some embodiments, one of $R_1$, $R_2$, and $R_3$ is —CH$_3$. In some embodiments, two of $R_1$, $R_2$, and $R_3$ are —CH$_3$. In some embodiments, $R_1$, $R_2$, and $R_3$ are —CH$_3$. In some embodiments, two of $R_1$, $R_2$, and $R_3$ are —CH$_3$ and one of $R_1$, $R_2$, and $R_3$ is —H. In some embodiments, $R_1$ and $R_3$ are —CH$_3$, and $R_2$ is —H. In some embodiments, $R_1$ and $R_2$ are —CH$_3$. In some embodiments, $R_1$ and $R_2$ are —OCH$_3$. In some embodiments, $R_1$ and $R_2$ are —OCH$_3$, and $R_3$ is —CH$_3$. In some embodiments, $R_1$ and $R_2$ are —CH$_3$, and $R_3$ is -n-$C_1$-$C_{12}$ alkyl. In some embodiments, $R_1$ and $R_2$ are —OCH$_3$, and $R_3$ is -n-$C_1$-$C_{12}$ alkyl. In some embodiments, $R_1$ and $R_2$ are —CH$_3$, and $R_3$ is selected from the group consisting of:

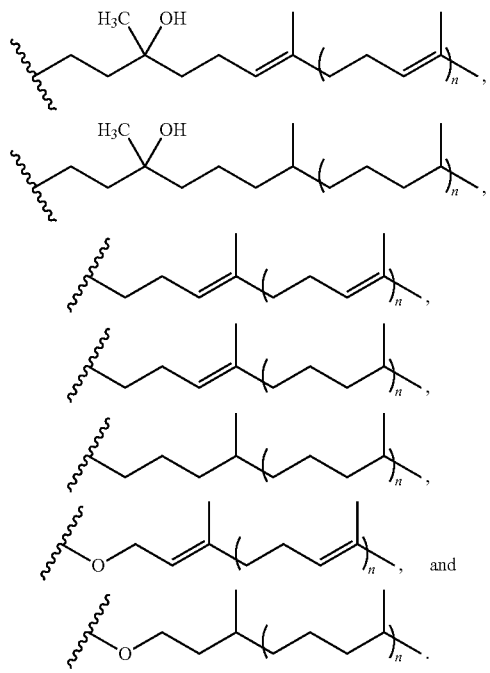

In some embodiments, $R_1$ and $R_2$ are —CH$_3$, and $R_3$ is

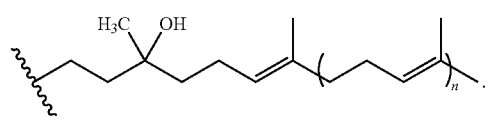

In some embodiments, $R_1$ and $R_2$ are —CH$_3$, and $R_3$ is

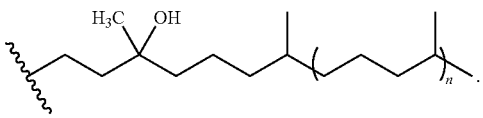

In some embodiments, $R_1$ and $R_2$ are —CH$_3$, and $R_3$ is

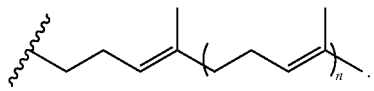

In some embodiments, $R_1$ and $R_2$ are —OCH$_3$, and $R_3$ is selected from the group consisting of:

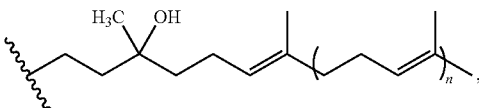
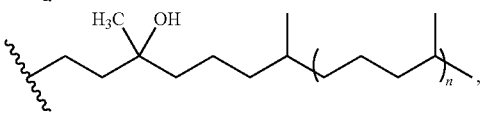
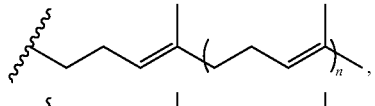
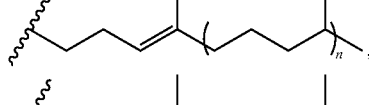
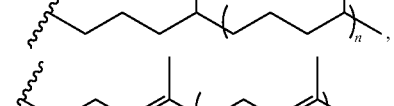
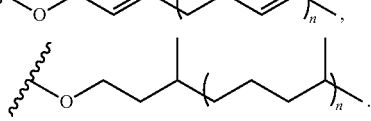

In some embodiments, $R_1$ and $R_2$ are —OCH$_3$, and $R_3$ is

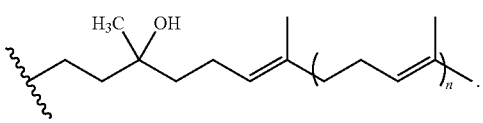

In some embodiments, $R_1$ and $R_2$ are —OCH$_3$, and $R_3$ is

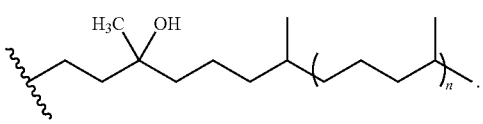

In some embodiments, $R_1$ and $R_2$ are —OCH$_3$, and wherein $R_3$ is

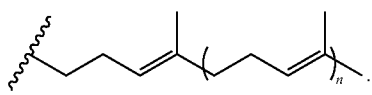

In some embodiments, $R_1$ and $R_2$ are independently —H or —$C_1$-$C_4$ alkyl. In some embodiments, $R_1$, $R_2$, and $R_3$ are —H. In some embodiments, including any of the foregoing embodiments, n is 0. In some embodiments, including any of the foregoing embodiments, n is 1. In some embodiments, including any of the foregoing embodiments, n is 2. In some embodiments, including any of the foregoing embodiments, n is 3. In some embodiments, including any of the foregoing embodiments, n is 4. In some embodiments, including any of the foregoing embodiments, two of $R_4$, $R_5$, $R_6$, and $R_7$ are —H. In some embodiments, including any of the foregoing embodiments, three of $R_4$, $R_5$, $R_6$, and $R_7$ are —H. In some embodiments, including any of the foregoing embodiments, $R_4$, $R_5$, $R_6$, and $R_7$ are —H. In some embodiments, including any of the foregoing embodiments, at least one of $R_4$, $R_5$, $R_6$, and $R_7$ is independently selected from the group consisting of: —$C_1$-$C_{12}$ alkyl, —$C_1$-$C_{12}$ haloalkyl, —O—$C_1$-$C_{12}$ alkyl, —O—$C_1$-$C_6$ alkyl-$C_6$-$C_{10}$ aryl, —N—($R_8$)($R_9$), and

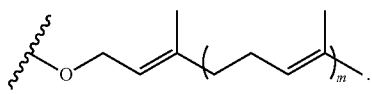

In some embodiments, including any of the foregoing embodiments, at least one of $R_4$, $R_5$, $R_6$, and $R_7$ is independently selected from the group consisting of: —$C_1$-$C_6$ alkyl, —O—$C_1$-$C_6$ alkyl, —N—($R_8$)($R_9$) wherein $R_8$ and $R_9$ are independently —H or —$C_1$-$C_4$ alkyl, —$CF_3$, —O-benzyl, and

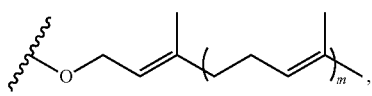

wherein m is 1 or 2. In some embodiments, including any of the foregoing embodiments, three of $R_4$, $R_5$, $R_6$, and $R_7$ are —H, and the other is —$N(CH_3)_2$. In some embodiments, including any of the foregoing embodiments, three of $R_4$, $R_5$, $R_6$, and $R_7$ are —H, and the other is —O-benzyl. In some embodiments, including any of the foregoing embodiments, three of $R_4$, $R_5$, $R_6$, and $R_7$ are —H, and the other is —O—$CH_3$. In some embodiments, including any of the foregoing embodiments, three of $R_4$, $R_5$, $R_6$, and $R_7$ are —H, and the other is —O-n-$C_2$-$C_5$ alkyl. In some embodiments, including any of the foregoing embodiments, three of $R_4$, $R_5$, $R_6$, and $R_7$ are —H, and the other is —$CF_3$. In some embodiments, including any of the foregoing embodiments, three of $R_4$, $R_5$, $R_6$, and $R_7$ are —H, and the other is

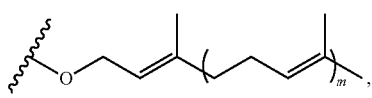

wherein m is 1 or 2. In some embodiments, including any of the foregoing embodiments, three of $R_4$, $R_5$, $R_6$, and $R_7$ are —H, and the other is —$CH_3$. In some embodiments, including any of the foregoing embodiments, m is 0. In some embodiments, including any of the foregoing embodiments, m is 1. In some embodiments, including any of the foregoing embodiments, m is 2. In some embodiments, including any of the foregoing embodiments, m is 3. In some embodiments, including any of the foregoing embodiments, the compound has the formula:

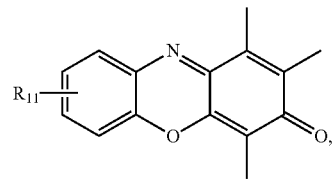

wherein $R_{11}$ is selected from the group consisting of: —$C_1$-$C_6$ alkyl, —O—$C_1$-$C_6$ alkyl, —$N(CH_3)_2$, —$CF_3$, —O-benzyl, and

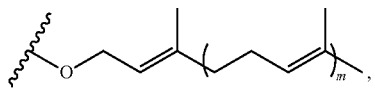

wherein m is 1 or 2, or a stereoisomer, mixture of stereoisomers, solvate, hydrate, or pharmaceutically acceptable salt thereof. In some embodiments, including any of the foregoing embodiments, the compound has the formula:

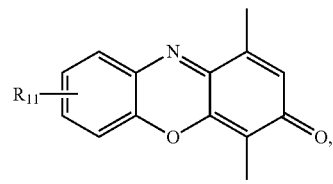

wherein $R_{11}$ is selected from the group consisting of: —$C_1$-$C_6$ alkyl, —O—$C_1$-$C_6$ alkyl, —$N(CH_3)_2$, —$CF_3$, —O-benzyl, and

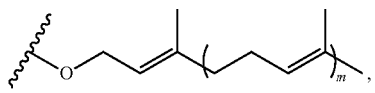

wherein m is 1 or 2, or a stereoisomer, mixture of stereoisomers, solvate, hydrate, or pharmaceutically acceptable salt thereof. In some embodiments, including any of the foregoing embodiments, the compound has the formula:

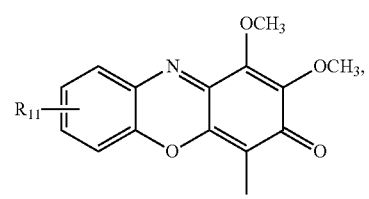

wherein $R_{11}$ is selected from the group consisting of: —$C_1$-$C_6$ alkyl, —O—$C_1$-$C_6$ alkyl, —$N(CH_3)_2$, —$CF_3$, —O-benzyl, and

11

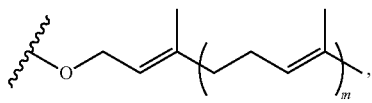

wherein m is 1 or 2, or a stereoisomer, mixture of stereoisomers, solvate, hydrate, or pharmaceutically acceptable salt thereof. In some embodiments, including any of the foregoing embodiments, the compound has the formula:

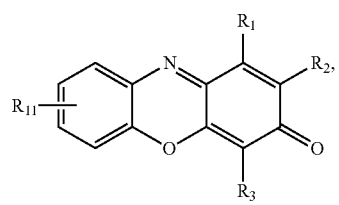

12 wherein $R_1$ and $R_2$ are —$CH_3$, or $R_1$ and $R_2$ are —$OCH_3$, and wherein $R_3$ is:

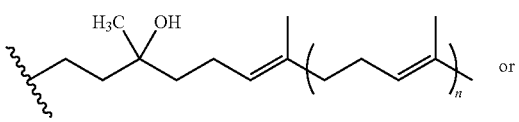 or

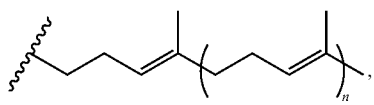, wherein n is 1 or 2, or a stereoisomer, mixture of stereoisomers, solvate, hydrate, or pharmaceutically acceptable salt thereof. In some embodiments, including any of the foregoing embodiments, the compound is selected from the group consisting of:

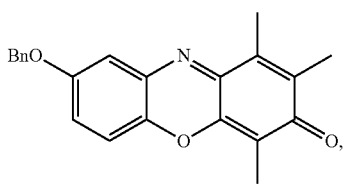 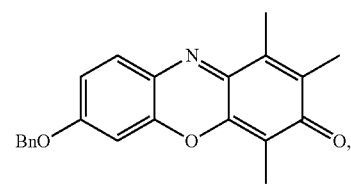 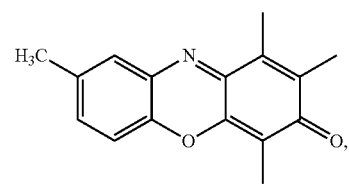

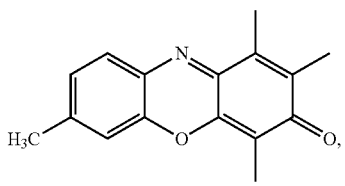 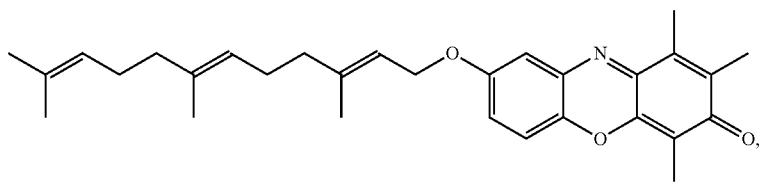

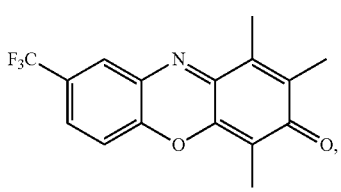 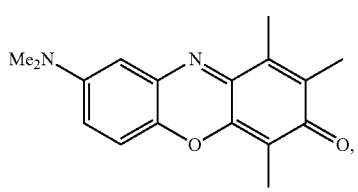 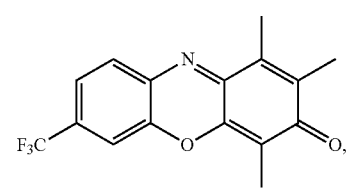

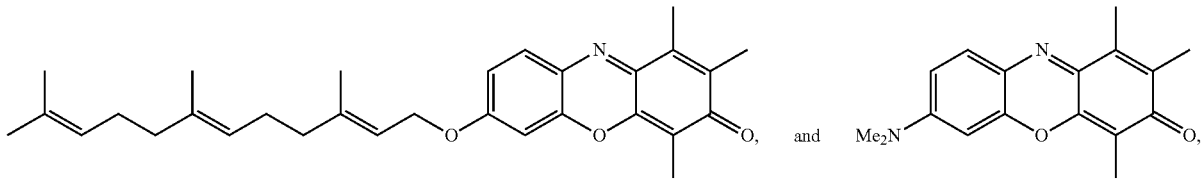

or a stereoisomer, mixture of stereoisomers, solvate, hydrate, or pharmaceutically acceptable salt thereof. In some embodiments, including any of the foregoing embodiments, the compound is selected from the group consisting of:

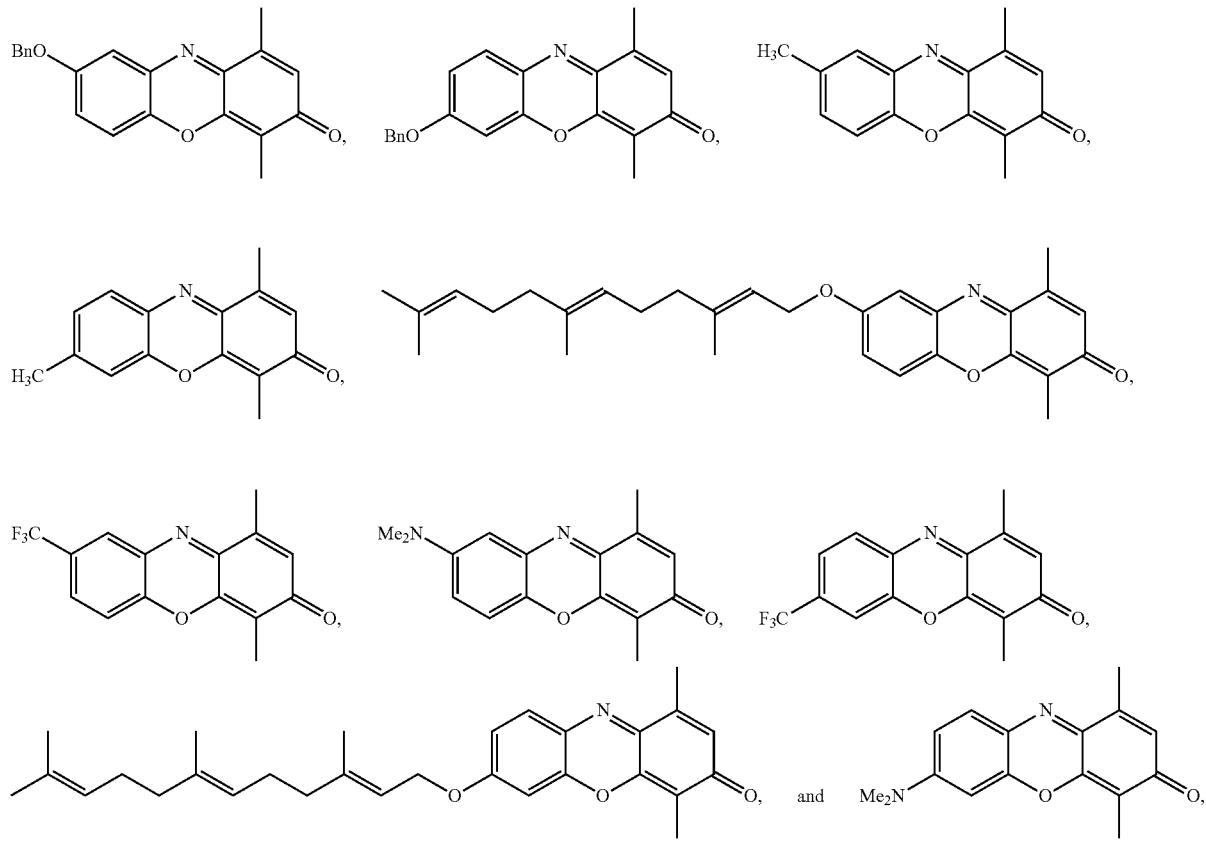

or a stereoisomer, mixture of stereoisomers, solvate, hydrate, or pharmaceutically acceptable salt thereof. In some embodiments, including any of the foregoing embodiments, the compound is selected from the group consisting of:

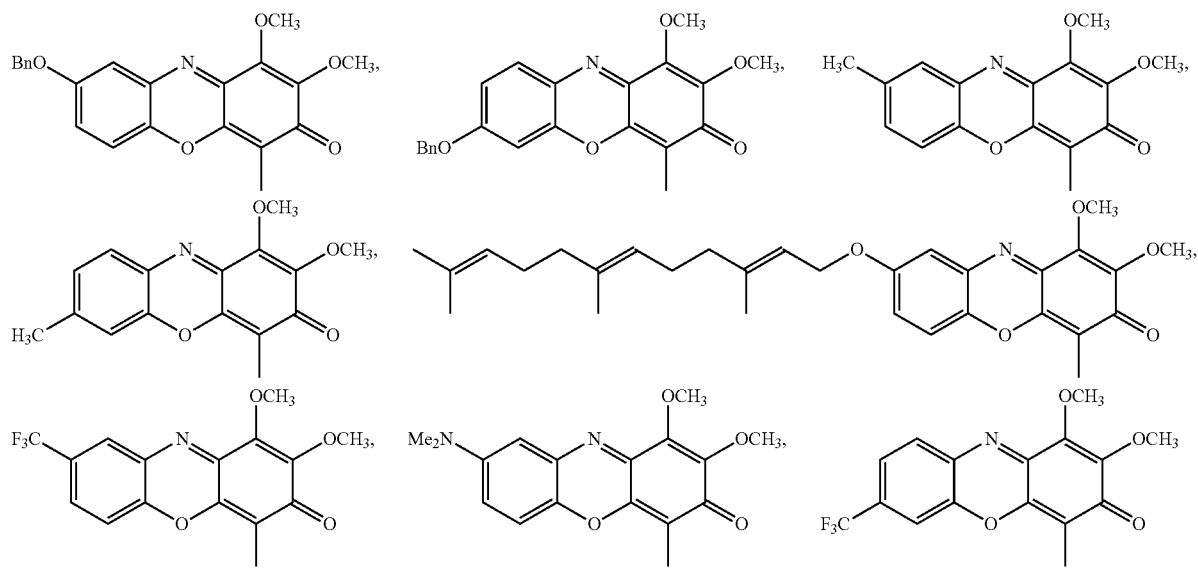

-continued

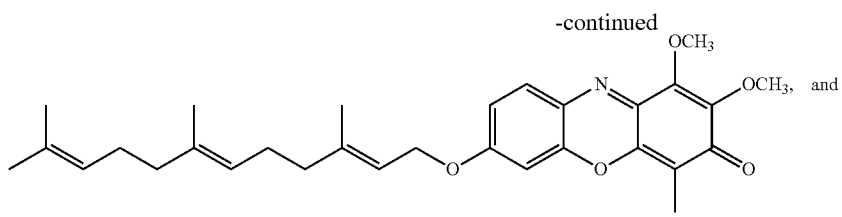 and 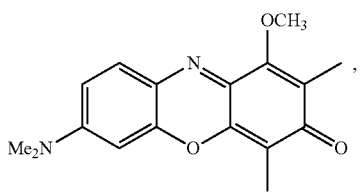

or a stereoisomer, mixture of stereoisomers, solvate, hydrate, or pharmaceutically acceptable salt thereof. In some embodiments, including any of the foregoing embodiments, the compound is selected from the group consisting of:

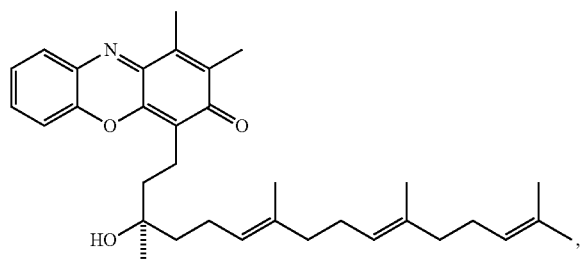

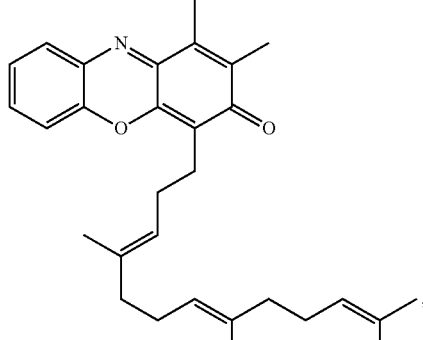

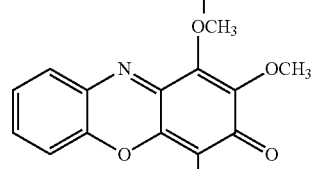, and

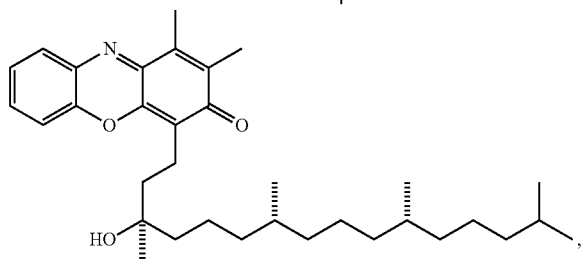

or a stereoisomer, mixture of stereoisomers, solvate, hydrate, or pharmaceutically acceptable salt thereof. In some embodiments, including any of the foregoing embodiments, the compound has an EC50 of less than about 1 micromolar, as measured by an assay described in any one of Examples 1-6. In some embodiments, including any of the foregoing embodiments, the compound has an EC50 of less than about 500 nM, as measured by an assay described in any one of Examples 1-6. In some embodiments, including any of the foregoing embodiments, the compound has an EC50 of less than about 250 nM, as measured by an assay described in any one of Examples 1-6. The compound of the invention can be any individual compound of Formula I, or a stereoisomer, mixture of stereoisomers, solvate, hydrate, or pharmaceutically acceptable salt thereof. Compositions comprising combinations of compounds of the invention are also contemplated.

In another aspect of the invention is a pharmaceutical formulation comprising a compound as described herein, including any of the foregoing or hereafter embodiments, and a pharmaceutically acceptable excipient.

In another aspect of the invention is a method of treating or suppressing an oxidative stress disorder, modulating one or more energy biomarkers, normalizing one or more energy biomarkers, or enhancing one or more energy biomarkers, comprising administering to a subject a therapeutically effective amount or effective amount of a compound of formula (I):

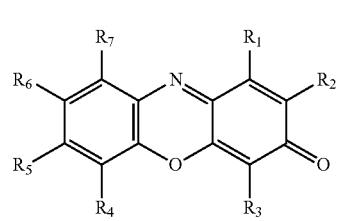

wherein: $R_1$ and $R_2$ are independently selected from the group consisting of: —H, —$C_1$-$C_4$ alkyl, —O—$C_1$-$C_4$ alkyl, and —$C_1$-$C_4$ haloalkyl, and $R_3$ is selected from the group consisting of: —H, —$C_1$-$C_{12}$ alkyl, —O—$C_1$-$C_{12}$ alkyl, and —$C_1$-$C_{12}$ haloalkyl; or $R_1$ and $R_2$ are both —$CH_3$ or $R_1$ and $R_2$ are both —$OCH_3$, and $R_3$ is selected from the group consisting of:

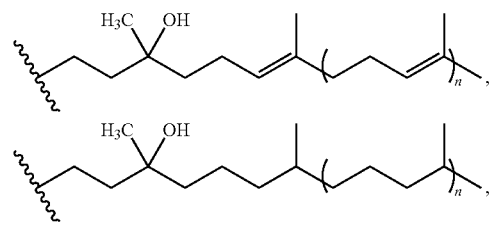

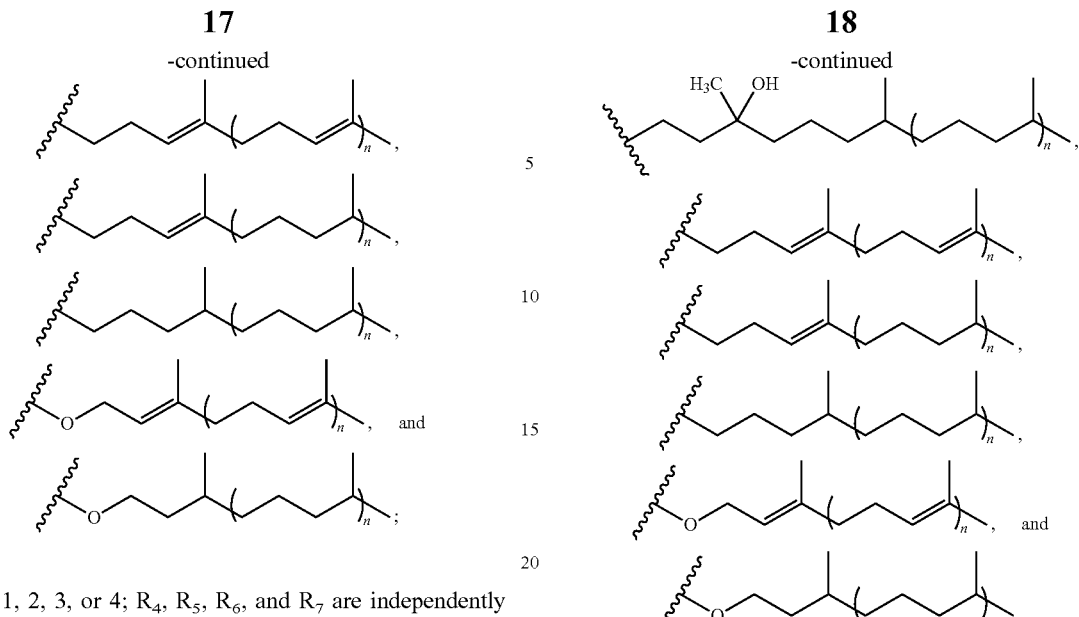

n is 0, 1, 2, 3, or 4; $R_4$, $R_5$, $R_6$, and $R_7$ are independently selected from the group consisting of: —H, —$C_1$-$C_{12}$ alkyl, —$C_2$-$C_{12}$ alkenyl, —$C_1$-$C_{12}$ haloalkyl, —O—$C_1$-$C_{12}$ alkyl, —O—$C_1$-$C_{12}$ haloalkyl, —$C_6$-$C_{10}$ aryl, —O—$C_6$-$C_{10}$ aryl, —$C_1$-$C_6$ alkyl-$C_6$-$C_{10}$ aryl, —O—$C_1$-$C_6$ alkyl-$C_6$-$C_{10}$ aryl, —N—($R_8$)($R_9$),

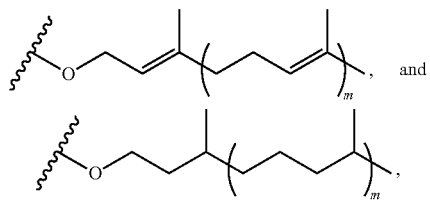

with the proviso that at least two of $R_4$, $R_5$, $R_6$, and $R_7$ are independently selected from the group consisting of: —H and —$CH_3$; $R_8$ and $R_9$ are independently —H or —$C_1$-$C_{12}$ alkyl; and m is 0, 1, 2, or 3; or a stereoisomer, mixture of stereoisomers, solvate, hydrate, or pharmaceutically acceptable salt thereof. In some embodiments, one of $R_1$, $R_2$, and $R_3$ is not —H. In some embodiments, two of $R_1$, $R_2$, and $R_3$ are not —H. In some embodiments, $R_1$, $R_2$, and $R_3$ are not —H. In some embodiments, one of $R_1$, $R_2$, and $R_3$ is —$CH_3$. In some embodiments, two of $R_1$, $R_2$, and $R_3$ are —$CH_3$. In some embodiments, $R_1$, $R_2$, and $R_3$ are —$CH_3$. In some embodiments, two of $R_1$, $R_2$, and $R_3$ are —$CH_3$ and one of $R_1$, $R_2$, and $R_3$ is —H. In some embodiments, $R_1$ and $R_3$ are —$CH_3$, and $R_2$ is —H. In some embodiments, $R_1$ and $R_2$ are —$CH_3$. In some embodiments, $R_1$ and $R_2$ are —$OCH_3$. In some embodiments, $R_1$ and $R_2$ are —$OCH_3$, and $R_3$ is —$CH_3$. In some embodiments, $R_1$ and $R_2$ are —$CH_3$, and $R_3$ is -n-$C_1$-$C_{12}$ alkyl. In some embodiments, $R_1$ and $R_2$ are —$OCH_3$, and $R_3$ is -n-$C_1$-$C_{12}$ alkyl. In some embodiments, $R_1$ and $R_2$ are —$CH_3$, and wherein $R_3$ is selected from the group consisting of:

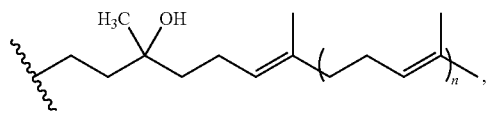

In some embodiments, $R_1$ and $R_2$ are —$CH_3$, and $R_3$ is

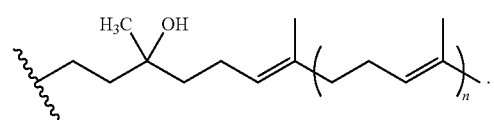

In some embodiments, $R_1$ and $R_2$ are —$CH_3$, and $R_3$ is

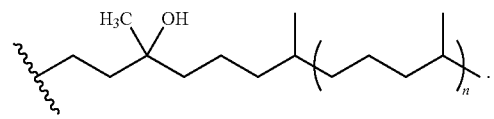

In some embodiments, $R_1$ and $R_2$ are —$CH_3$, and $R_3$ is

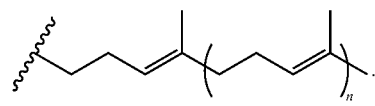

In some embodiments, $R_1$ and $R_2$ are —$OCH_3$, and $R_3$ is selected from the group consisting of:

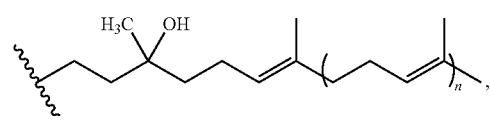
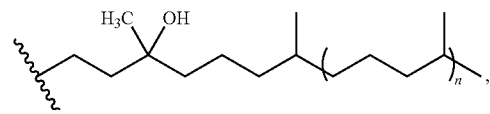
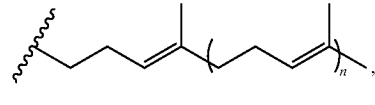

-continued

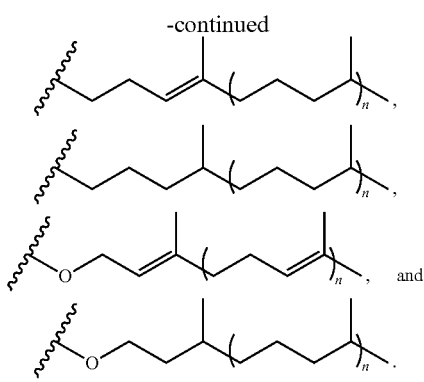

In some embodiments, $R_1$ and $R_2$ are —$OCH_3$, and $R_3$ is

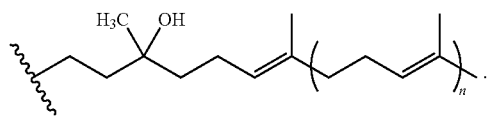

In some embodiments, $R_1$ and $R_2$ are —$OCH_3$, and $R_3$ is

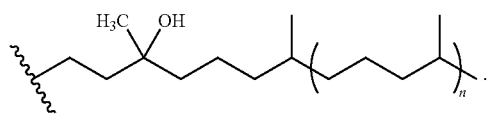

In some embodiments, $R_1$ and $R_2$ are —$OCH_3$, and $R_3$ is

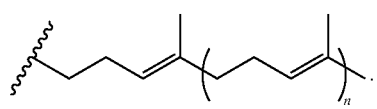

In some embodiments, $R_1$ and $R_2$ are independently —H or —$C_1$-$C_4$ alkyl. In some embodiments, $R_1$, $R_2$, and $R_3$ are —H. In some embodiments, including any of the foregoing embodiments, n is 0. In some embodiments, including any of the foregoing embodiments, n is 1. In some embodiments, including any of the foregoing embodiments, n is 2. In some embodiments, including any of the foregoing embodiments, n is 3. In some embodiments, including any of the foregoing embodiments, n is 4. In some embodiments, including any of the foregoing embodiments, two of $R_4$, $R_5$, $R_6$, and $R_7$ are —H. In some embodiments, including any of the foregoing embodiments, three of $R_4$, $R_5$, $R_6$, and $R_7$ are —H. In some embodiments, including any of the foregoing embodiments, $R_4$, $R_5$, $R_6$, and $R_7$ are —H. In some embodiments, including any of the foregoing embodiments, at least one of $R_4$, $R_5$, $R_6$, and $R_7$ is independently selected from the group consisting of: —$C_1$-$C_{12}$ alkyl, —$C_1$-$C_{12}$ haloalkyl, —O—$C_1$-$C_{12}$ alkyl, —O—$C_1$-$C_{12}$ alkyl-$C_6$-$C_{10}$ aryl, —N—($R_8$)($R_9$), and

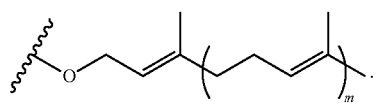

In some embodiments, including any of the foregoing embodiments, at least one of $R_4$, $R_5$, $R_6$, and $R_7$ is independently selected from the group consisting of: —$C_1$-$C_6$ alkyl, —O—$C_1$-$C_6$ alkyl, —N—($R_8$)($R_9$) wherein $R_8$ and $R_9$ are independently —H or —$C_1$-$C_4$ alkyl, —$CF_3$, —O-benzyl, and

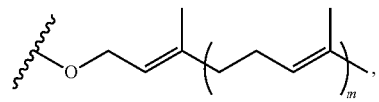

wherein m is 1 or 2. In some embodiments, including any of the foregoing embodiments, three of $R_4$, $R_5$, $R_6$, and $R_7$ are —H, and the other is —$N(CH_3)_2$. In some embodiments, including any of the foregoing embodiments, three of $R_4$, $R_5$, $R_6$, and $R_7$ are —H, and the other is —O-benzyl. In some embodiments, including any of the foregoing embodiments, three of $R_4$, $R_5$, $R_6$, and $R_7$ are —H, and the other is —O—$CH_3$. In some embodiments, including any of the foregoing embodiments, three of $R_4$, $R_5$, $R_6$, and $R_7$ are —H, and the other is —O-n-$C_2$-$C_5$ alkyl. In some embodiments, including any of the foregoing embodiments, three of $R_4$, $R_5$, $R_6$, and $R_7$ are —H, and the other is —$CF_3$. In some embodiments, including any of the foregoing embodiments, three of $R_4$, $R_5$, $R_6$, and $R_7$ are —H, and the other is

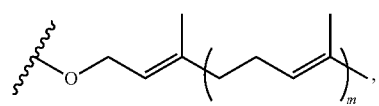

wherein m is 1 or 2. In some embodiments, including any of the foregoing embodiments, m is 0. In some embodiments, including any of the foregoing embodiments, m is 1. In some embodiments, including any of the foregoing embodiments, m is 2. In some embodiments, including any of the foregoing embodiments, m is 3. In some embodiments, including any of the foregoing embodiments, three of $R_4$, $R_5$, $R_6$, and $R_7$ are —H, and the other is —$CH_3$. In some embodiments, including any of the foregoing embodiments, the compound has the formula:

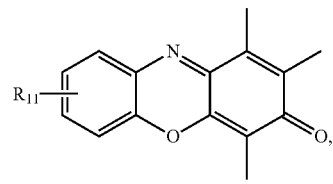

wherein $R_{11}$ is selected from the group consisting of: —$C_1$-$C_6$ alkyl, —O—$C_1$-$C_6$ alkyl, —$N(CH_3)_2$, —$CF_3$, —O-benzyl, and

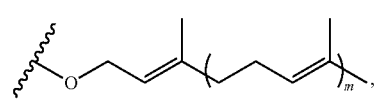

wherein m is 1 or 2, or a stereoisomer, mixture of stereoisomers, solvate, hydrate, or pharmaceutically acceptable salt thereof. In some embodiments, including any of the foregoing embodiments, the compound has the formula:

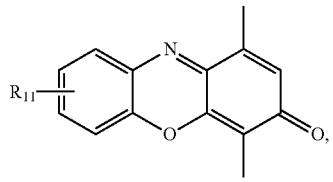

wherein $R_{11}$ is selected from the group consisting of: —$C_1$-$C_6$ alkyl, —O—$C_1$-$C_6$ alkyl, —N(CH$_3$)$_2$, —CF$_3$, —O-benzyl, and

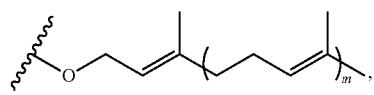

wherein m is 1 or 2, or a stereoisomer, mixture of stereoisomers, solvate, hydrate, or pharmaceutically acceptable salt thereof. In some embodiments, including any of the foregoing embodiments, the compound has the formula:

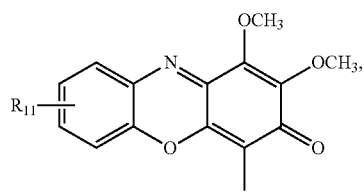

wherein $R_{11}$ is selected from the group consisting of: —$C_1$-$C_6$ alkyl, —O—$C_1$-$C_6$ alkyl, —N(CH$_3$)$_2$, —CF$_3$, —O-benzyl, and

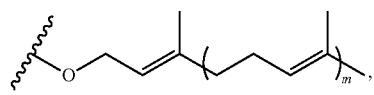

wherein m is 1 or 2, or a stereoisomer, mixture of stereoisomers, solvate, hydrate, or pharmaceutically acceptable salt thereof. In some embodiments, including any of the foregoing embodiments, the compound has the formula:

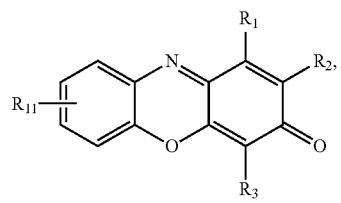

wherein $R_1$ and $R_2$ are —CH$_3$, or $R_1$ and $R_2$ are —OCH$_3$, and wherein $R_3$ is:

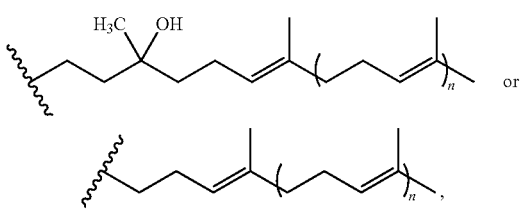

wherein n is 1 or 2, or a stereoisomer, mixture of stereoisomers, solvate, hydrate, or pharmaceutically acceptable salt thereof. In some embodiments, including any of the foregoing embodiments, the compound is not:

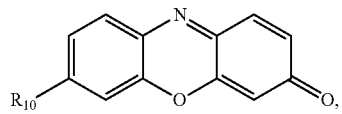

wherein $R_{10}$ is —H, —O-alkyl, or —O-benzyl, or a stereoisomer, mixture of stereoisomers, solvate, hydrate, or pharmaceutically acceptable salt thereof. In some embodiments, including any of the foregoing embodiments, the compound is selected from the group consisting of:

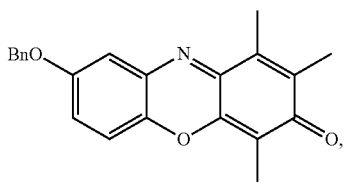 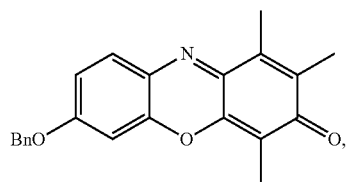 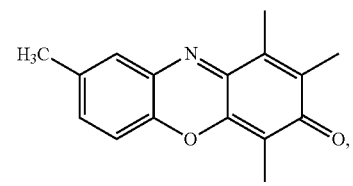

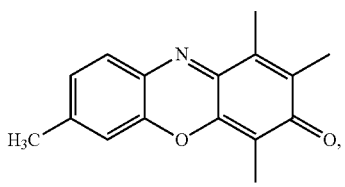 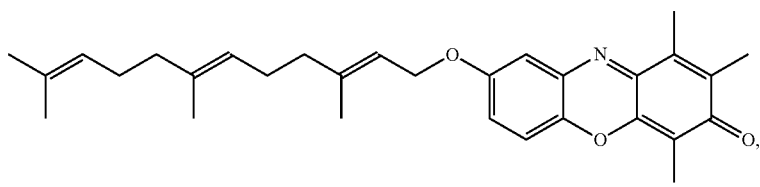

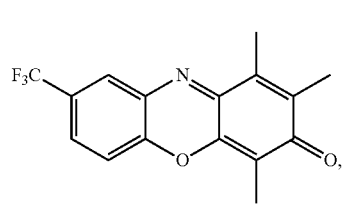 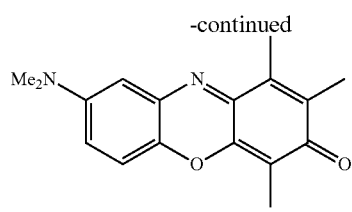 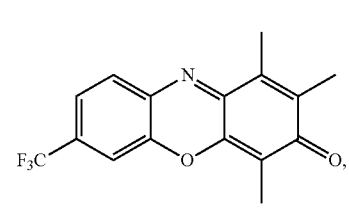

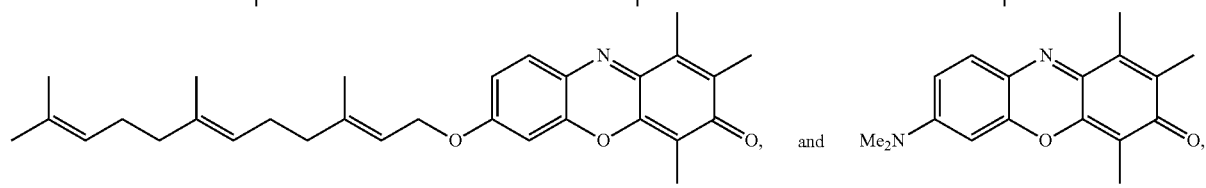

or a stereoisomer, mixture of stereoisomers, solvate, hydrate, or pharmaceutically acceptable salt thereof. In some embodiments, including any of the foregoing embodiments, the compound is selected from the group consisting of:

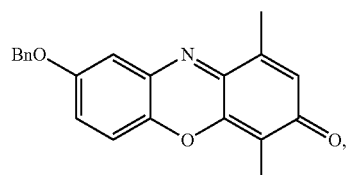 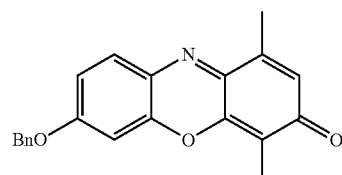 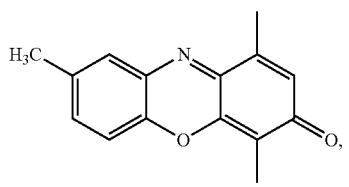

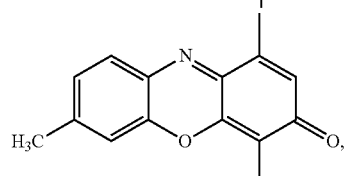 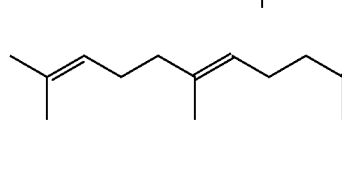

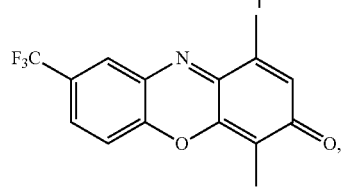 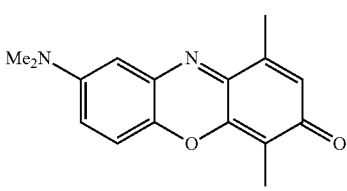 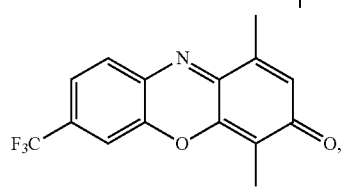

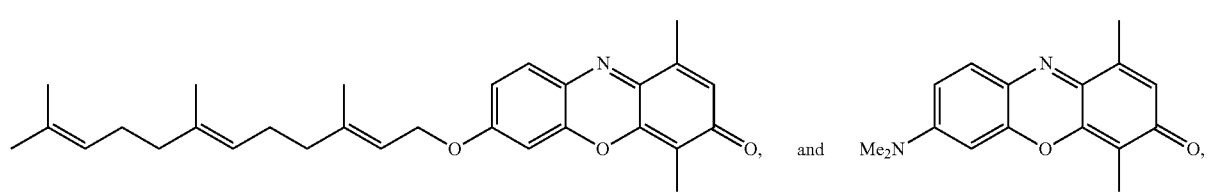

or a stereoisomer, mixture of stereoisomers, solvate, hydrate, or pharmaceutically acceptable salt thereof. In some embodiments, including any of the foregoing embodiments, the compound is selected from the group consisting of:

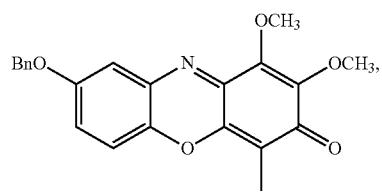 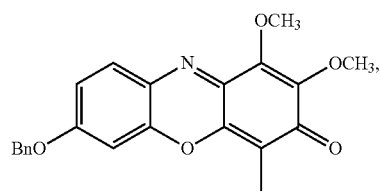 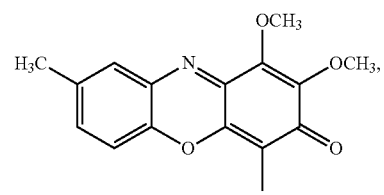

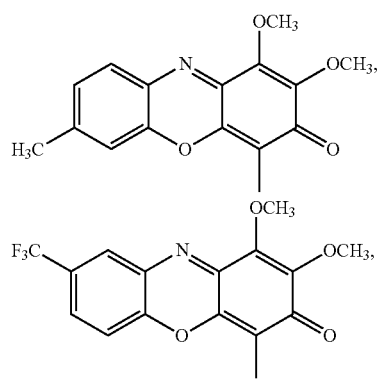
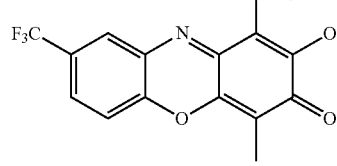
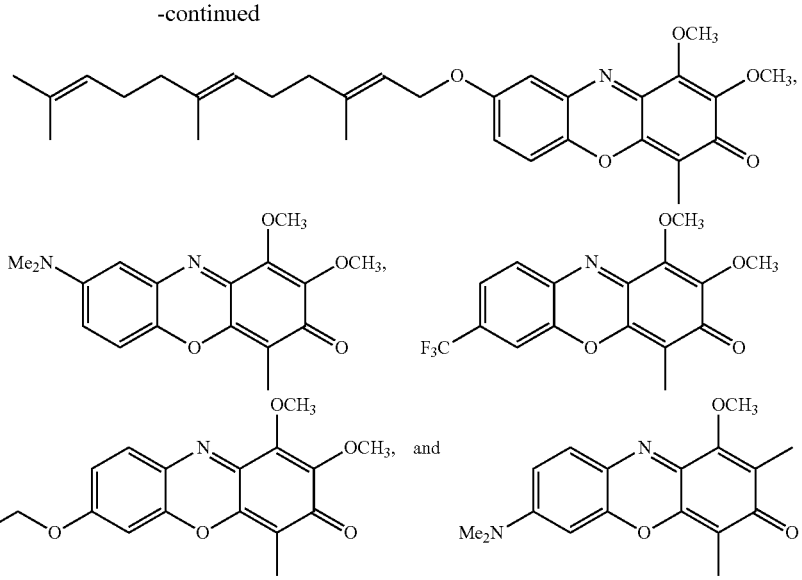

or a stereoisomer, mixture of stereoisomers, solvate, hydrate, or pharmaceutically acceptable salt thereof. In some embodiments, including any of the foregoing embodiments, the compound is selected from the group consisting of:

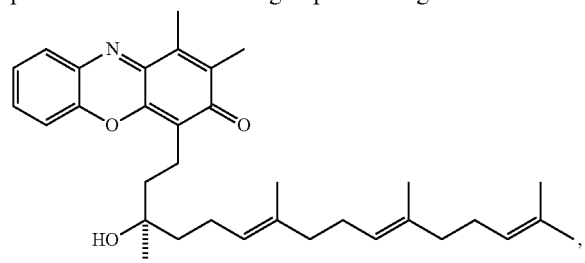
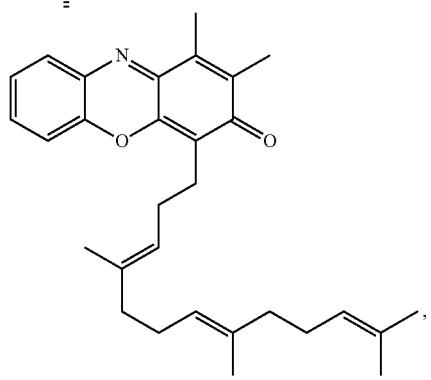
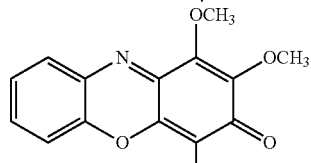

, and

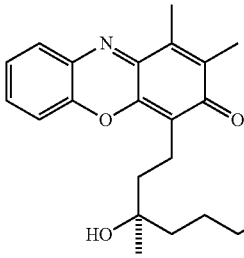

-continued

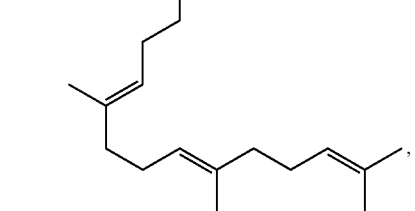

or a stereoisomer, mixture of stereoisomers, solvate, hydrate, or pharmaceutically acceptable salt thereof. In some embodiments, including any of the foregoing embodiments, the compound is selected from the group consisting of:

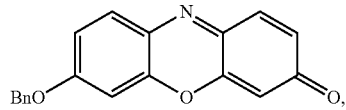
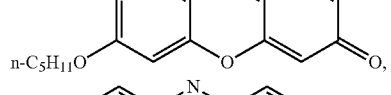
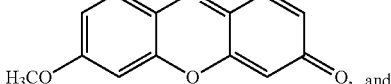
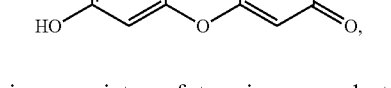

or a stereoisomer, mixture of stereoisomers, solvate, hydrate, or pharmaceutically acceptable salt thereof. In some embodiments, including any of the foregoing embodiments, the compound has an EC50 of less than about 1 micromolar, as measured by an assay described in any one of Examples 1-6. In some embodiments, including any of the foregoing embodiments, the compound has an EC50 of less than about 500 nM, as measured by an assay described in any one of Examples 1-6. In some embodiments, including any of the foregoing embodiments, the compound has an EC50 of less than about 250 nM, as measured by an assay described in any one of Examples 1-6. The method can use any individual compound of the invention as described herein, or a combination of compounds. In some embodiments, including any of the foregoing embodiments, the compound is administered as a pharmaceutical formulation comprising the compound and a pharmaceutically acceptable excipient. In some embodiments, including any of the foregoing embodiments, the method is a method of treating an oxidative stress disorder. In some embodiments, including any of the foregoing embodiments, the method is a method of suppressing an oxidative stress disorder. In some embodiments, including any of the foregoing embodiments, the oxidative stress disorder is selected from the group consisting of a mitochondrial disorder; an inherited mitochondrial disease; Alpers Disease; Barth syndrome; a Beta-oxidation Defect; Carnitine-Acyl-Carnitine Deficiency; Carnitine Deficiency; a Creatine Deficiency Syndrome; Co-Enzyme Q10 Deficiency; Complex I Deficiency; Complex II Deficiency; Complex III Deficiency; Complex IV Deficiency; Complex V Deficiency; COX Deficiency; chronic progressive external ophthalmoplegia (CPEO); CPT I Deficiency; CPT II Deficiency; Friedreich's Ataxia (FA); Glutaric Aciduria Type II; Kearns-Sayre Syndrome (KSS); Lactic Acidosis; Long-Chain Acyl-CoA Dehydrongenase Deficiency (LCAD); LCHAD; Leigh Disease; Leigh-like Syndrome; Leber's Hereditary Optic Neuropathy (LHON); Lethal Infantile Cardiomyopathy (LIC); Luft Disease; Multiple Acyl-CoA Dehydrogenase Deficiency (MAD); Medium-Chain Acyl-CoA Dehydrongenase Deficiency (MCAD); Mitochondrial Myopathy, Encephalopathy, Lactacidosis, Stroke (MELAS); Myoclonic Epilepsy with Ragged Red Fibers (MERRF); Mitochondrial Recessive Ataxia Syndrome (MIRAS); Mitochondrial Cytopathy, Mitochondrial DNA Depletion; Mitochondrial Encephalopathy; Mitochondrial Myopathy; Myoneurogastointestinal Disorder and Encephalopathy (MNGIE); Neuropathy, Ataxia, and Retinitis Pigmentosa (NARP); Pearson Syndrome; Pyruvate Carboxylase Deficiency; Pyruvate Dehydrogenase Deficiency; a POLG Mutation; a Respiratory Chain Disorder; Short-Chain Acyl-CoA Dehydrogenase Deficiency (SCAD); SCHAD; Very Long-Chain Acyl-CoA Dehydrongenase Deficiency (VLCAD); a myopathy; cardiomyopathy; encephalomyopathy; a neurodegenerative disease; Parkinson's disease; Alzheimer's disease; amyotrophic lateral sclerosis (ALS); a motor neuron disease; a neurological disease; epilepsy; an age-associated disease; macular degeneration; diabetes; metabolic syndrome; cancer; brain cancer; a genetic disease; Huntington's Disease; a mood disorder; schizophrenia; bipolar disorder; a pervasive developmental disorder; autistic disorder; Asperger's syndrome; childhood disintegrative disorder (CDD); Rett's disorder; PDD-not otherwise specified (PDD-NOS); a cerebrovascular accident; stroke; a vision impairment; optic neuropathy; dominant inherited juvenile optic atrophy; optic neuropathy caused by a toxic agent; glaucoma; Stargardt's macular dystrophy; diabetic retinopathy; diabetic maculopathy; retinopathy of prematurity; ischemic reperfusion-related retinal injury; oxygen poisoning; a haemoglobionopathy; thalassemia; sickle cell anemia; seizures; ischemia; renal tubular acidosis; attention deficit/hyperactivity disorder (ADHD); a neurodegenerative disorder resulting in hearing or balance impairment; Dominant Optic Atrophy (DOA); Maternally inherited diabetes and deafness (MIDD); chronic fatigue; contrast-induced kidney damage; contrast-induced retinopathy damage; Abetalipoproteinemia; retinitis pigmentosum; Wolfram's disease; Tourette syndrome; cobalamin c defect; methylmalonic aciduria; glioblastoma; Down's syndrome; acute tubular necrosis; a muscular dystrophy; a leukodystrophy; Progressive Supranuclear Palsy; spinal muscle atropy; hearing loss; noise induced hearing loss; and traumatic brain injury. In some embodiments, including any of the foregoing embodiments, the oxidative stress disorder is a mitochondrial disorder. In some embodiments, including any of the foregoing embodiments, the oxidative stress disorder is an inherited mitochondrial disease. In some embodiments, including any of the foregoing embodiments, the oxidative stress disorder is Friedreich's Ataxia (FA). In some embodiments, including any of the foregoing embodiments, the oxidative stress disorder is Kearns-Sayre Syndrome (KSS). In some embodiments, including any of the foregoing embodiments, the oxidative stress disorder is Leigh Disease or Leigh-like Syndrome. In some embodiments, including any of the foregoing embodiments, the oxidative stress disorder is Leber's Hereditary Optic Neuropathy (LHON). In some embodiments, including any of the foregoing embodiments, the oxidative stress disorder is Mitochondrial Myopathy, Encephalopathy, Lactacidosis, Stroke (MELAS). In some embodiments, including any of the foregoing embodiments, the oxidative stress disorder is Myoclonic Epilepsy with Ragged Red Fibers (MERRF). In some embodiments, including any of the foregoing embodiments, the oxidative stress disorder is Parkinson's disease. In some embodiments, including any of the foregoing embodiments, the oxidative stress disorder is Alzheimer's disease. In some embodiments, including any of the foregoing embodiments, the oxidative stress disorder is amyotrophic lateral sclerosis (ALS). In some embodiments, including any of the foregoing embodiments, the oxidative stress disorder is epilepsy. In some embodiments, including any of the foregoing embodiments, the oxidative stress disorder is macular degeneration. In some embodiments, including any of the foregoing embodiments, the oxidative stress disorder is brain cancer. In some embodiments, including any of the foregoing embodiments, the oxidative stress disorder is Huntington's Disease. In some embodiments, including any of the foregoing embodiments, the oxidative stress disorder is autistic disorder. In some embodiments, including any of the foregoing embodiments, the oxidative stress disorder is Rett's disorder. In some embodiments, including any of the foregoing embodiments, the oxidative stress disorder is stroke. In some embodiments, including any of the foregoing embodiments, the oxidative stress disorder is Maternally inherited diabetes and deafness (MIDD). In some embodiments, including any of the foregoing embodiments, the oxidative stress disorder is chronic fatigue. In some embodiments, including any of the foregoing embodiments, the oxidative stress disorder is contrast-induced kidney damage. In some embodiments, including any of the foregoing embodiments, the oxidative stress disorder is contrast-induced retinopathy damage. In some embodiments, including any of the foregoing embodiments, the oxidative stress disorder is cobalamin c defect. In some embodiments, including any of the foregoing embodiments, the method is a method for modulating one or more energy biomarkers, normalizing one or more energy biomarkers, or enhancing one or more energy biomarkers, wherein the one or more energy biomarkers are selected from the group consisting of: lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; total, reduced or oxidized glutathione levels, or reduced/oxidized glutathione ratio either in whole blood, plasma, lymphocytes, cerebrospinal fluid, or cerebral ventricular fluid; total, reduced or oxidized cysteine levels, or reduced/oxidized cysteine ratio either in whole blood, plasma, lymphocytes, cerebrospinal fluid, or cerebral ventricular fluid; phosphocreatine levels, NADH (NADH+H+) levels; NADPH (NADPH+H+) levels; NAD levels; NADP levels; ATP levels; reduced coenzyme Q ($CoQ_{red}$) levels; oxidized coenzyme Q ($CoQ_{ox}$) levels; total coenzyme Q ($CoQ_{tot}$) levels; oxidized cytochrome C levels; reduced cytochrome C levels; oxidized cytochrome C/reduced cytochrome C ratio; acetoacetate levels, β hydroxy butyrate levels, acetoacetate/β hydroxy butyrate ratio, 8-hydroxy-2'-deoxyguanosine (8-OHdG) levels; levels of reactive oxygen species; levels of oxygen consumption (VO2); levels of carbon dioxide output (VCO2); respiratory quotient (VCO2/VO2); exercise tolerance; and anaerobic threshold. Energy biomarkers can be measured in whole blood, plasma, cerebrospinal fluid, cerebroventricular fluid, arterial blood, venous blood, or any other body fluid, body gas, or other biological sample useful for such measurement. In some embodiments, including any of the foregoing embodiments, the levels are modulated to a value within about 2 standard deviations of the value in a healthy subject. In some embodiments, including any of the foregoing embodiments, the levels are modulated to a value within about 1 standard deviation of the value in a healthy subject. In some embodiments, including any of the foregoing embodiments, the levels in a subject are changed by at least about 10% above or below the level in the subject prior to modulation. In some embodiments, including any of the foregoing embodiments, the levels are changed by at least about 20% above or below the level in the subject prior to modulation. In some embodiments, including any of the foregoing embodiments, the levels are changed by at least about 30% above or below the level in the subject prior to modulation. In some embodiments, including any of the foregoing embodiments, the levels are changed by at least about 40% above or below the level in the subject prior to modulation. In some embodiments, including any of the foregoing embodiments, the levels are changed by at least about 50% above or below the level in the subject prior to modulation. In some embodiments, including any of the foregoing embodiments, the levels are changed by at least about 75% above or below the level in the subject prior to modulation. In some embodiments, including any of the foregoing embodiments, the levels are changed by at least about 100% above or at least about 90% below the level in the subject prior to modulation. In some embodiments, including any of the foregoing embodiments, the subject or subjects in which a method of treating or suppressing an oxidative stress disorder, modulating one or more energy biomarkers, normalizing one or more energy biomarkers, or enhancing one or more energy biomarkers is performed is/are selected from the group consisting of subjects undergoing strenuous or prolonged physical activity; subjects with chronic energy problems; subjects with chronic respiratory problems; pregnant females; pregnant females in labor; neonates; premature neonates; subjects exposed to extreme environments; subjects exposed to hot environments; subjects exposed to cold environments; subjects exposed to environments with lower-than-average oxygen content; subjects exposed to environments with higher-than-average carbon dioxide content; subjects exposed to environments with higher-than-average levels of air pollution; airline travelers; flight attendants; subjects at elevated altitudes; subjects living in cities with lower-than-average air quality; subjects working in enclosed environments where air quality is degraded; subjects with lung diseases; subjects with lower-than-average lung capacity; tubercular patients; lung cancer patients; emphysema patients; cystic fibrosis patients; subjects recovering from surgery; subjects recovering from illness; elderly subjects; elderly subjects experiencing decreased energy; subjects suffering from chronic fatigue; subjects suffering from chronic fatigue syndrome; subjects undergoing acute trauma; subjects in shock; subjects requiring acute oxygen administration; subjects requiring chronic oxygen administration; subjects requiring organ visualization via contrast solution; or other subjects with acute, chronic, or ongoing energy demands who can benefit from enhancement of energy biomarkers.

In another aspect of the invention is the use of a compound as described herein, including any of the foregoing embodiments, for treating or suppressing an oxidative stress disorder. In another aspect of the invention is the use of a compound as described herein, including any of the foregoing embodiments, in the manufacture of a medicament for use in treating or suppressing an oxidative stress disorder.

DETAILED DESCRIPTION

The invention embraces compounds useful in treating or suppressing diseases, developmental delays and symptoms related to oxidative stress such as mitochondrial disorders, impaired energy processing disorders, neurodegenerative diseases and diseases of aging, and methods of using such compounds for treating or suppressing an oxidative stress disorder, or for modulating, normalizing, or enhancing one or more (e.g. one, two, three, or more) energy biomarkers.

The abbreviations used herein have their conventional meaning within the chemical and biological arts, unless otherwise specified.

Reference to "about" a value or parameter herein includes (and describes) variations that are directed to that value or parameter per se. For example, description referring to "about X" includes description of "X".

The terms "a" or "an," as used in herein means one or more, unless context clearly dictates otherwise.

By "subject," "individual," or "patient" is meant an individual organism, preferably a vertebrate, more preferably a mammal, most preferably a human.

"Treating" a disorder with the compounds and methods discussed herein is defined as administering one or more of the compounds discussed herein, with or without additional therapeutic agents, in order to reduce or eliminate either the disorder or one or more symptoms of the disorder, or to retard the progression of the disorder or of one or more symptoms of the disorder, or to reduce the severity of the disorder or of one or more symptoms of the disorder. "Suppression" of a disorder with the compounds and methods discussed herein is defined as administering one or more of the compounds discussed herein, with or without additional therapeutic agents, in order to suppress the clinical manifestation of the disorder, or to suppress the manifestation of adverse symptoms of the disorder. The distinction between treatment and suppression is that treatment occurs after adverse symptoms of the disorder are manifest in a subject, while suppression occurs before adverse symptoms of the disorder are manifest in a subject. Suppression may be partial, substantially total, or total. Because some of the disorders are inherited, genetic screening can be used to identify patients at risk of the disorder. The compounds and methods of the invention can then be administered to asymptomatic patients at risk of developing the clinical symptoms of the disorder, in order to suppress the appearance of any adverse symptoms.

"Therapeutic use" of the compounds discussed herein is defined as using one or more of the compounds discussed herein to treat or suppress a disorder, as defined above. An "effective amount" of a compound is an amount of the compound sufficient to modulate, normalize, or enhance one or more energy biomarkers (where modulation, normalization, and enhancement are defined below). A "therapeutically effective amount" of a compound is an amount of the compound, which, when administered to a subject, is sufficient to reduce or eliminate either a disorder or one or more symptoms of a disorder, or to retard the progression of a disorder or of one or more symptoms of a disorder, or to reduce the severity of a disorder or of one or more symptoms of a disorder, or to suppress the clinical manifestation of a disorder, or to suppress the manifestation of adverse symptoms of a disorder. A therapeutically effective amount can be given in one or more administrations. An "effective amount" of a compound embraces both a therapeutically effective amount, as well as an amount effective to modulate, normalize, or enhance one or more energy biomarkers in a subject.

"Modulation" of, or to "modulate," an energy biomarker means to change the level of the energy biomarker towards a desired value, or to change the level of the energy biomarker in a desired direction (e.g., increase or decrease). Modulation can include, but is not limited to, normalization and enhancement as defined below.

"Normalization" of, or to "normalize," an energy biomarker is defined as changing the level of the energy biomarker from a pathological value towards a normal value, where the normal value of the energy biomarker can be 1) the level of the energy biomarker in a healthy person or subject, or 2) a level of the energy biomarker that alleviates one or more undesirable symptoms in the person or subject. That is, to normalize an energy biomarker which is depressed in a disease state means to increase the level of the energy biomarker towards the normal (healthy) value or towards a value which alleviates an undesirable symptom; to normalize an energy biomarker which is elevated in a disease state means to decrease the level of the energy biomarker towards the normal (healthy) value or towards a value which alleviates an undesirable symptom.

"Enhancement" of, or to "enhance," energy biomarkers means to intentionally change the level of one or more energy biomarkers away from either the normal value, or the value before enhancement, in order to achieve a beneficial or desired effect. For example, in a situation where significant energy demands are placed on a subject, it may be desirable to increase the level of ATP in that subject to a level above the normal level of ATP in that subject. Enhancement can also be of beneficial effect in a subject suffering from a disease or pathology such as e.g. a mitochondrial disorder, in that normalizing an energy biomarker may not achieve the optimum outcome for the subject; in such cases, enhancement of one or more energy biomarkers can be beneficial, for example, higher-than-normal levels of ATP, or lower-than-normal levels of lactic acid (lactate) can be beneficial to such a subject.

By modulating, normalizing, or enhancing the energy biomarker Coenzyme Q is meant modulating, normalizing, or enhancing the variant or variants of Coenzyme Q which is predominant in the species of interest. For example, the variant of Coenzyme Q which predominates in humans is Coenzyme Q10. If a species or subject has more than one variant of Coenzyme Q present in significant amounts (i.e., present in amounts which, when modulated, normalized, or enhanced, can have a beneficial effect on the species or subject), modulating, normalizing, or enhancing Coenzyme Q can refer to modulating, normalizing or enhancing any or all variants of Coenzyme Q present in the species or subject.

While the compounds described herein can occur and can be used as the neutral (non-salt) compound, the description is intended to embrace all salts of the compounds described herein, as well as methods of using such salts of the compounds. In one embodiment, the salts of the compounds comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N-dibenzylethylenediamine, and triethylamine salts. Salts of acidic compounds with amino acids, such as lysine salts, can also be prepared.

The invention also includes, if chemically possible, all stereoisomers of the compounds, including diastereomers and enantiomers. The invention also includes mixtures of possible stereoisomers in any ratio, including, but not limited to, racemic mixtures. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated.

The compounds can be administered in prodrug form. Prodrugs are derivatives of the compounds, which are themselves relatively inactive but which convert into the active compound when introduced into the subject in which they are used by a chemical or biological process in vivo, such as an enzymatic conversion. Suitable prodrug formulations include, but are not limited to, peptide conjugates of the compounds of the invention and esters of compounds of the inventions. Further discussion of suitable prodrugs is provided in H. Bundgaard, Design of Prodrugs, New York: Elsevier, 1985; in R. Silverman, The Organic Chemistry of Drug Design and Drug Action, Boston: Elsevier, 2004; in R. L. Juliano (ed.), Biological Approaches to the Controlled Delivery of Drugs (Annals of the New York Academy of Sciences, v. 507), New York: New York Academy of Sciences, 1987; and in E. B. Roche (ed.), Design of Biopharmaceutical Properties Through Prodrugs and Analogs (Symposium sponsored by Medicinal Chemistry Section, APhA Academy of Pharmaceutical Sciences, November 1976 national meeting, Orlando, Fla.), Washington: The Academy, 1977.

The description of compounds herein also includes all isotopologues, for example, partially deuterated or perdeuterated analogs of all compounds herein.

Metabolites of the compounds are also embraced by the invention.

"$(C_1-C_4)$ alkyl" is intended to embrace a saturated linear, branched, or cyclic hydrocarbon, or any combination thereof, of 1 to 4 carbon atoms. Non-limiting examples of "$(C_1-C_4)$ alkyl" include methyl, ethyl, n-propyl, isopropyl, cyclopropyl, n-butyl, isobutyl, sec-butyl, t-butyl, cyclobutyl, cyclopropyl-methyl, and methyl-cyclopropyl. The point of attachment of the $(C_1-C_4)$ alkyl group to the remainder of the molecule can be at any chemically possible location on the $(C_1-C_4)$ alkyl group.

"$(C_1-C_{12})$ alkyl" is intended to embrace a saturated linear, branched, or cyclic hydrocarbon, or any combination thereof, of 1 to 12 carbon atoms. Non-limiting examples of "$(C_1-C_{12})$ alkyl" include methyl, ethyl, n-propyl, isopropyl, cyclopropyl, n-butyl, isobutyl, sec-butyl, t-butyl, cyclobutyl, cyclopropyl-methyl, methyl-cyclopropyl, pentyl, cyclopentyl, hexyl, cyclohexyl, heptyl, octyl, nonyl, decyl, undecyl, and dodecyl. The point of attachment of the $(C_1-C_{12})$ alkyl group to the remainder of the molecule can be at any chemically possible location on the $(C_1-C_{12})$ alkyl group.

"$(C_2-C_{12})$-alkenyl" is intended to embrace an unsaturated linear, branched, or cyclic group, or any combination thereof, having 2 to 12 carbon atoms. All double bonds may be independently either (E) or (Z) geometry, as well as arbitrary mixtures thereof. Examples of alkenyl groups include, but are not limited to —CH2-CH=CH—CH3; and —CH2-CH2-cyclohexenyl, where the ethyl group can be attached to the cyclohexenyl moiety at any available carbon valence.

"$(C_2-C_{12})$-alkynyl" is intended to embrace an unsaturated linear, branched, or cyclic group, or any combination thereof, having 2 to 12 carbon atoms, which contain at least one triple bond.

"Halogen" or "halo" designates fluoro, chloro, bromo, and iodo.

"$(C_1-C_4)$ haloalkyl" is intended to embrace any $C_1-C_4$ alkyl substituent having at least one halogen substituent; the halogen can be attached via any valence on the $C_1-C_4$ alkyl group. Some examples of $C_1-C_4$ haloalkyl are —$CF_3$, —$CCl_3$, —$CHF_2$, —$CHCl_2$, —$CHBr_2$, —$CH_2F$, —$CH_2Cl$, or —$CF_2CF_3$.

"$(C_1-C_{12})$ haloalkyl" is intended to embrace any $C_1-C_{12}$ alkyl substituent having at least one halogen substituent; the halogen can be attached via any valence on the $C_1-C_{12}$ alkyl group. Some examples of $C_1-C_{12}$ haloalkyl are —$CF_3$, —$CCl_3$, —$CHF_2$, —$CHCl_2$, —$CHBr_2$, —$CH_2F$, —$CH_2Cl$, or —$CF_2CF_3$.

The term "aryl" is intended to embrace an aromatic cyclic hydrocarbon group of from 6 to 10 carbon atoms having a single ring (e.g., phenyl) or multiple condensed (fused) rings (e.g., naphthyl).

By "respiratory chain disorder" is meant a disorder which results in the decreased utilization of oxygen by a mitochondrion, cell, tissue, or individual, due to a defect or disorder in a protein or other component contained in the mitochondrial respiratory chain. By "protein or other component contained in the mitochondrial respiratory chain" is meant the components (including, but not limited to, proteins, tetrapyrroles, and cytochromes) comprising mitochondrial complex I, II, III, IV, and/or V. "Respiratory chain protein" refers to the protein components of those complexes, and "respiratory chain protein disorder" is meant a disorder which results in the decreased utilization of oxygen by a mitochondrion, cell, tissue, or individual, due to a defect or disorder in a protein contained in the mitochondrial respiratory chain.

The terms "Parkinson's", (also called "Parkinsonism" and "Parkinsonian syndrome") ("PD") is intended to include not only Parkinson's disease but also drug-induced Parkinsonism and post-encephalitic Parkinsonism. Parkinson's disease is also known as paralysis agitans or shaking palsy. It is characterized by tremor, muscular rigidity and loss of postural reflexes. The disease usually progresses slowly with intervals of 10 to 20 years elapsing before the symptoms cause incapacity. Due to their mimicry of effects of Parkinson's disease, treatment of animals with methamphetamine or MPTP has been used to generate models for Parkinson's disease. These animal models have been used to evaluate the efficacy of various therapies for Parkinson's disease.

The term "Friedreich's ataxia" is intended to embrace other related ataxias, and is also sometimes referred to as hereditary ataxia, familial ataxia, or Friedreich's tabes.

The term "ataxia" is an aspecific clinical manifestation implying dysfunction of parts of the nervous system that coordinate movement, such as the cerebellum. People with ataxia have problems with coordination because parts of the nervous system that control movement and balance are affected. Ataxia may affect the fingers, hands, arms, legs, body, speech, and eye movements. The word ataxia is often used to describe a symptom of incoordination which can be associated with infections, injuries, other diseases, or degenerative changes in the central nervous system. Ataxia is also used to denote a group of specific degenerative diseases of the nervous system called the hereditary and sporadic ataxias. Ataxias are also often associated with hearing impairments.

There are three types of ataxia, cerebellar ataxia, including vestibulo-cerebellar dysfunction, spino-cerebellar dysfunction, and cerebro-cerebellar dysfunction; sensory ataxia; and vestibular ataxia. Examples of the diseases which are classifiable into spino-cerebellar ataxia or multiple system atrophy are hereditary olivo-ponto-cerebellar atrophy, hereditary cerebellar cortical atrophy, Friedreich's ataxia, Machado-Joseph diseases, Ramsay Hunt syndrome, hereditary dentatorubral-pallidoluysian atrophy, hereditary spastic paraplegia, Shy-Drager syndrome, cortical cerebellar atrophy, striato-nigral degeneration, Marinesco-Sjogren syndrome, alcoholic cortical cerebellar atrophy, paraneoplastic cerebellar atrophy associated with malignant tumor, toxic cerebellar atrophy caused by toxic substances, Vitamin E deficiency due to mutation of a Tocopherol transfer protein (aTTP) or lipid absorption disorder such as Abetalipoproteinemia, cerebellar atrophy associated with endocrine disturbance and the like.

Examples of ataxia symptoms are motor ataxia, trunk ataxia, limb ataxia and the like, autonomic disturbance such as orthostatic hypotension, dysuria, hypohidrosis, sleep apnea, orthostatic syncope and the like, stiffness of lower extremity, ocular nystagmus, oculomotor nerve disorder, pyramidal tract dysfunction, extrapyramidal symptoms (postural adjustment dysfunction, muscular rigidity, akinesia, tremors), dysphagia, lingual atrophy, posterior funiculus symptom, muscle atrophy, muscle weakness, deep hyperreflexia, sensory disturbance, scoliosis, kyphoscoliosis, foot deformities, anarthria, dementia, manic state, decreased motivation for rehabilitation and the like.

Diseases Amenable to Treatment or Suppression with Compounds and Methods of the Invention A variety of disorders/diseases are believed to be caused or aggravated by oxidative stress affecting normal electron flow in the cells, such as mitochondrial disorders, impaired energy processing disorders, neurodegenerative diseases and diseases of aging, and can be treated or suppressed using the compounds and methods of the invention.

Non-limiting examples of oxidative stress disorders include, for example, mitochondrial disorders (including inherited mitochondrial diseases) such as Alpers Disease, Barth syndrome, Beta-oxidation Defects, Carnitine-Acyl-Carnitine Deficiency, Carnitine Deficiency, Creatine Deficiency Syndromes, Co-Enzyme Q10 Deficiency, Complex I Deficiency, Complex II Deficiency, Complex III Deficiency, Complex IV Deficiency, Complex V Deficiency, COX Deficiency, chronic progressive external ophthalmoplegia (CPEO), CPT I Deficiency, CPT II Deficiency, Friedreich's Ataxia (FA), Glutaric Aciduria Type II, Kearns-Sayre Syndrome (KSS), Lactic Acidosis, Long-Chain Acyl-CoA Dehydrongenase Deficiency (LCAD), LCHAD, Leigh Disease or Syndrome, Leigh-like Syndrome, Leber's Hereditary Optic Neuropathy (LHON, also referred to as Leber's Disease, Leber's Optic Atrophy (LOA), or Leber's Optic Neuropathy (LON)), Lethal Infantile Cardiomyopathy (LIC), Luft Disease, Multiple Acyl-CoA Dehydrogenase Deficiency (MAD), Medium-Chain Acyl-CoA Dehydrongenase Deficiency (MCAD), Mitochondrial Myopathy, Encephalopathy, Lactacidosis, Stroke (MELAS), Myoclonic Epilepsy with Ragged Red Fibers (MERRF), Mitochondrial Recessive Ataxia Syndrome (MIRAS), Mitochondrial Cytopathy, Mitochondrial DNA Depletion, Mitochondrial Encephalopathy, Mitochondrial Myopathy, Myoneurogastointestinal Disorder and Encephalopathy (MNGIE), Neuropathy, Ataxia, and Retinitis Pigmentosa (NARP), Pearson Syndrome, Pyruvate Carboxylase Deficiency, Pyruvate Dehydrogenase Deficiency, POLG Mutations, Respiratory Chain Disorder, Short-Chain Acyl-CoA Dehydrogenase Deficiency (SCAD), SCHAD, Very Long-Chain Acyl-CoA Dehydrongenase Deficiency (VLCAD); myopathies such as cardiomyopathy and encephalomyopathy; neurodegenerative diseases such as Parkinson's disease, Alzheimer's disease, and amyotrophic lateral sclerosis (ALS, also known as Lou Gehrig's disease); motor neuron diseases; neurological diseases such as epilepsy; age-associated diseases, particularly diseases for which CoQ10 has been proposed for treatment, such as macular degeneration, diabetes, metabolic syndrome, and cancer (e.g. brain cancer); genetic diseases such as Huntington's Disease (which is also a neurological disease); mood disorders such as schizophrenia and bipolar disorder; pervasive developmental disorders such as autistic disorder, Asperger's syndrome, childhood disintegrative disorder (CDD), Rett's disorder, and PDD-not otherwise specified (PDD-NOS); cerebrovascular accidents such as stroke; vision impairments such as those caused by neurodegenerative diseases of the eye such as optic neuropathy, Leber's hereditary optic neuropathy, dominant inherited juvenile optic atrophy, optic neuropathy caused by toxic agents, glaucoma, age-related macular degeneration (both "dry" or non-exudative macular degeneration and "wet" or exudative macular degeneration), Stargardt's macular dystrophy, diabetic retinopathy, diabetic maculopathy, retinopathy of prematurity, or ischemic reperfusion-related retinal injury; disorders caused by energy impairment include diseases due to deprivation, poisoning or toxicity of oxygen, and qualitative or quantitative disruption in the transport of oxygen such as haemoglobionopathies, for example thalassemia or sickle cell anemia; other diseases in which mitochondrial dysfunction is implicated such as excitoxic, neuronal injury, such as that associated with seizures, stroke and ischemia; and other disorders including renal tubular acidosis; attention deficit/hyperactivity disorder (ADHD); neurodegenerative disorders resulting in hearing or balance impairment; Dominant Optic Atrophy (DOA); Maternally inherited diabetes and deafness (MIDD); chronic fatigue; contrast-induced kidney damage; contrast-induced retinopathy damage; Abetalipoproteinemia; retinitis pigmentosum; Wolfram's disease; Tourette syndrome; cobalamin c defect; methylmalonic aciduria; glioblastoma; Down's syndrome; acute tubular necrosis; muscular dystrophies; leukodystrophies; Progressive Supranuclear Palsy; spinal muscle atropy; hearing loss (e.g. noise induced hearing loss); and traumatic brain injury.

For some disorders amenable to treatment with compounds and methods of the invention, the primary cause of the disorder is due to a defect in the respiratory chain or another defect preventing normal utilization of energy in mitochondria, cells, or tissue(s). Non-limiting examples of disorders falling in this category include inherited mitochondrial diseases, such as Myoclonic Epilepsy with Ragged Red Fibers (MERRF), Mitochondrial Myopathy, Encephalopathy, Lactacidosis, and Stroke (MELAS), Leber's Hereditary Optic Neuropathy (LHON, also referred to as Leber's Disease, Leber's Optic Atrophy (LOA), or Leber's Optic Neuropathy (LON)), Leigh Disease or Leigh Syndrome, Kearns-Sayre Syndrome (KSS), and Friedreich's Ataxia (FA). For some disorders amenable to treatment with compounds and methods of the invention, the primary cause of the disorder is not due to respiratory chain defects or other defects preventing normal utilization of energy in mitochondria, cells, or tissue(s); non-limiting examples of disorders falling in this category include stroke, cancer, and diabetes. However, these latter disorders are particularly aggravated by energy impairments, and are particularly amenable to treatment with compounds of the invention in order to ameliorate the condition. Pertinent examples of such disorders include ischemic stroke and hemorrhagic stroke, where the primary cause of the disorder is due to impaired blood supply to the brain. While an ischemic episode caused by a thrombosis or embolism, or a hemorrhagic episode caused by a ruptured blood vessel, is not primarily caused by a defect in the respiratory chain or another metabolic defect preventing normal utilization of energy, oxidative stress plays a role in the ischemic cascade due to oxygen reperfusion injury following hypoxia (this cascade occurs in heart attacks as well as in strokes). Accordingly, treatment with compounds and methods of the invention will mitigate the effects of the disease, disorder or condition. Modulating one or more energy biomarkers, normalizing one or more energy biomarkers, or enhancing one or more energy biomarkers can also prove beneficial in such disorders both as a therapeutic measure and a prophylactic measure. For example, for a patient scheduled to undergo non-emergency repair of an aneurysm, enhancing energy biomarkers before and during the pre-operative can improve the patient's prognosis should the aneurysm rupture before successful repair.

The term "oxidative stress disorder" or "oxidative stress disease" encompass both diseases caused by oxidative stress and diseases aggravated by oxidative stress. The terms "oxidative stress disorder" or "oxidative stress disease" encompass both diseases and disorders where the primary cause of the disease is due to a defect in the respiratory chain or another defect preventing normal utilization of energy in mitochondria, cells, or tissue(s), and also diseases and disorders where the primary cause of the disease is not due to a defect in the respiratory chain or another defect preventing normal utilization of energy in mitochondria, cells, or tissue(s). The former set of diseases can be referred to as "primary oxidative stress disorders," while the latter can be referred to as "secondary oxidative stress disorders." It should be noted that the distinction between "diseases caused by oxidative stress" and "diseases aggravated by oxidative stress" is not absolute; a disease may be both a disease caused by oxidative stress and a disease aggravated by oxidative stress. The boundary between "primary oxidative stress disorder" and a "secondary oxidative stress disorder" is more distinct, provided that there is only one primary cause of a disease or disorder and that primary cause is known.

Bearing in mind the somewhat fluid boundary between diseases caused by oxidative stress and diseases aggravated by oxidative stress, mitochondrial diseases or disorders and impaired energy processing diseases and disorders tend to fall into the category of diseases caused by oxidative stress, while neurodegenerative disorders and diseases of aging tend to fall into the category of diseases aggravated by oxidative stress. Mitochondrial diseases or disorders and impaired energy processing diseases and disorders are generally primary oxidative stress disorders, while neurodegenerative disorders and diseases of aging may be primary or secondary oxidative stress disorders "Disorder" and "disease" are used interchangeably herein.

Clinical Assessment of Oxidative Stress and Efficacy of Therapy

Several readily measurable clinical markers are used to assess the metabolic state of patients with oxidative stress disorders. These markers can also be used as indicators of the efficacy of a given therapy, as the level of a marker is moved from the pathological value to the healthy value. These clinical markers include, but are not limited to, energy biomarkers such as lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; total, reduced or oxidized glutathione levels, or reduced/oxidized glutathione ratio either in whole blood, plasma, lymphocytes, cerebrospinal fluid, or cerebral ventricular fluid; total, reduced or oxidized cysteine levels, or reduced/oxidized cysteine ratio either in whole blood, plasma, lymphocytes, cerebrospinal fluid, or cerebral ventricular fluid; phosphocreatine levels, NADH (NADH+ H+) or NADPH (NADPH+H+) levels; NAD or NADP levels; ATP levels; anaerobic threshold; reduced coenzyme Q (Co-$Q_{red}$) levels; oxidized coenzyme Q (Co$Q_{ox}$) levels; total coenzyme Q (Co$Q_{tot}$) levels; oxidized cytochrome C levels; reduced cytochrome C levels; oxidized cytochrome C/reduced cytochrome C ratio; acetoacetate levels, β-hydroxy butyrate levels, acetoacetate/β-hydroxy butyrate ratio, 8-hydroxy-2'-deoxyguanosine (8-OHdG) levels; levels of reactive oxygen species; and levels of oxygen consumption (VO2), levels of carbon dioxide output (VCO2), and respiratory quotient (VCO2/VO2). Several of these clinical markers are measured routinely in exercise physiology laboratories, and provide convenient assessments of the metabolic state of a subject. In one embodiment of the invention, the level of one or more energy biomarkers in a patient suffering from an oxidative stress disorder, such as Friedreich's ataxia, Leber's hereditary optic neuropathy, MELAS, KSS or CoQ10 deficiency, is improved to within two standard deviations of the average level in a healthy subject. In another embodiment of the invention, the level of one or more of these energy biomarkers in a patient suffering from an oxidative stress disorder, such as Friedreich's ataxia, Leber's hereditary optic neuropathy, MELAS, KSS or CoQ10 deficiency is improved to within one standard deviation of the average level in a healthy subject. Exercise intolerance can also be used as an indicator of the efficacy of a given therapy, where an improvement in exercise tolerance (i.e., a decrease in exercise intolerance) indicates efficacy of a given therapy.

Several metabolic biomarkers have already been used to evaluate efficacy of CoQ10, and these metabolic biomarkers can be monitored as energy biomarkers for use in the methods of the current invention. Lactate, a product of the anaerobic metabolism of glucose, is removed by reduction to pyruvate in an aerobic setting or by oxidative metabolism, which is dependent on a functional mitochondrial respiratory chain. Dysfunction of the respiratory chain may lead to inadequate removal of lactate and pyruvate from the circulation and elevated lactate/pyruvate ratios are observed in mitochondrial cytopathies (see Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)). Blood lactate/pyruvate ratio (Chariot et al., Arch. Pathol. Lab. Med. 118(7): 695-7 (1994)) is, therefore, widely used as a noninvasive test for detection of mitochondrial cytopathies (see again Scriver CR, The metabolic and molecular bases of inherited disease, 7th ed., New York: McGraw-Hill, Health Professions Division, 1995; and Munnich et al., J. Inherit. Metab. Dis. 15(4): 448-55 (1992)) and toxic mitochondrial myopathies (Chariot et al., Arthritis Rheum. 37(4):583-6 (1994)). Changes in the redox state of liver mitochondria can be investigated by measuring the arterial ketone body ratio (acetoacetate/3-hydroxybutyrate: AKBR) (Ueda et al., J. Cardiol. 29(2):95-102 (1997)). Urinary excretion of 8-hydroxy-2'-deoxyguanosine (8-OHdG) often has been used as a biomarker to assess the extent of repair of ROS-induced DNA damage in both clinical and occupational settings (Erhola et al., FEBS Lett. 409(2): 287-91 (1997); Honda et al., Leuk. Res. 24(6):461-8 (2000); Pilger et al., Free Radic. Res. 35(3):273-80 (2001); Kim et al. Environ Health Perspect 112(6):666-71 (2004)).

Magnetic resonance spectroscopy (MRS) has been useful in the diagnoses of mitochondrial cytopathy by demonstrating elevations in cerebrospinal fluid (CSF) and cortical white matter lactate using proton MRS (1H-MRS) (Kaufmann et al., Neurology 62(8):1297-302 (2004)). Phosphorous MRS (31P-MRS) has been used to demonstrate low levels of cortical phosphocreatine (PCr) (Matthews et al., Ann. Neurol. 29(4):435-8 (1991)), and a delay in PCr recovery kinetics following exercise in skeletal muscle (Matthews et al., Ann. Neurol. 29(4):435-8 (1991); Barbiroli et al., J. Neurol. 242 (7):472-7 (1995); Fabrizi et al., J. Neurol. Sci. 137(1):20-7 (1996)). A low skeletal muscle PCr has also been confirmed in patients with mitochondrial cytopathy by direct biochemical measurements.

Exercise testing is particularly helpful as an evaluation and screening tool in mitochondrial myopathies. One of the hallmark characteristics of mitochondrial myopathies is a reduction in maximal whole body oxygen consumption (VO2max) (Taivassalo et al., Brain 126(Pt 2):413-23 (2003)). Given that VO2max is determined by cardiac output (Qc) and peripheral oxygen extraction (arterial-venous total oxygen content) difference, some mitochondrial cytopathies affect cardiac function where delivery can be altered; however, most mitochondrial myopathies show a characteristic deficit in peripheral oxygen extraction (A-V O2 difference) and an enhanced oxygen delivery (hyperkinetic circulation) (Taivassalo et al., Brain 126(Pt 2):413-23 (2003)). This can be demonstrated by a lack of exercise induced deoxygenation of venous blood with direct AV balance measurements (Taivassalo et al., Ann. Neurol. 51(1):38-44 (2002)) and non-invasively by near infrared spectroscopy (Lynch et al., Muscle Nerve 25(5):664-73 (2002); van Beekvelt et al., Ann. Neurol. 46(4):667-70 (1999)).

Several of these energy biomarkers are discussed in more detail as follows. It should be emphasized that, while certain energy biomarkers are discussed and enumerated herein, the invention is not limited to modulation, normalization or enhancement of only these enumerated energy biomarkers.

Lactic acid (lactate) levels: Mitochondrial dysfunction typically results in abnormal levels of lactic acid, as pyruvate levels increase and pyruvate is converted to lactate to maintain capacity for glycolysis. Mitochondrial dysfunction can also result in abnormal levels of NADH+H+, NADPH+H+, NAD, or NADP, as the reduced nicotinamide adenine dinucleotides are not efficiently processed by the respiratory chain. Lactate levels can be measured by taking samples of appropriate bodily fluids such as whole blood, plasma, or cerebrospinal fluid. Using magnetic resonance, lactate levels can be measured in virtually any volume of the body desired, such as the brain.

Measurement of cerebral lactic acidosis using magnetic resonance in MELAS patients is described in Kaufmann et al., Neurology 62(8):1297 (2004). Values of the levels of lactic acid in the lateral ventricles of the brain are presented for two mutations resulting in MELAS, A3243G and A8344G. Whole blood, plasma, and cerebrospinal fluid lactate levels can be measured by commercially available equipment such as the YSI 2300 STAT Plus Glucose & Lactate Analyzer (YSI Life Sciences, Ohio).

NAD, NADP, NADH and NADPH levels: Measurement of NAD, NADP, NADH (NADH+H+) or NADPH (NADPH+H+) can be measured by a variety of fluorescent, enzymatic, or electrochemical techniques, e.g., the electrochemical assay described in US 2005/0067303.

GSH, GSSG, Cys, and CySS levels: Briefly, plasma levels of GSH, GSSG, Cys, and CySS are used to calculate the in vivo $E_h$ values. Samples are collected using the procedure of Jones et al (2009 Free Radical Biology & Medicine 47(10) pp 1329-1338), and bromobimane is used to alkylate free thiols and HPLC and either electrochemical or MSMS to separate, detect, and quantify the molecules. As described in more detail in U.S. Provisional Patent Application No. 61/698,431 filed Sep. 7, 2012, and U.S. Provisional Patent Application 61/792,797 filed Mar. 15, 2013, a method was developed for different experimental parameters to analyze the most common monothiols and disulfide (cystine, cysteine, reduced (GSH) and oxidized glutathione (GSSG)) present in human plasma, and using Bathophenanthroline disulfonic acid as the internal standard (IS). Complete separation of all the targets analytes and IS at 35.0 on a C18 RP column (250 mm×4.6 mm, 3 micron) was achieved using 0.2% TFA:Acetonitrile as a mobile phase pumped at the rate of 0.6 ml min-1 using electrochemical detector in DC mode at the detector potential of 1475 mV.

Oxygen consumption (vO2 or VO2), carbon dioxide output (vCO2 or VCO2), and respiratory quotient (VCO2/VO2): vO2 is usually measured either while resting (resting vO2) or at maximal exercise intensity (vO2 max). Optimally, both values will be measured. However, for severely disabled patients, measurement of vO2 max may be impractical. Measurement of both forms of vO2 is readily accomplished using standard equipment from a variety of vendors, e.g. Korr Medical Technologies, Inc. (Salt Lake City, Utah). VCO2 can also be readily measured, and the ratio of VCO2 to VO2 under the same conditions (VCO2/VO2, either resting or at maximal exercise intensity) provides the respiratory quotient (RQ).

Oxidized Cytochrome C, reduced Cytochrome C, and ratio of oxidized Cytochrome C to reduced Cytochrome C: Cytochrome C parameters, such as oxidized cytochrome C levels (Cyt $C_{ox}$), reduced cytochrome C levels (Cyt $C_{red}$), and the ratio of oxidized cytochrome C/reduced cytochrome C ratio (Cyt $C_{ox}$)/(Cyt $C_{red}$), can be measured by in vivo near infrared spectroscopy. See, e.g., Rolfe, P., "In vivo near-infrared spectroscopy," Annu. Rev. Biomed. Eng. 2:715-54 (2000) and Strangman et al., "Non-invasive neuroimaging using near-infrared light" Biol. Psychiatry 52:679-93 (2002).

Exercise tolerance/Exercise intolerance: Exercise intolerance is defined as "the reduced ability to perform activities that involve dynamic movement of large skeletal muscles because of symptoms of dyspnea or fatigue" (Piñ a et al., Circulation 107:1210 (2003)). Exercise intolerance is often accompanied by myoglobinuria, due to breakdown of muscle tissue and subsequent excretion of muscle myoglobin in the urine. Various measures of exercise intolerance can be used, such as time spent walking or running on a treadmill before exhaustion, time spent on an exercise bicycle (stationary bicycle) before exhaustion, and the like. Treatment with the compounds or methods of the invention can result in about a 10% or greater improvement in exercise tolerance (for example, about a 10% or greater increase in time to exhaustion, e.g. from 10 minutes to 11 minutes), about a 20% or greater improvement in exercise tolerance, about a 30% or greater improvement in exercise tolerance, about a 40% or greater improvement in exercise tolerance, about a 50% or greater improvement in exercise tolerance, about a 75% or greater improvement in exercise tolerance, or about a 100% or greater improvement in exercise tolerance. While exercise tolerance is not, strictly speaking, an energy biomarker, for the purposes of the invention, modulation, normalization, or enhancement of energy biomarkers includes modulation, normalization, or enhancement of exercise tolerance.

Similarly, tests for normal and abnormal values of pyruvic acid (pyruvate) levels, lactate/pyruvate ratio, ATP levels, anaerobic threshold, reduced coenzyme Q (CoQ$_{red}$ levels, oxidized coenzyme Q (CoQ$_{ox}$) levels, total coenzyme Q (CoQ$_{tot}$) levels, oxidized cytochrome C levels, reduced cytochrome C levels, oxidized cytochrome C/reduced cytochrome C ratio, GSH and cysteine reduced, oxidized, total levels and ratio, acetoacetate levels, β-hydroxy butyrate levels, acetoacetate/β-hydroxy butyrate ratio, 8-hydroxy-2'-deoxyguanosine (8-OHdG) levels, and levels of reactive oxygen species are known in the art and can be used to evaluate efficacy of the compounds and methods of the invention. (For the purposes of the invention, modulation, normalization, or enhancement of energy biomarkers includes modulation, normalization, or enhancement of anaerobic threshold.)

Table 1, following, illustrates the effect that various dysfunctions can have on biochemistry and energy biomarkers. It also indicates the physical effect (such as a disease symptom or other effect of the dysfunction) typically associated with a given dysfunction. It should be noted that any of the energy biomarkers listed in the table, in addition to energy biomarkers enumerated elsewhere, can also be modulated, enhanced, or normalized by the compounds and methods of the invention. RQ=respiratory quotient; BMR=basal metabolic rate; HR (CO)=heart rate (cardiac output); T=body temperature (preferably measured as core temperature); AT=anaerobic threshold; pH=blood pH (venous and/or arterial).

TABLE 1

| Site of Dysfunction | Biochemical Event | Measurable Energy Biomarker | Physical Effect |
|---|---|---|---|
| Respiratory Chain | ↑ NADH | Δ lactate, Δ lactate:pyruvate ratio; and Δ acetoacetate:β-hydroxy butyrate ratio | Metabolic dyscrasia & fatigue |
| Respiratory Chain | ↓ H+ gradient | Δ ATP | Organ dependent dysfunction |
| Respiratory Chain | ↓ Electron flux | Δ VO2, RQ, BMR, ΔT, AT, pH | Metabolic dyscrasia & fatigue |
| Mitochondria & cytosol | ↓ ATP, ↓ VO2 | Δ Work, ΔHR (CO) | Exercise intolerance |
| Mitochondria & cytosol | ↓ ATP | Δ PCr | Exercise intolerance |
| Respiratory Chain | ↓ Cyt $C_{Ox}/_{Red}$ | Δ λ ~700-900 nm (Near Infrared Spectroscopy) | Exercise intolerance |
| Intermediary metabolism | ↓ Catabolism | Δ C14-Labeled substrates | Metabolic dyscrasia & fatigue |
| Respiratory Chain | ↓ Electron flux | Δ Mixed Venous VO2 | Metabolic dyscrasia & fatigue |
| Mitochondria & cytosol | ↑ Oxidative stress | Δ Tocopherol & Tocotrienols, CoQ10, docosahexaenoic acid | Uncertain |
| Mitochondria & cytosol | ↑ Oxidative stress | Δ Glutathionered | Uncertain |
| Mitochondria & cytosol | Nucleic acid oxidation | Δ8-hydroxy 2-deoxy guanosine | Uncertain |
| Mitochondria & cytosol | Lipid oxidation | Δ Isoprostane(s), eicosanoids | Uncertain |
| Cell membranes | Lipid oxidation | Δ Ethane (breath) | Uncertain |
| Cell membranes | Lipid oxidation | Δ Malondialdehyde | Uncertain |

Treatment of a subject afflicted by an oxidative stress disorder in accordance with the methods of the invention may result in the inducement of a reduction or alleviation of symptoms in the subject, e.g., to halt the further progression of the disorder.

Partial or complete suppression of the oxidative stress disorder can result in a lessening of the severity of one or more of the symptoms that the subject would otherwise experience. For example, partial suppression of MELAS could result in reduction in the number of stroke-like or seizure episodes suffered.

Any one or any combination of the energy biomarkers described herein provide conveniently measurable benchmarks by which to gauge the effectiveness of treatment or suppressive therapy. Additionally, other energy biomarkers are known to those skilled in the art and can be monitored to evaluate the efficacy of treatment or suppressive therapy.

Use of Compounds for Modulation of Energy Biomarkers

In addition to monitoring energy biomarkers to assess the status of treatment or suppression of oxidative stress diseases, the compounds of the invention can be used in subjects or patients to modulate one or more energy biomarkers. Modulation of energy biomarkers can be done to normalize energy biomarkers in a subject, or to enhance energy biomarkers in a subject.

Normalization of one or more energy biomarkers is defined as either restoring the level of one or more such energy biomarkers to normal or near-normal levels in a subject whose levels of one or more energy biomarkers show pathological differences from normal levels (i.e., levels in a healthy subject), or to change the levels of one or more energy biomarkers to alleviate pathological symptoms in a subject. Depending on the nature of the energy biomarker, such levels may show measured values either above or below a normal value. For example, a pathological lactate level is typically higher than the lactate level in a normal (i.e., healthy) person, and a decrease in the level may be desirable. A pathological ATP level is typically lower than the ATP level in a normal (i.e., healthy) person, and an increase in the level of ATP may be desirable. Accordingly, normalization of energy biomarkers can involve restoring the level of energy biomarkers to within about at least two standard deviations of normal in a subject, more preferably to within about at least one standard deviation of normal in a subject, to within about at least one-half standard deviation of normal, or to within about at least one-quarter standard deviation of normal.

Enhancement of the level of one or more energy biomarkers is defined as changing the extant levels of one or more energy biomarkers in a subject to a level which provides beneficial or desired effects for the subject. For example, a person undergoing strenuous effort or prolonged vigorous physical activity, such as mountain climbing, could benefit from increased ATP levels or decreased lactate levels. As described above, normalization of energy biomarkers may not achieve the optimum state for a subject with an oxidative stress disease, and such subjects can also benefit from enhancement of energy biomarkers. Examples of subjects who could benefit from enhanced levels of one or more energy biomarkers include, but are not limited to, subjects undergoing strenuous or prolonged physical activity, subjects with chronic energy problems, or subjects with chronic respiratory problems. Such subjects include, but are not limited to, pregnant females, particularly pregnant females in labor; neonates, particularly premature neonates; subjects exposed to extreme environments, such as hot environments (temperatures routinely exceeding about 85-86 degrees Fahrenheit or about 30 degrees Celsius for about 4 hours daily or more), cold environments (temperatures routinely below about 32 degrees Fahrenheit or about 0 degrees Celsius for about 4 hours daily or more), or environments with lower-than-average oxygen content, higher-than-average carbon dioxide content, or higher-than-average levels of air pollution (airline travelers, flight attendants, subjects at elevated altitudes, subjects living in cities with lower-than-average air quality, subjects working in enclosed environments where air quality is degraded); subjects with lung diseases or lower-than-average lung capacity, such as tubercular patients, lung cancer patients, emphysema patients, and cystic fibrosis patients; subjects recovering from surgery or illness; elderly subjects, including elderly subjects experiencing decreased energy; subjects suffering from chronic fatigue, including chronic fatigue syndrome; subjects undergoing acute trauma; subjects in shock; subjects requiring acute oxygen administration; subjects requiring chronic oxygen administration; or other subjects with acute, chronic, or ongoing energy demands who can benefit from enhancement of energy biomarkers.

Accordingly, when an increase in a level of one or more energy biomarkers is beneficial to a subject, enhancement of the one or more energy biomarkers can involve increasing the level of the respective energy biomarker or energy biomarkers to about at least one-quarter standard deviation above normal, about at least one-half standard deviation above normal, about at least one standard deviation above normal, or about at least two standard deviations above normal. Alternatively, the level of the one or more energy biomarkers can be increased by about at least 10% above the subject's level of the respective one or more energy biomarkers before enhancement, by about at least 20% above the subject's level of the respective one or more energy biomarkers before enhancement, by about at least 30% above the subject's level of the respective one or more energy biomarkers before enhancement, by about at least 40% above the subject's level of the respective one or more energy biomarkers before enhancement, by about at least 50% above the subject's level of the respective one or more energy biomarkers before enhancement, by about at least 75% above the subject's level of the respective one or more energy biomarkers before enhancement, or by about at least 100% above the subject's level of the respective one or more energy biomarkers before enhancement.

When a decrease in a level of one or more energy biomarkers is desired to enhance one or more energy biomarkers, the level of the one or more energy biomarkers can be decreased by an amount of about at least one-quarter standard deviation of normal in a subject, decreased by about at least one-half standard deviation of normal in a subject, decreased by about at least one standard deviation of normal in a subject, or decreased by about at least two standard deviations of normal in a subject. Alternatively, the level of the one or more energy biomarkers can be decreased by about at least 10% below the subject's level of the respective one or more energy biomarkers before enhancement, by about at least 20% below the subject's level of the respective one or more energy biomarkers before enhancement, by about at least 30% below the subject's level of the respective one or more energy biomarkers before enhancement, by about at least 40% below the subject's level of the respective one or more energy biomarkers before enhancement, by about at least 50% below the subject's level of the respective one or more energy biomarkers before enhancement, by about at least 75% below the subject's level of the respective one or more energy biomarkers before enhancement, or by about at least 90% below the subject's level of the respective one or more energy biomarkers before enhancement.

Use of Compounds in Research Applications, Experimental Systems, and Assays

The compounds of the invention can also be used in research applications. They can be used in in vitro, in vivo, or ex vivo experiments to modulate one or more energy biomarkers in an experimental system. Such experimental systems can be cell samples, tissue samples, cell components or mixtures of cell components, partial organs, whole organs, or organisms. Any one or more of the compounds of formula I can be used in experimental systems or research applications. Such research applications can include, but are not limited to, use as assay reagents, elucidation of biochemical pathways, or evaluation of the effects of other agents on the metabolic state of the experimental system in the presence/absence of one or more compounds of the invention.

Additionally, the compounds of the invention can be used in biochemical tests or assays. Such tests can include incubation of one or more compounds of the invention with a tissue or cell sample from a subject to evaluate a subject's potential response (or the response of a specific subset of subjects) to administration of said one or more compounds, or to determine which compound of the invention produces the optimum effect in a specific subject or subset of subjects. One such test or assay would involve 1) obtaining a cell sample or tissue sample from a subject in which modulation of one or more energy biomarkers can be assayed; 2) administering one or more compounds of the invention to the cell sample or tissue sample; and 3) determining the amount of modulation of the one or more energy biomarkers after administration of the one or more compounds, compared to the status of the energy biomarker prior to administration of the one or more compounds. Another such test or assay would involve 1) obtaining a cell sample or tissue sample from a subject in which modulation of one or more energy biomarkers can be assayed; 2) administering at least two compounds of the invention to the cell sample or tissue sample; 3) determining the amount of modulation of the one or more energy biomarkers after administration of the at least two compounds, compared to the status of the energy biomarker prior to administration of the at least two compounds, and 4) selecting a compound or compounds for use in treatment, suppression, or modulation based on the amount of modulation determined in step 3.

Pharmaceutical Formulations

The compounds described herein can be formulated as pharmaceutical compositions by formulation with additives such as pharmaceutically acceptable excipients, pharmaceutically acceptable carriers, and pharmaceutically acceptable vehicles. Suitable pharmaceutically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference.

A pharmaceutical composition can comprise a unit dose formulation, where the unit dose is a dose sufficient to have a therapeutic or suppressive effect or an amount effective to modulate, normalize, or enhance an energy biomarker. The unit dose may be sufficient as a single dose to have a therapeutic or suppressive effect or an amount effective to modulate, normalize, or enhance an energy biomarker. Alternatively, the unit dose may be a dose administered periodically in a course of treatment or suppression of a disorder, or to modulate, normalize, or enhance an energy biomarker.

Pharmaceutical compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the invention may be administered enterally, orally, parenterally, sublingually, by inhalation (e.g. as mists or sprays), rectally, or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The compounds are mixed with pharmaceutically acceptable carriers, adjuvants, and vehicles appropriate for the desired route of administration. Oral administration is a preferred route of administration, and formulations suitable for oral administration are preferred formulations. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

In some embodiments of the invention, especially those embodiments where a formulation is used for injection or other parenteral administration including the routes listed herein, but also including embodiments used for oral, gastric, gastrointestinal, or enteric administration, the formulations and preparations used in the methods of the invention are sterile. Sterile pharmaceutical formulations are compounded or manufactured according to pharmaceutical-grade sterilization standards (United States Pharmacopeia Chapters 797, 1072, and 1211; California Business & Professions Code 4127.7; 16 California Code of Regulations 1751, 21 Code of Federal Regulations 211) known to those of skill in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., Methods in Cell Biology, Volume XIV, Academic Press, New York, N.W., p. 33 et seq (1976).

The invention also provides articles of manufacture and kits containing materials useful for treating or suppressing oxidative stress disorders. The invention also provides kits comprising any one or more of the compounds of formula I. In some embodiments, the kit of the invention comprises the container described above.

In other aspects, the kits may be used for any of the methods described herein, including, for example, to treat an individual with a mitochondrial disorder, or to suppress a mitochondrial disorder in an individual.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy. The pharmaceutical unit dosage chosen is usually fabricated and administered to provide a defined final concentration of drug in the blood, tissues, organs, or other targeted region of the body. The therapeutically effective amount or effective amount for a given situation can be readily determined by routine experimentation and is within the skill and judgment of the ordinary clinician.

Examples of dosages which can be used are a therapeutically effective amount or effective amount within the dosage range of about 0.1 mg/kg to about 300 mg/kg body weight, or within about 1.0 mg/kg to about 100 mg/kg body weight, or within about 1.0 mg/kg to about 50 mg/kg body weight, or within about 1.0 mg/kg to about 30 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Compounds of the present invention may be administered in a single daily dose, or the total daily dosage may be administered in divided dosage of two, three or four times daily.

While the compounds of the invention can be administered as the sole active pharmaceutical agent, they can also be used in combination with one or more other agents used in the treatment or suppression of disorders. Representative agents useful in combination with the compounds of the invention for the treatment or suppression of mitochondrial diseases include, but are not limited to, Coenzyme Q, vitamin E, idebenone, MitoQ, vitamins, NAC, and antioxidant compounds.

When additional active agents are used in combination with the compounds of the present invention, the additional active agents may generally be employed in therapeutic amounts as indicated in the Physicians' Desk Reference (PDR) 53rd Edition (1999), or such therapeutically useful amounts as would be known to one of ordinary skill in the art.

The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

The invention will be further understood by the following nonlimiting examples.

PREPARATION OF COMPOUNDS OF THE INVENTION

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Synthetic Reaction Parameters

The terms "solvent", "inert organic solvent" or "inert solvent" mean a solvent inert under the conditions of the reaction being described in conjunction therewith. Solvents employed in synthesis of the compounds of the invention include, for example, methanol ("MeOH"), acetone, water, acetonitrile, 1,4-dioxane, dimethylformamide ("DMF"), benzene, toluene, xylene, tetrahydrofuran ("THF"), chloroform, methylene chloride (or dichloromethane, ("DCM")), diethyl ether, pyridine and the like, as well as mixtures thereof. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

The compounds herein are synthesized by an appropriate combination of generally well-known synthetic methods. Techniques useful in synthesizing the compounds herein are both readily apparent and accessible to those of skill in the relevant art in light of the teachings described herein. The discussion below is offered to illustrate certain of the diverse methods available for use in assembling the compounds herein. However, the discussion is not intended to define the scope of reactions or reaction sequences that are useful in preparing the compounds herein.

A non-limiting, illustrative example of synthesis of compounds of the general formula:

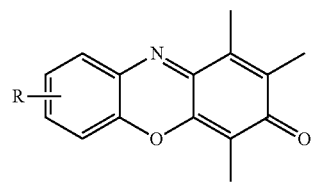

is as follows:
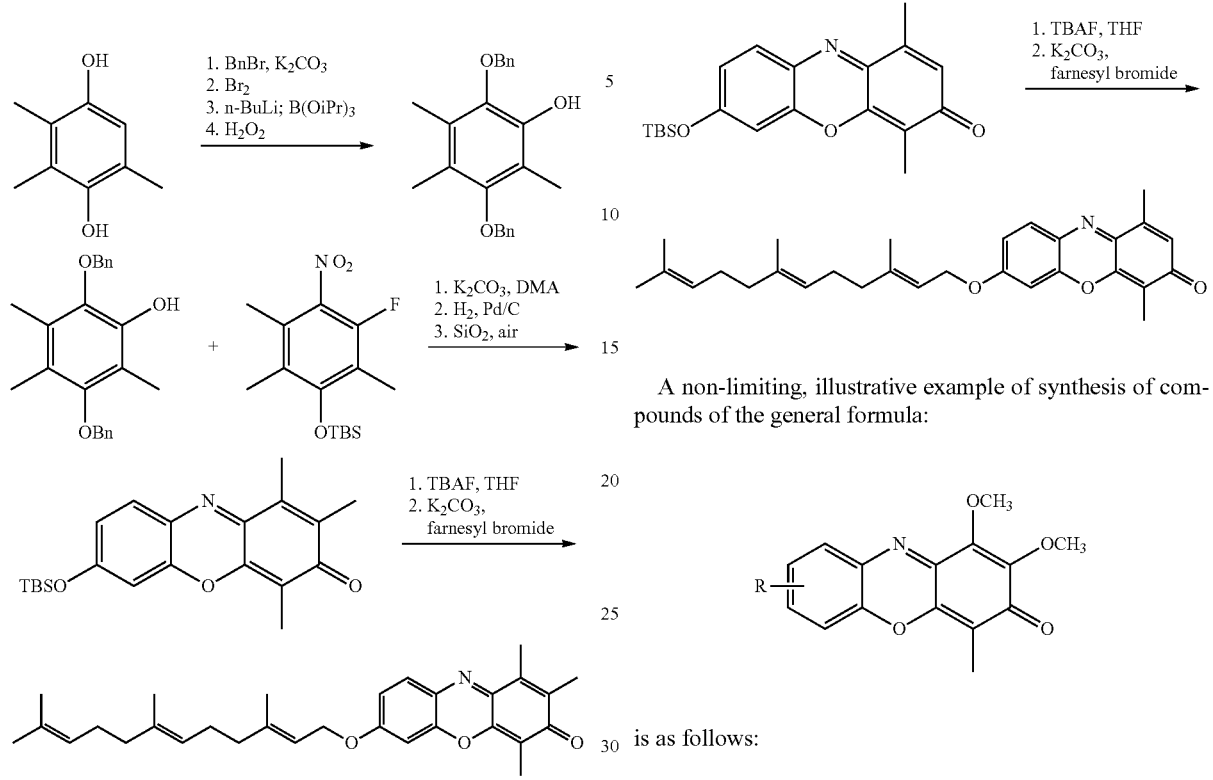
A non-limiting, illustrative example of synthesis of compounds of the general formula:
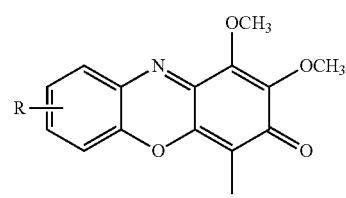
is as follows:
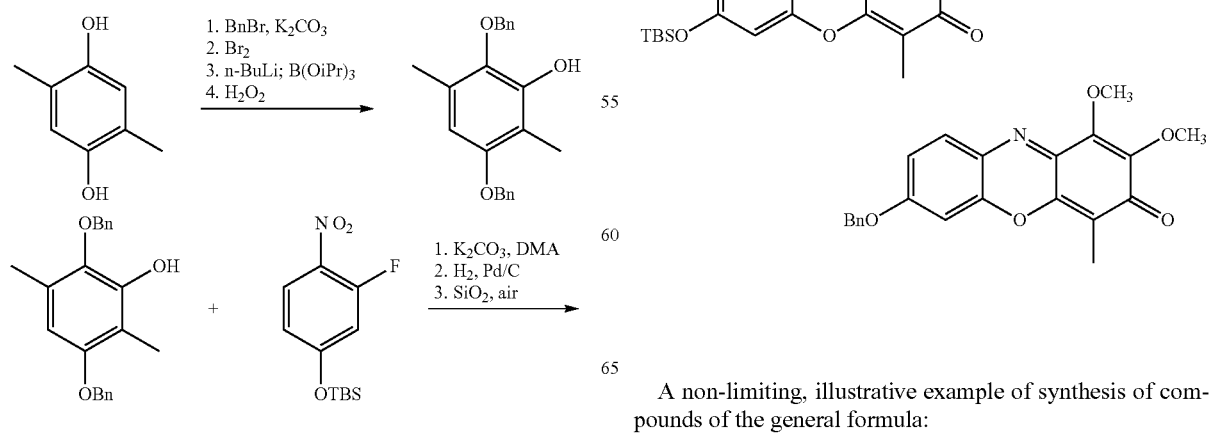
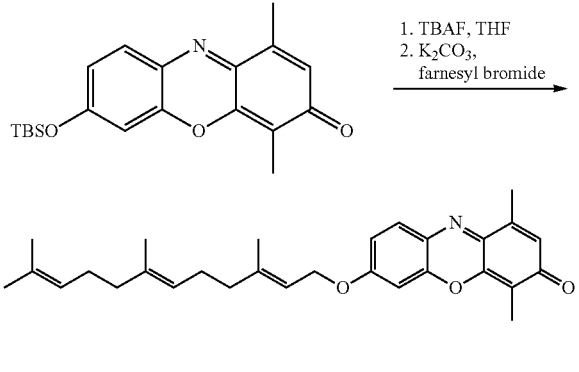
A non-limiting, illustrative example of synthesis of compounds of the general formula:
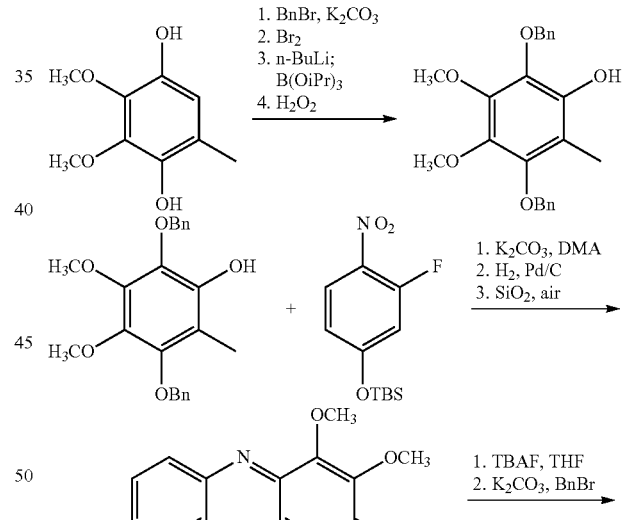
A non-limiting, illustrative example of synthesis of compounds of the general formula:

is as follows:

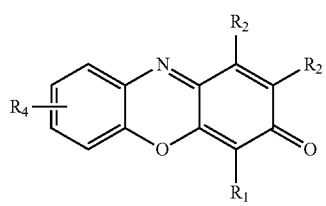
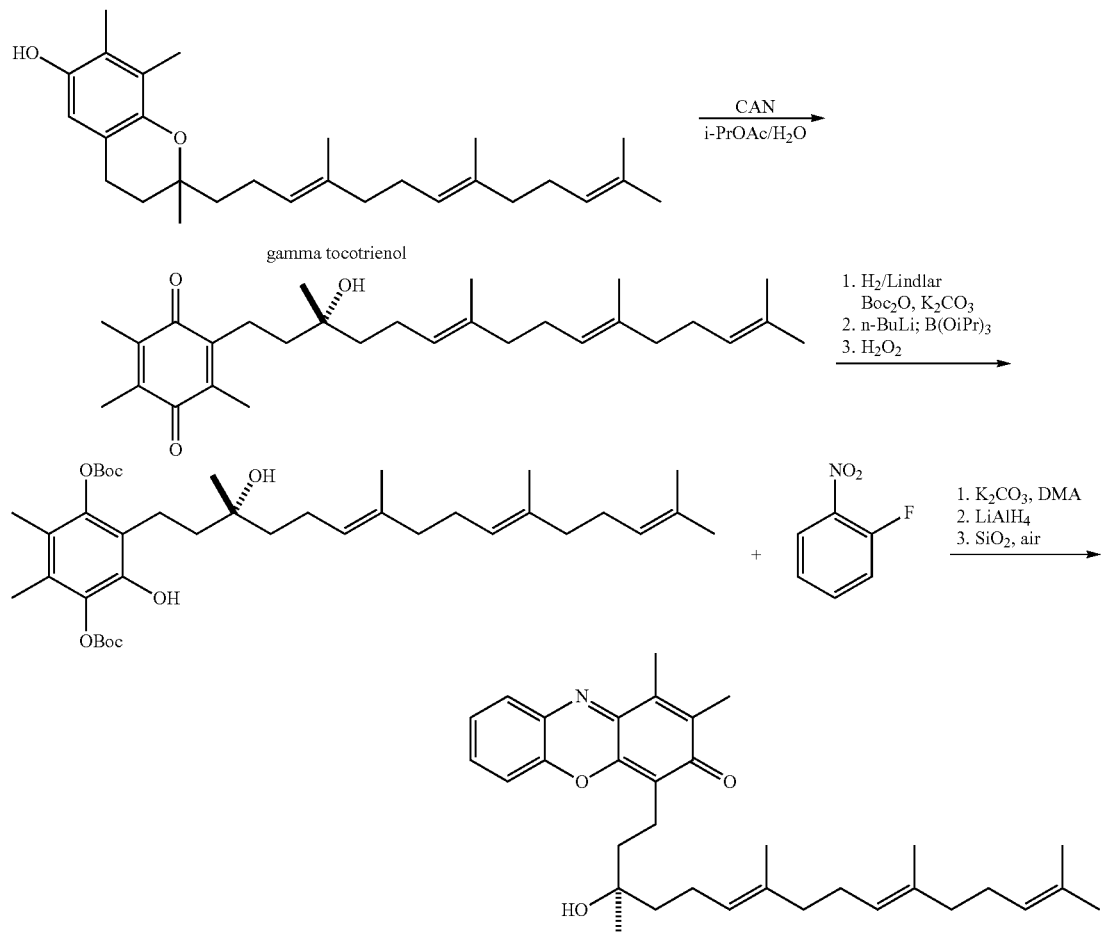

Synthetic methods for other compounds of the invention will be apparent to one skilled in the art in view of the illustrative examples above.

EXAMPLES

Example 1

Screening Compounds of the Invention in Human Dermal Fibroblasts from Friedreich's Ataxia Patients An initial screen was performed to identify compounds effective for the amelioration of redox disorders. Test samples, 4 reference compounds (idebenone, decylubiquinone, Trolox and alpha-tocopherol), and solvent controls were tested for their ability to rescue FRDA fibroblasts stressed by addition of L-buthionine-(S,R)-sulfoximine (BSO), as described in Jauslin et al., Hum. Mol. Genet. 11(24):3055 (2002), Jauslin et al., FASEB J. 17:1972-4 (2003), and International Patent Application WO 2004/003565. Human dermal fibroblasts from Friedreich's Ataxia patients have been shown to be hypersensitive to inhibition of the de novo synthesis of glutathione (GSH) with L-buthionine-(S,R)-sulfoximine (BSO), a specific inhibitor of GSH synthetase (Jauslin et al., Hum. Mol. Genet. 11(24):3055 (2002)). This specific BSO-mediated cell death can be prevented by administration of antioxidants or molecules involved in the antioxidant pathway, such as alpha-tocopherol, selenium, or small molecule glutathione peroxidase mimetics. However, antioxidants differ in their potency, i.e. the concentration at which they are able to rescue BSO-stressed FRDA fibroblasts.

MEM (a medium enriched in amino acids and vitamins, catalog no. 1-31F24-I) and Medium 199 (M199, catalog no. 1-21F22-I) with Earle's Balanced Salts, without phenol red, were purchased from Bioconcept. Fetal Calf Serum was obtained from PAA Laboratories. Basic fibroblast growth factor and epidermal growth factor were purchased from PeproTech. Penicillin-streptomycin-glutamine mix, L-buthionine (S,R)-sulfoximine, (+)-alpha-tocopherol, decylubiquinone, and insulin from bovine pancreas were purchased from Sigma. Trolox (6-Hydroxy-2,5,7,8-tetramethylchromane-2-carboxylic acid) was obtained from Fluka. Idebenone was obtained from Chemo Iberica. Calcein AM was purchased from Anaspec. Cell culture medium was made by combining 125 ml M199 EBS, 50 ml Fetal Calf Serum, 100 U/ml penicillin, 100 microgram/ml streptomycin, 2 mM glutamine, 10 microgram/ml insulin, 10 ng/ml EGF, and 10 ng/ml bFGF; MEM EBS was added to make the volume up to 500 ml. A 10 mM BSO solution was prepared by dissolving 444 mg BSO in 200 ml of medium (Invitrogen, Carlsbad, Ca.) with subsequent filter-sterilization. During the course of the experiments, this solution was stored at +4° C. The cells were obtained from the Coriell Cell Repositories (Camden, N.J.; repository number GM04078) and grown in 10 cm tissue culture plates. Every third day, they were split at a 1:3 ratio.

The test samples were supplied in 1.5 ml glass vials. The compounds were diluted with DMSO, ethanol or PBS to result in a 5 mM stock solution. Once dissolved, they were stored at −20° C. Reference antioxidants (idebenone, decylubiquinone, alpha-tocopherol and Trolox) were dissolved in DMSO.

Test samples were screened according to the following protocol:

A culture with FRDA fibroblasts was started from a 1 ml vial with approximately 500,000 cells stored in liquid nitrogen. Cells were propagated in 10 cm cell culture dishes by splitting every third day in a ratio of 1:3 until nine plates were available. Once confluent, fibroblasts were harvested. For 54 micro titer plates (96 well-MTP) a total of 14.3 million cells (passage eight) were re-suspended in 480 ml medium, corresponding to 100 microliters medium with 3,000 cells/well. The remaining cells were distributed in 10 cm cell culture plates (500,000 cells/plate) for propagation. The plates were incubated overnight at 37° C. in a atmosphere with 95% humidity and 5% CO2 to allow attachment of the cells to the culture plate.

10% DMSO (242.5 microliters) was added to a well of the microtiter plate. The test compounds were unfrozen, and 7.5 microliters of a 5 mM stock solution was dissolved in the well containing 242.5 microliters of 10% DMSO, resulting in a 150 micromolar master solution. Serial dilutions from the master solution were made. The period between the single dilution steps was kept as short as possible (generally less than 30 seconds). At least 4 hours after attachment into MTP, cells were then treated with the various compound dilutions.

Plates were kept overnight in the cell culture incubator. The next day, 10 microliters of a 10 mM BSO solution were added to the wells, resulting in a 1 mM final BSO concentration. Forty-eight hours later, three plates were examined under a phase-contrast microscope to verify that the cells in the negative control (wells E1-H1) were clearly dead. The medium from all plates was discarded, and the remaining liquid was removed by gently tapping the plate inversed onto a paper towel. The plates were washed twice with 100 uL of PBS containing Calcium and Magnesium.

100 microliters of PBS+Ca+Mg containing 1.2 micromolar Calcein AM were then added to each well. The plates were incubated for 30 minutes at 37 C. After that time fluorescence (excitation/emission wavelengths of 485 nm and 525 nm, respectively) was read on a Gemini fluorescence reader. Data was imported into Microsoft Excel (EXCEL is a registered trademark of Microsoft Corporation for a spreadsheet program) and ExcelFit was used to calculate the EC50 concentration for each compound.

The compounds were tested three times, i.e., the experiment was performed three times, the passage number of the cells increasing by one with every repetition.

The solvents (DMSO, ethanol, PBS) neither had a detrimental effect on the viability of non-BSO treated cells nor did they have a beneficial influence on BSO-treated fibroblasts even at the highest concentration tested (1%). None of the compounds showed auto-fluorescence. The viability of non-BSO treated fibroblasts was set as 100%, and the viability of the BSO- and compound-treated cells was calculated as relative to this value.

The following table summarizes the EC50 for the four control compounds.

| | EC50 [micromolar] | | | | |
|---|---|---|---|---|---|
| Compound | Value 1 | Value 2 | Value 3 | Average | Stdev |
| decylubiquinone | 0.05 | 0.035 | 0.03 | 0.038 | 0.010 |
| alpha-tocopherol | 0.4 | 0.15 | 0.35 | 0.30 | 0.13 |
| Idebenone | 1.5 | 1 | 1 | 1.2 | 0.3 |
| Trolox | 9 | 9 | 8 | 8.7 | 0.6 |

The following table summarizes the EC50 for certain compounds of the invention. Compounds were purchased from Sigma.

| | Ec50 [micromolar] | |
|---|---|---|
| Compound | Average | Stdev |
| 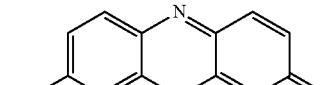 | 0.001 | 0.001 |
| 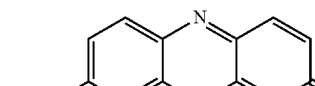 | 0.001 | 0.001 |
| 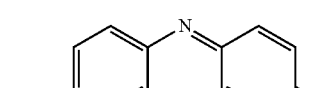 | 0.002 | 0.001 |
| 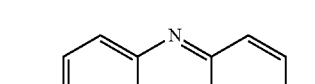 | 0.084 | 0.010 |

Example 2

Screening Compounds of the Invention in Fibroblasts from Huntington's Patients

Compounds of the invention are tested using a screen similar to the one described in Example 1, but substituting FRDA cells with Huntington's cells obtained from the Coriell Cell Repositories (Camden, N.J.; repository number GM 04281). The compounds are tested for their ability to rescue human dermal fibroblasts from Huntington's patients from oxidative stress.

Example 3

Screening Compounds of the Invention in Fibroblasts from Leber's Hereditary Optic Neuropathy Patients Compounds of the invention are tested using a screen similar to the one described in Example 1, but substituting FRDA cells with Leber's Hereditary Optic Neuropathy (LHON)

cells obtained from the Coriell Cell Repositories (Camden, N.J.; repository number GM03858). The compounds are tested for their ability to rescue human dermal fibroblasts from LHON patients from oxidative stress.

Example 4

Screening Compounds of the Invention in Fibroblasts from Parkinson's Disease Patients Compounds of the invention are tested using a screen similar to the one described in Example 1, but substituting FRDA cells with Parkinson's Disease (PD) cells obtained from the Coriell Cell Repositories (Camden, N.J.; repository number AG20439). The compounds are tested for their ability to rescue human dermal fibroblasts from Parkinson's Disease patients from oxidative stress.

Example 5

Screening Compounds of the Invention in Fibroblasts from CoQ10 Deficient Patients Compounds of the invention are tested using a screen similar to the one described in Example 1, but substituting FRDA cells with cells obtained from CoQ10 deficient patients harboring a CoQ2 mutation. The compounds are tested for their ability to rescue human dermal fibroblasts from CoQ10 deficient patients from oxidative stress.

Example 6

Screening Compounds of the Invention in Fibroblasts from Patients

Compounds of the invention are tested using a screen similar to the one described in Example 1, but substituting FRDA cells with cells obtained from patients having an oxidative stress disorder described herein (e.g. MERRF, MELAS, Leigh Disease, KSS, Alzheimer's disease, ALS, a pervasive development disorder (such as autism, Rett's), stroke). The compounds are tested for their ability to rescue human dermal fibroblasts from these patients from oxidative stress.

Example 7

Administration of Compounds of the Invention

A compound of the invention is presented in a capsule containing 300 mg of compound in a pharmaceutically acceptable carrier. A capsule is taken orally, once a day, preferably during breakfast or lunch. In case of very young children, the capsule is broken and its contents mixed with food.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

Non limiting embodiments of the invention include the following:

1. A compound of formula (I):

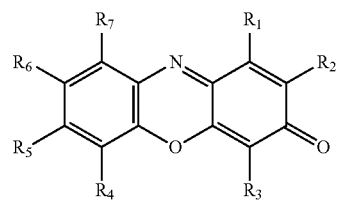

wherein: $R_1$ and $R_2$ are independently selected from the group consisting of: —H, —$C_1$-$C_4$ alkyl, —O—$C_1$-$C_4$ alkyl, and —$C_1$-$C_4$ haloalkyl, and $R_3$ is selected from the group consisting of: —H, —$C_1$-$C_{12}$ alkyl, —O—$C_1$-$C_{12}$ alkyl, and —$C_1$-$C_{12}$ haloalkyl; or $R_1$ and $R_2$ are both —$CH_3$ or $R_1$ and $R_2$ are both —$OCH_3$, and $R_3$ is selected from the group consisting of:

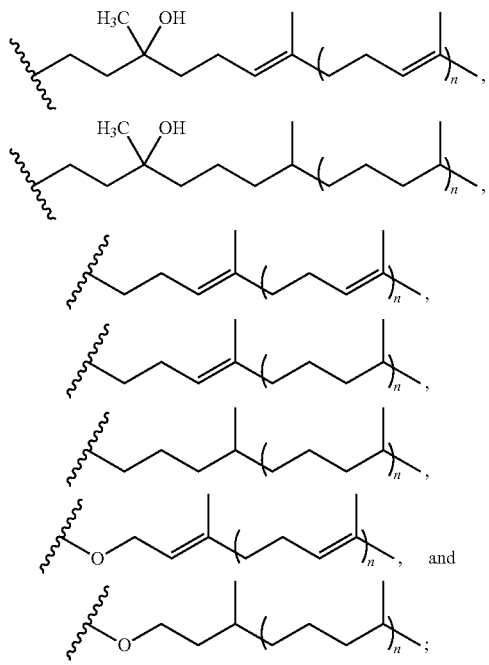

n is 0, 1, 2, 3, or 4;
$R_4$, $R_5$, $R_6$, and $R_7$ are independently selected from the group consisting of: —H, —$C_1$-$C_{12}$ alkyl, —$C_2$-$C_{12}$ alkenyl, —$C_1$-$C_{12}$ haloalkyl, —O—$C_1$-$C_{12}$ alkyl, —O—$C_1$-$C_{12}$ haloalkyl, —$C_6$-$C_{10}$ aryl, —O—$C_6$-$C_{10}$ aryl, —$C_1$-$C_6$ alkyl-$C_6$-$C_{10}$ aryl, —O—$C_1$-$C_6$ alkyl-$C_6$-$C_{10}$ aryl, —N—($R_8$)($R_9$),

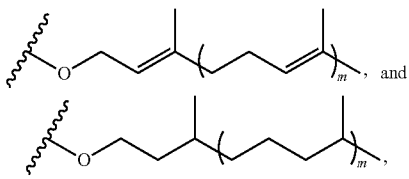

with the proviso that at least two of $R_4$, $R_5$, $R_6$, and $R_7$ are independently selected from the group consisting of: —H and —$CH_3$; $R_8$ and $R_9$ are independently —H or —$C_1$-$C_{12}$ alkyl;

and m is 0, 1, 2, or 3; or a stereoisomer, mixture of stereoisomers, solvate, hydrate, or pharmaceutically acceptable salt thereof; with the proviso that the compound is not:

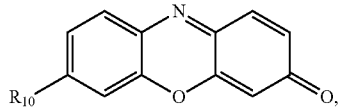

wherein $R_{10}$ is —H, —OH, —O-alkyl, or —O-benzyl, or a stereoisomer, mixture of stereoisomers, solvate, hydrate, or pharmaceutically acceptable salt thereof.

2. The compound of embodiment 1, wherein one of $R_1$, $R_2$, and $R_3$ is not —H.
3. The compound of embodiment 1, wherein two of $R_1$, $R_2$, and $R_3$ are not —H.
4. The compound of embodiment 1, wherein $R_1$, $R_2$, and $R_3$ are not —H.
5. The compound of embodiment 1, wherein one of $R_1$, $R_2$, and $R_3$ is —CH$_3$.
6. The compound of embodiment 1, wherein two of $R_1$, $R_2$, and $R_3$ are —CH$_3$.
7. The compound of embodiment 1, wherein $R_1$, $R_2$, and $R_3$ are —CH$_3$.
8. The compound of embodiment 1, wherein two of $R_1$, $R_2$, and $R_3$ are —CH$_3$ and one of $R_1$, $R_2$, and $R_3$ is —H.
9. The compound of embodiment 1, wherein $R_1$ and $R_3$ are —CH$_3$, and $R_2$ is —H.
10. The compound of embodiment 1, wherein $R_1$ and $R_2$ are —CH$_3$.
11. The compound of embodiment 1, wherein $R_1$ and $R_2$ are —OCH$_3$.
12. The compound of embodiment 1, wherein $R_1$ and $R_2$ are —OCH$_3$, and $R_3$ is —CH$_3$.
13. The compound of embodiment 1, wherein $R_1$ and $R_2$ are —CH$_3$, and wherein $R_3$ is -n-C$_1$-C$_{12}$ alkyl.
14. The compound of embodiment 1, wherein $R_1$ and $R_2$ are —OCH$_3$, and wherein $R_3$ is -n-C$_1$-C$_{12}$ alkyl.
15. The compound of embodiment 1, wherein $R_1$ and $R_2$ are —CH$_3$, and wherein $R_3$ is selected from the group consisting of:

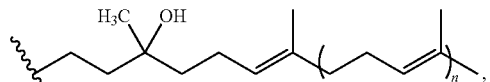

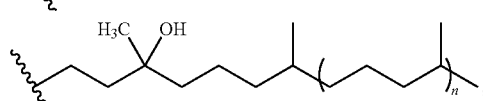

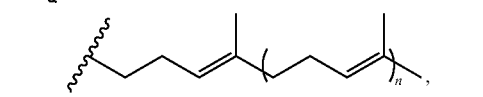

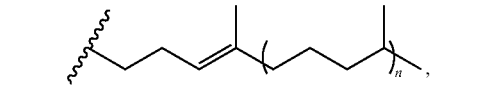

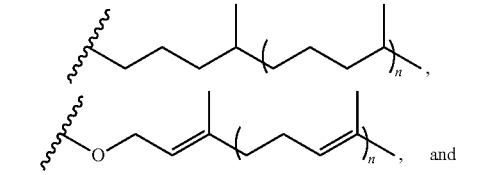

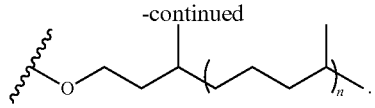

16. The compound of embodiment 1, wherein $R_1$ and $R_2$ are —CH$_3$, and wherein $R_3$ is

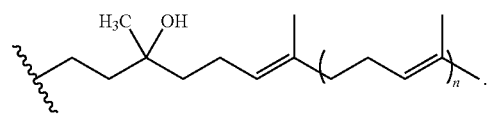

17. The compound of embodiment 16, wherein n is 2.
18. The compound of embodiment 1, wherein $R_1$ and $R_2$ are —CH$_3$, and wherein $R_3$ is

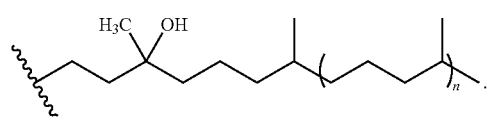

19. The compound of embodiment 18, wherein n is 2.
20. The compound of embodiment 1, wherein $R_1$ and $R_2$ are —CH$_3$, and wherein $R_3$ is

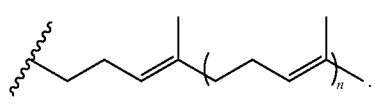

21. The compound of embodiment 20, wherein n is 1.
22. The compound of embodiment 20, wherein n is 2.
23. The compound of embodiment 1, wherein $R_1$ and $R_2$ are —OCH$_3$, and wherein $R_3$ is selected from the group consisting of:

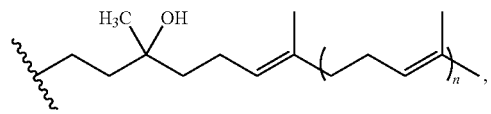

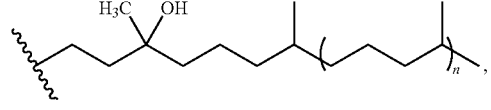

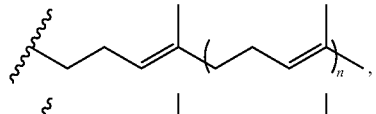

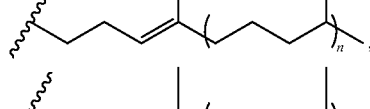

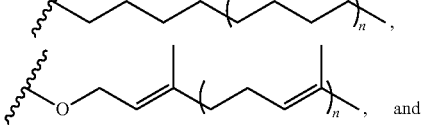

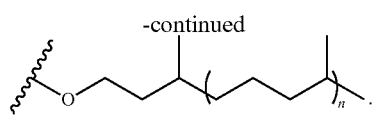

24. The compound of embodiment 1, wherein $R_1$ and $R_2$ are —$OCH_3$, and wherein $R_3$ is

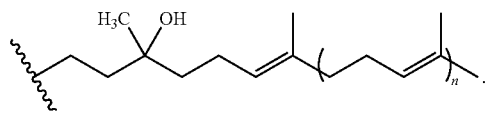

25. The compound of embodiment 24, wherein n is 2.
26. The compound of embodiment 1, wherein $R_1$ and $R_2$ are —$OCH_3$, and wherein $R_3$ is

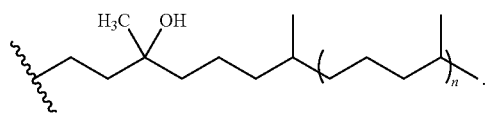

27. The compound of embodiment 26, wherein n is 2.
28. The compound of embodiment 1, wherein $R_1$ and $R_2$ are —$OCH_3$, and wherein $R_3$ is

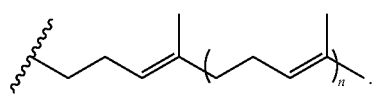

29. The compound of embodiment 28, wherein n is 1.
30. The compound of embodiment 28, wherein n is 2.
31. The compound of embodiment 1, wherein $R_1$ and $R_2$ are independently —H or —$C_1$-$C_4$ alkyl.
32. The compound of embodiment 1, wherein $R_1$, $R_2$, and $R_3$ are —H.
33. The compound of any one of embodiments 1-32, wherein two of $R_4$, $R_5$, $R_6$, and $R_7$ are —H.
34. The compound of any one of embodiments 1-32, wherein three of $R_4$, $R_5$, $R_6$, and $R_7$ are —H.
35. The compound of any one of embodiments 1-32, wherein $R_4$, $R_5$, $R_6$, and $R_7$ are —H.
36. The compound of any one of embodiments 1-32, wherein at least one of $R_4$, $R_5$, $R_6$, and $R_7$ is independently selected from the group consisting of: —$C_1$-$C_{12}$ alkyl, —$C_1$-$C_{12}$ haloalkyl, —O—$C_1$-$C_{12}$ alkyl, —O—$C_1$-$C_6$ alkyl-$C_6$-$C_{10}$ aryl, —N—($R_8$)($R_9$), and

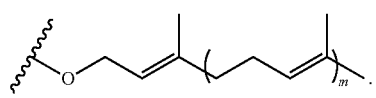

37. The compound of any one of embodiments 1-32, wherein at least one of $R_4$, $R_5$, $R_6$, and $R_7$ is independently selected from the group consisting of: —$C_1$-$C_6$ alkyl, —O—$C_1$-$C_6$ alkyl, —N—($R_8$)($R_9$) wherein $R_8$ and $R_9$ are independently —H or —$C_1$-$C_4$ alkyl, —$CF_3$, —O-benzyl, and

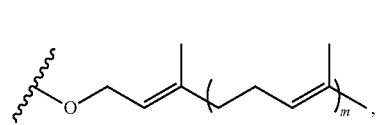

wherein m is 1 or 2.

38. The compound of any one of embodiments 1-32, wherein three of $R_4$, $R_5$, $R_6$, and $R_7$ are —H, and the other is —$N(CH_3)_2$.
39. The compound of any one of embodiments 1-32, wherein three of $R_4$, $R_5$, $R_6$, and $R_7$ are —H, and the other is —O-benzyl.
40. The compound of any one of embodiments 1-32, wherein three of $R_4$, $R_5$, $R_6$, and $R_7$ are —H, and the other is —O—$CH_3$.
41. The compound of any one of embodiments 1-32, wherein three of $R_4$, $R_5$, $R_6$, and $R_7$ are —H, and the other is —O-n-$C_2$-$C_5$ alkyl.
42. The compound of any one of embodiments 1-32, wherein three of $R_4$, $R_5$, $R_6$, and $R_7$ are —H, and the other is —$CF_3$.
43. The compound of any one of embodiments 1-32, wherein three of $R_4$, $R_5$, $R_6$, and $R_7$ are —H, and the other is

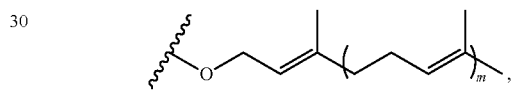

wherein m is 1 or 2.

44. The compound of any one of embodiments 1-32, wherein three of $R_4$, $R_5$, $R_6$, and $R_7$ are —H, and the other is —$CH_3$.
45. The compound of embodiment 1, wherein the compound has the formula:

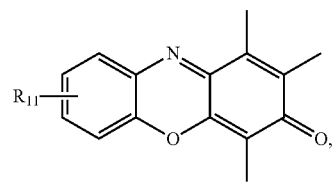

wherein $R_{11}$ is selected from the group consisting of: —$C_1$-$C_6$ alkyl, —O—$C_1$-$C_6$ alkyl, —$N(CH_3)_2$, —$CF_3$, —O-benzyl, and

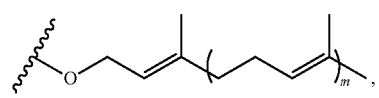

wherein m is 1 or 2, or a stereoisomer, mixture of stereoisomers, solvate, hydrate, or pharmaceutically acceptable salt thereof.

46. The compound of embodiment 1, wherein the compound has the formula:

wherein R$_{11}$ is selected from the group consisting of: —C$_1$-C$_6$ alkyl, —O—C$_1$-C$_6$ alkyl, —N(CH$_3$)$_2$, —CF$_3$, —O-benzyl, and wherein m is 1 or 2, or a stereoisomer, mixture of stereoisomers, solvate, hydrate, or pharmaceutically acceptable salt thereof.

47. The compound of embodiment 1, wherein the compound has the formula:

wherein R$_{11}$ is selected from the group consisting of: —C$_1$-C$_6$ alkyl, —O—C$_1$-C$_6$ alkyl, —N(CH$_3$)$_2$, —CF$_3$, —O-benzyl, and wherein m is 1 or 2, or a stereoisomer, mixture of stereoisomers, solvate, hydrate, or pharmaceutically acceptable salt thereof.

48. The compound of embodiment 1, wherein the compound has the formula:

wherein R$_1$ and R$_2$ are —CH$_3$, or R$_1$ and R$_2$ are —OCH$_3$, and wherein R$_3$ is:

wherein n is 1 or 2, or a stereoisomer, mixture of stereoisomers, solvate, hydrate, or pharmaceutically acceptable salt thereof.

49. The compound of embodiment 1, wherein the compound is selected from the group consisting of:

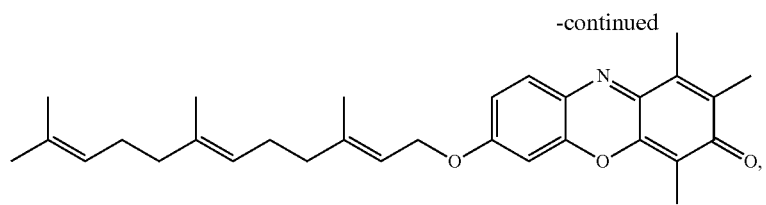 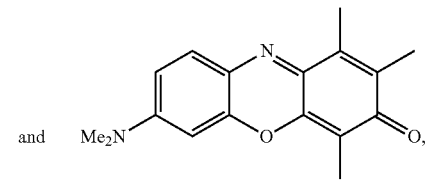

or a stereoisomer, mixture of stereoisomers, solvate, hydrate, or pharmaceutically acceptable salt thereof.

50. The compound of embodiment 1, wherein the compound is selected from the group consisting of:

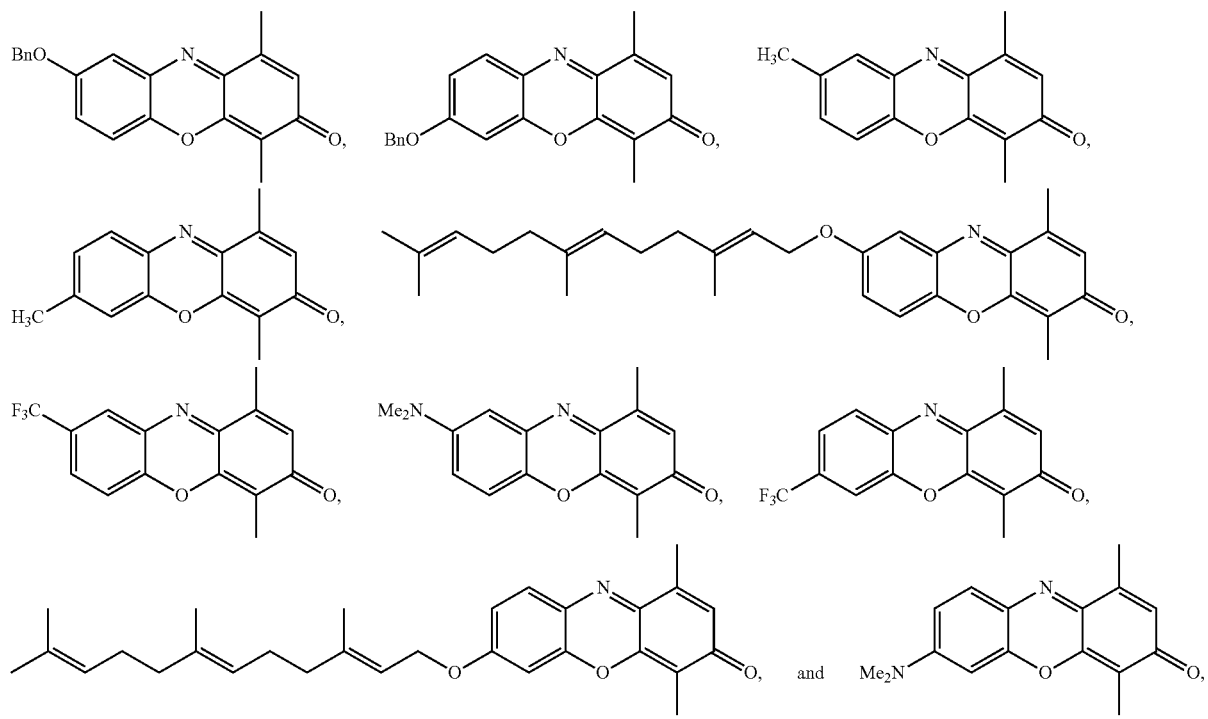

or a stereoisomer, mixture of stereoisomers, solvate, hydrate, or pharmaceutically acceptable salt thereof.

51. The compound of embodiment 1, wherein the compound is selected from the group consisting of:

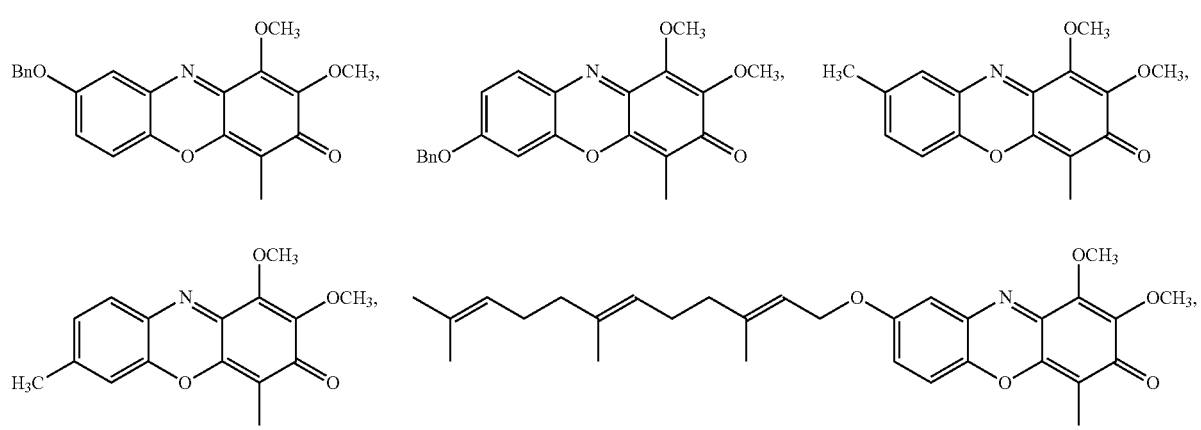

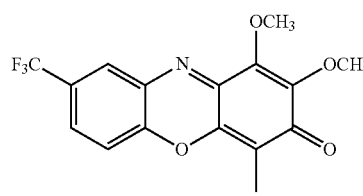
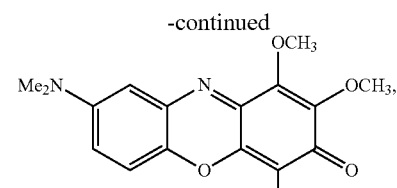
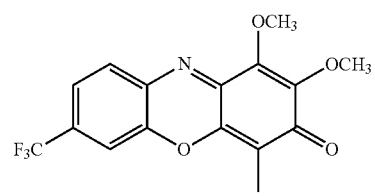

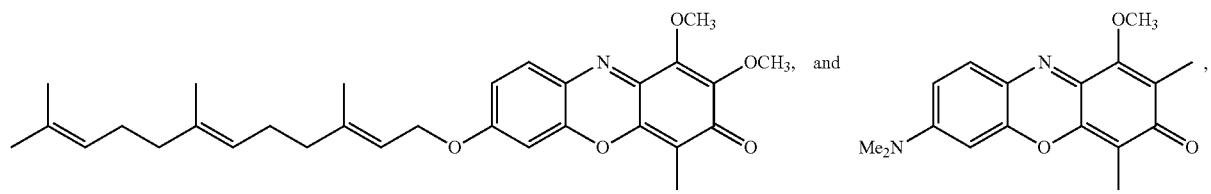

or a stereoisomer, mixture of stereoisomers, solvate, hydrate, or pharmaceutically acceptable salt thereof.

52. The compound of embodiment 1, wherein the compound is selected from the group consisting of:

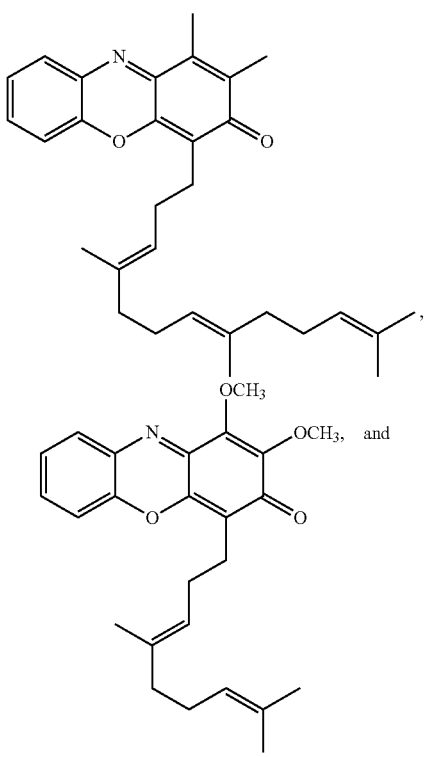

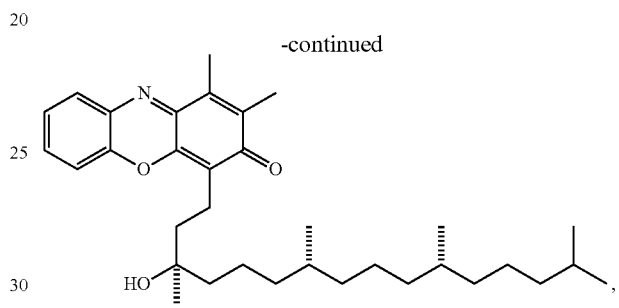

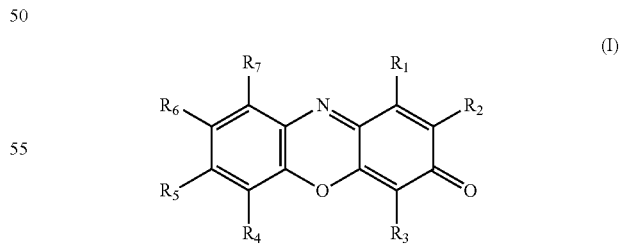

or a stereoisomer, mixture of stereoisomers, solvate, hydrate, or pharmaceutically acceptable salt thereof.

53. The compound of any one of embodiments 1-52, wherein the compound has an EC50 of less than about 1 micromolar as measured by an assay described in any one of Examples 1-6.

54. A pharmaceutical formulation comprising a compound according to any one of embodiments 1-53 and a pharmaceutically acceptable excipient.

55. A method of treating or suppressing an oxidative stress disorder, modulating one or more energy biomarkers, normalizing one or more energy biomarkers, or enhancing one or more energy biomarkers, comprising administering to a subject a therapeutically effective amount or effective amount of a compound of formula (I):

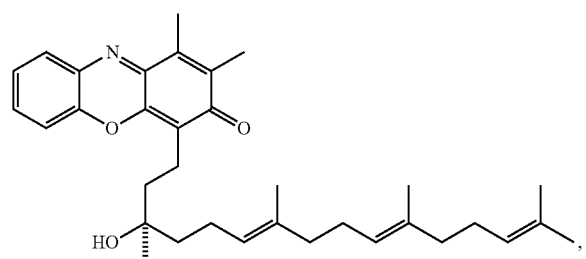

(I)

wherein: $R_1$ and $R_2$ are independently selected from the group consisting of: —H, —$C_1$-$C_4$ alkyl, —O—$C_1$-$C_4$ alkyl, and —$C_1$-$C_4$ haloalkyl, and $R_3$ is selected from the group consisting of: —H, —$C_1$-$C_{12}$ alkyl, —O—$C_1$-$C_{12}$ alkyl, and —$C_1$-$C_{12}$ haloalkyl; or $R_1$ and $R_2$ are both —$CH_3$ or $R_1$ and $R_2$ are both —$OCH_3$, and $R_3$ is selected from the group consisting of:

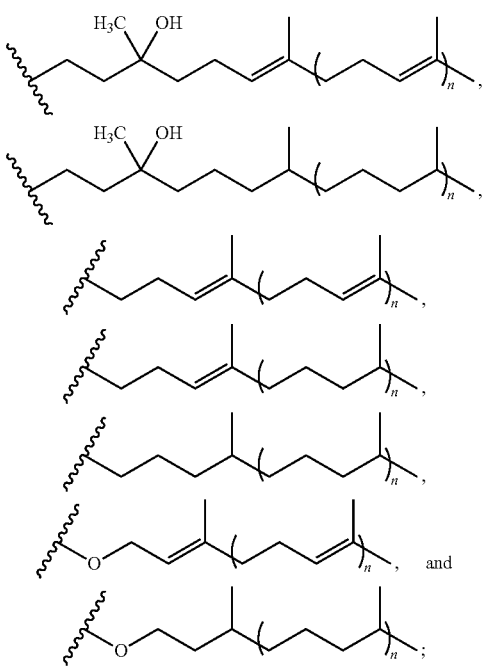

n is 0, 1, 2, 3, or 4; $R_4$, $R_5$, $R_6$, and $R_7$ are independently selected from the group consisting of: —H, —$C_1$-$C_{12}$ alkyl, —$C_2$-$C_{12}$ alkenyl, —$C_1$-$C_{12}$ haloalkyl, —O—$C_1$-$C_{12}$ alkyl, —O—$C_1$-$C_{12}$ haloalkyl, —$C_6$-$C_{10}$ aryl, —O—$C_6$-$C_{10}$ aryl, —$C_1$-$C_6$ alkyl-$C_6$-$C_{10}$ aryl, —O—$C_1$-$C_6$ alkyl-$C_6$-$C_{10}$ aryl, —N—($R_8$)($R_9$),

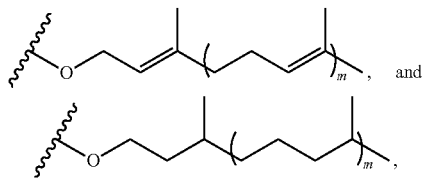

with the proviso that at least two of $R_4$, $R_5$, $R_6$, and $R_7$ are independently selected from the group consisting of: —H and —$CH_3$; $R_8$ and $R_9$ are independently —H or —$C_1$-$C_{12}$ alkyl; and m is 0, 1, 2, or 3; or a stereoisomer, mixture of stereoisomers, solvate, hydrate, or pharmaceutically acceptable salt thereof.

56. The method of embodiment 55, wherein one of $R_1$, $R_2$, and $R_3$ is not —H.

57. The method of embodiment 55, wherein two of $R_1$, $R_2$, and $R_3$ are not —H.

58. The method of embodiment 55, wherein $R_1$, $R_2$, and $R_3$ are not —H.

59. The method of embodiment 55, wherein one of $R_1$, $R_2$, and $R_3$ is —$CH_3$.

60. The method of embodiment 55, wherein two of $R_1$, $R_2$, and $R_3$ are —$CH_3$.

61. The method of embodiment 55, wherein $R_1$, $R_2$, and $R_3$ are —$CH_3$.

62. The method of embodiment 55, wherein two of $R_1$, $R_2$, and $R_3$ are —$CH_3$ and one of $R_1$, $R_2$, and $R_3$ is —H.

63. The method of embodiment 55, wherein $R_1$ and $R_3$ are —$CH_3$, and $R_2$ is —H.

64. The method of embodiment 55, wherein $R_1$ and $R_2$ are —$CH_3$.

65. The method of embodiment 55, wherein $R_1$ and $R_2$ are —$OCH_3$.

66. The method of embodiment 55, wherein $R_1$ and $R_2$ are —$OCH_3$, and $R_3$ is —$CH_3$.

67. The method of embodiment 55, wherein $R_1$ and $R_2$ are —$CH_3$, and wherein $R_3$ is -n-$C_1$-$C_{12}$ alkyl.

68. The method of embodiment 55, wherein $R_1$ and $R_2$ are —$OCH_3$, and wherein $R_3$ is -n-$C_1$-$C_{12}$ alkyl.

69. The method of embodiment 55, wherein $R_1$ and $R_2$ are —$CH_3$, and wherein $R_3$ is selected from the group consisting of:

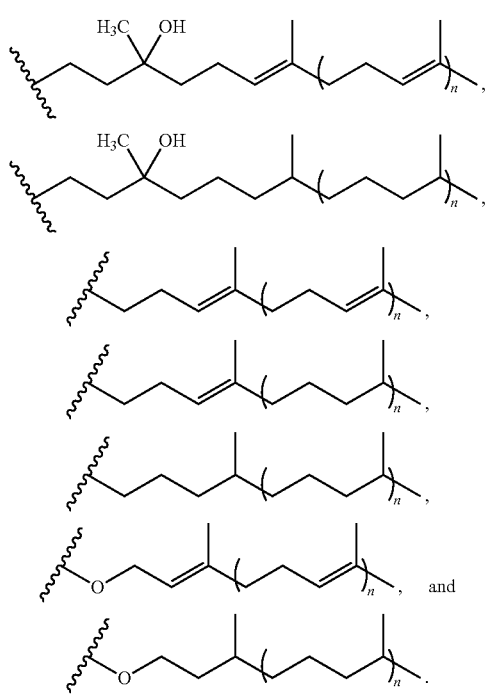

70. The method of embodiment 55, wherein $R_1$ and $R_2$ are —$CH_3$, and wherein $R_3$ is

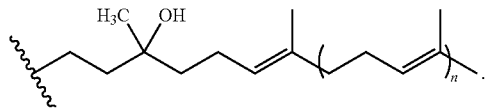

71. The method of embodiment 70, wherein n is 2.

72. The method of embodiment 55, wherein $R_1$ and $R_2$ are —$CH_3$, and wherein $R_3$ is

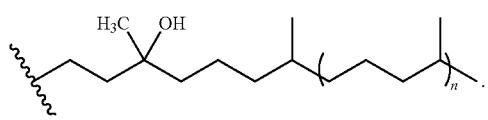

73. The method of embodiment 72, wherein n is 2.

74. The method of embodiment 55, wherein $R_1$ and $R_2$ are —$CH_3$, and wherein $R_3$ is

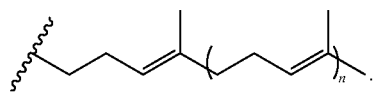

75. The method of embodiment 74, wherein n is 1.
76. The method of embodiment 74, wherein n is 2.
77. The method of embodiment 55, wherein $R_1$ and $R_2$ are —$OCH_3$, and wherein $R_3$ is selected from the group consisting of:

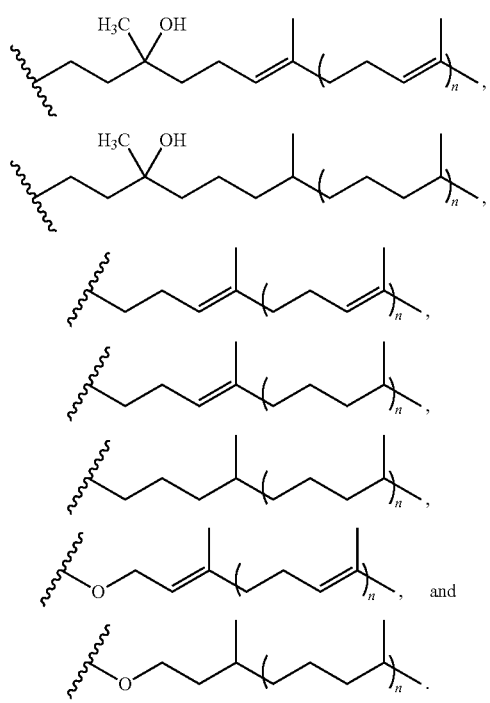

78. The method of embodiment 55, wherein $R_1$ and $R_2$ are —$OCH_3$, and wherein $R_3$ is

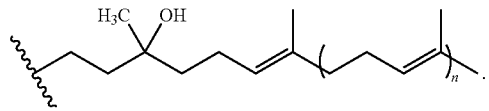

79. The method of embodiment 78, wherein n is 2.
80. The method of embodiment 55, wherein $R_1$ and $R_2$ are —$OCH_3$, and wherein $R_3$ is

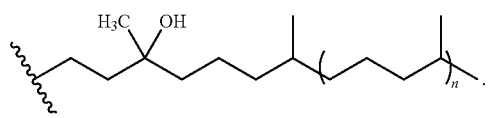

81. The method of embodiment 80, wherein n is 2.
82. The method of embodiment 55, wherein R1 and R7 are —$OCH_3$, and wherein $R_3$ is

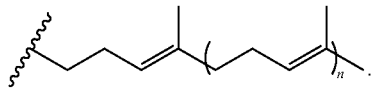

83. The method of embodiment 82, wherein n is 1.
84. The method of embodiment 82, wherein n is 2.
85. The method of embodiment 55, wherein $R_1$ and $R_2$ are independently —H or —$C_1$-$C_4$ alkyl.
86. The method of embodiment 55, wherein $R_1$, $R_2$, and $R_3$ are —H.
87. The method of any one of embodiments 55-86, wherein two of $R_4$, $R_5$, $R_6$, and $R_7$ are —H.
88. The method of any one of embodiments 55-86, wherein three of $R_4$, $R_5$, $R_6$, and $R_7$ are —H.
89. The method of any one of embodiments 55-86, wherein $R_4$, $R_5$, $R_6$, and $R_7$ are —H.
90. The method of any one of embodiments 55-86, wherein at least one of $R_4$, $R_5$, $R_6$, and $R_7$ is independently selected from the group consisting of: —$C_1$-$C_{12}$ alkyl, —$C_1$-$C_{12}$ haloalkyl, —O—$C_1$-$C_{12}$ alkyl, —O—$C_1$-$C_{12}$ alkyl-$C_6$-$C_{10}$ aryl, —N—($R_8$)($R_9$), and 91. The method of any one of embodiments 55-86, wherein at least one of $R_4$, $R_5$, $R_6$, and $R_7$ is independently selected from the group consisting of: —$C_1$-$C_6$ alkyl, —O—$C_1$-$C_6$ alkyl, —N—($R_8$)($R_9$) wherein $R_8$ and $R_9$ are independently —H or —$C_1$-$C_4$ alkyl, —$CF_3$, —O-benzyl, and wherein m is 1 or 2.
92. The method of any one of embodiments 55-86, wherein three of $R_4$, $R_5$, $R_6$, and $R_7$ are —H, and the other is —$N(CH_3)_2$.
93. The method of any one of embodiments 55-86, wherein three of $R_4$, $R_5$, $R_6$, and $R_7$ are —H, and the other is —O-benzyl.
94. The method of any one of embodiments 55-86, wherein three of $R_4$, $R_5$, $R_6$, and $R_7$ are —H, and the other is —O—$CH_3$.
95. The method of any one of embodiments 55-86, wherein three of $R_4$, $R_5$, $R_6$, and $R_7$ are —H, and the other is —O-n-$C_2$-$C_5$ alkyl.
96. The method of any one of embodiments 55-86, wherein three of $R_4$, $R_5$, $R_6$, and $R_7$ are —H, and the other is —$CF_3$.
97. The method of any one of embodiments 55-86, wherein three of $R_4$, $R_5$, $R_6$, and $R_7$ are —H, and the other is wherein m is 1 or 2.

98. The method of any one of embodiments 55-86, wherein three of $R_4$, $R_5$, $R_6$, and $R_7$ are —H, and the other is —$CH_3$.

99. The method of embodiment 55, wherein the compound has the formula:

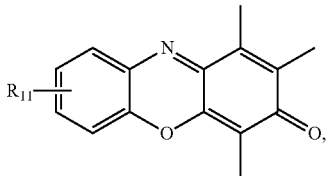

wherein $R_{11}$ is selected from the group consisting of: —$C_1$-$C_6$ alkyl, —O—$C_1$-$C_6$ alkyl, —N$(CH_3)_2$, —$CF_3$, —O-benzyl, and

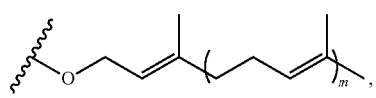

wherein m is 1 or 2, or a stereoisomer, mixture of stereoisomers, solvate, hydrate, or pharmaceutically acceptable salt thereof.

100. The method of embodiment 55, wherein the compound has the formula:

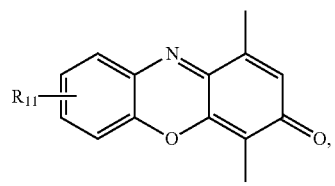

wherein $R_{11}$ is selected from the group consisting of: —$C_1$-$C_6$ alkyl, —O—$C_1$-$C_6$ alkyl, —N$(CH_3)_2$, —$CF_3$, —O-benzyl, and

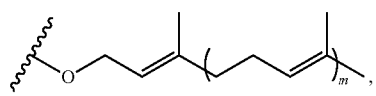

wherein m is 1 or 2, or a stereoisomer, mixture of stereoisomers, solvate, hydrate, or pharmaceutically acceptable salt thereof.

101. The method of embodiment 55, wherein the compound has the formula:

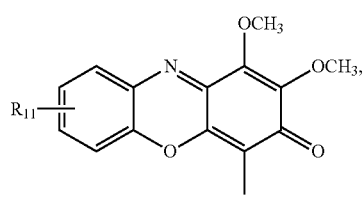

wherein $R_{11}$ is selected from the group consisting of: —$C_1$-$C_6$ alkyl, —O—$C_1$-$C_6$ alkyl, —N$(CH_3)_2$, —$CF_3$, —O-benzyl, and

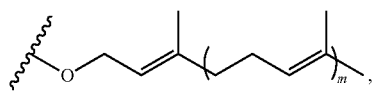

wherein m is 1 or 2, or a stereoisomer, mixture of stereoisomers, solvate, hydrate, or pharmaceutically acceptable salt thereof.

102. The method of embodiment 55, wherein the compound has the formula:

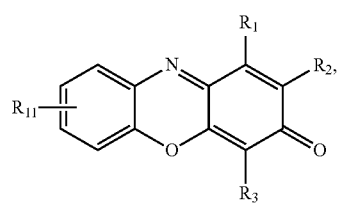

wherein $R_1$ and $R_2$ are —$CH_3$, or $R_1$ and $R_2$ are —$OCH_3$, and wherein $R_3$ is:

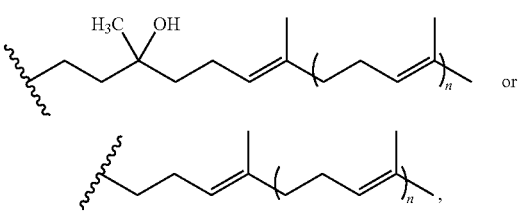

wherein n is 1 or 2, or a stereoisomer, mixture of stereoisomers, solvate, hydrate, or pharmaceutically acceptable salt thereof.

103. The method of any one of embodiments 55-98, wherein the compound is not:

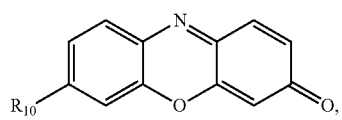

wherein $R_{10}$ is —H, —O-alkyl, or —O-benzyl, or a stereoisomer, mixture of stereoisomers, solvate, hydrate, or pharmaceutically acceptable salt thereof.

104. The method of embodiment 55, wherein the compound is selected from the group consisting of:

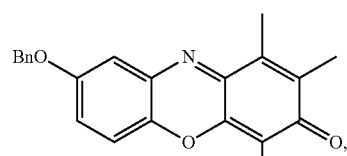 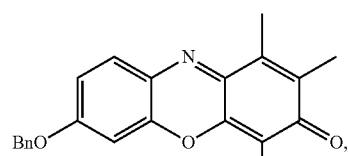 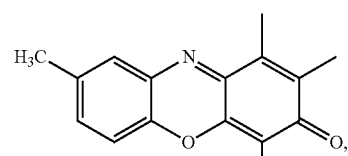

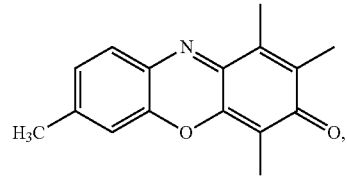 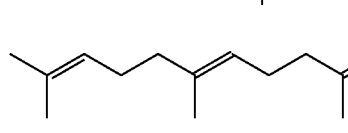 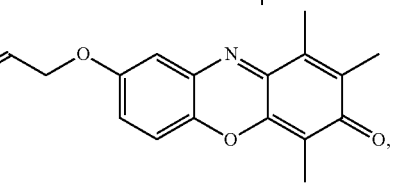

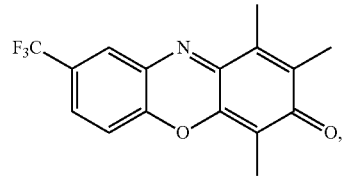 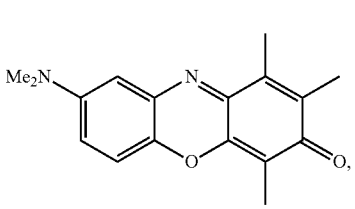 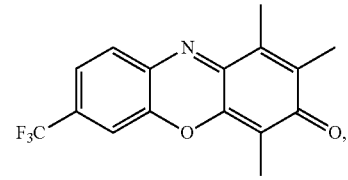

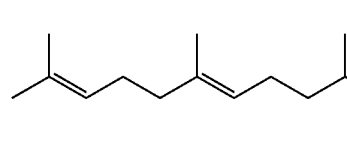 and 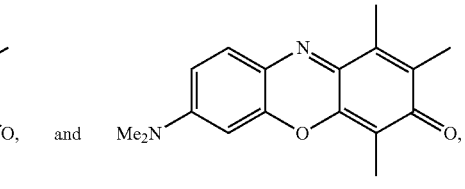

or a stereoisomer, mixture of stereoisomers, solvate, hydrate, or pharmaceutically acceptable salt thereof.

105. The method of embodiment 55, wherein the compound is selected from the group consisting of:

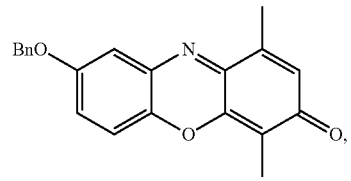 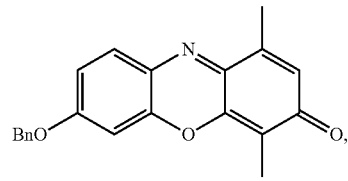 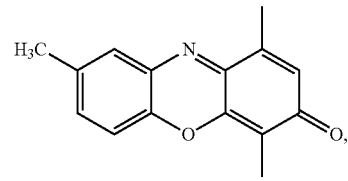

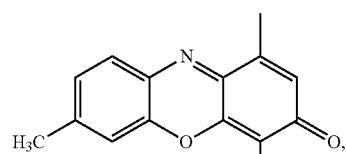 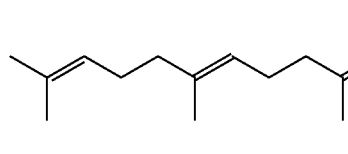 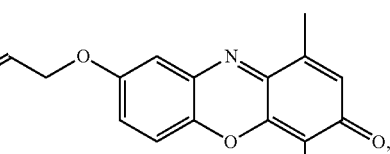

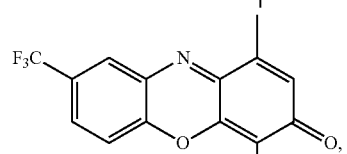 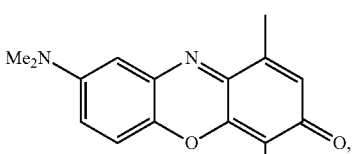 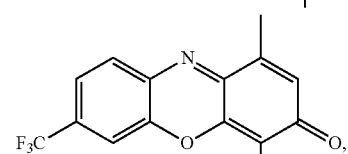

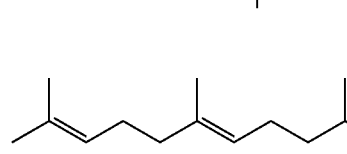 and 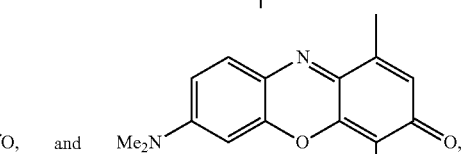

or a stereoisomer, mixture of stereoisomers, solvate, hydrate, or pharmaceutically acceptable salt thereof.

106. The method of embodiment 55, wherein the compound is selected from the group consisting of:

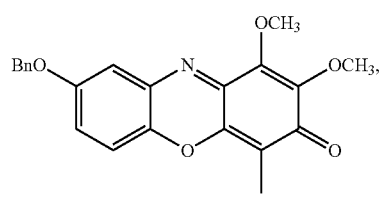
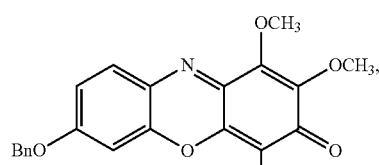
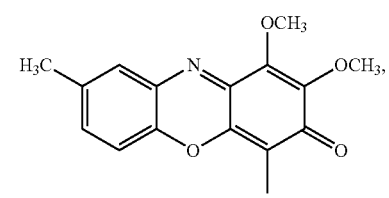

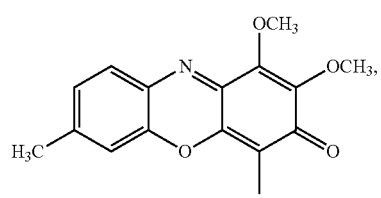
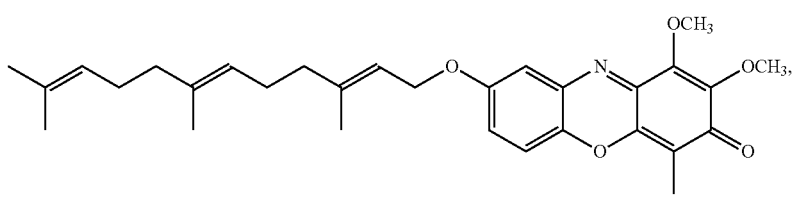

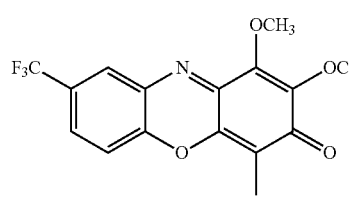
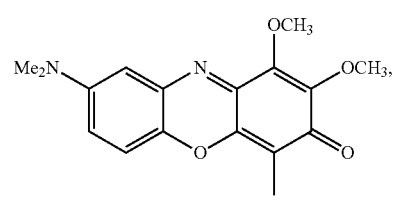
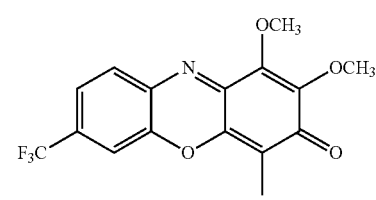

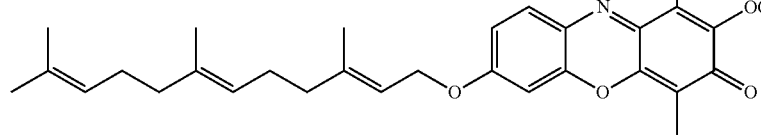
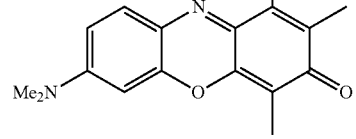

or a stereoisomer, mixture of stereoisomers, solvate, hydrate, or pharmaceutically acceptable salt thereof.

107. The method of embodiment 55, wherein the compound is selected from the group consisting of:

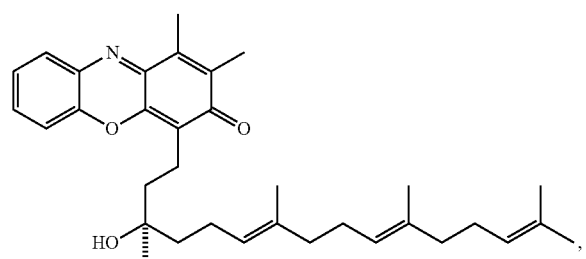

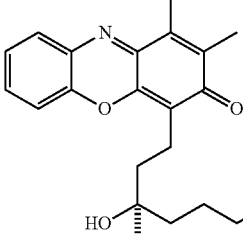

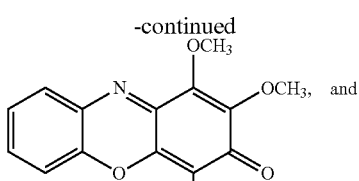

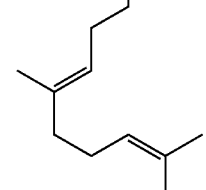

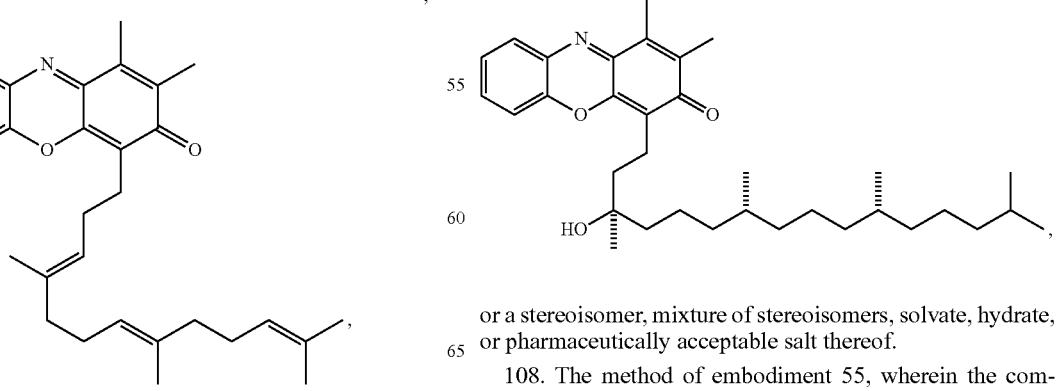

or a stereoisomer, mixture of stereoisomers, solvate, hydrate, or pharmaceutically acceptable salt thereof.

108. The method of embodiment 55, wherein the compound is selected from the group consisting of:

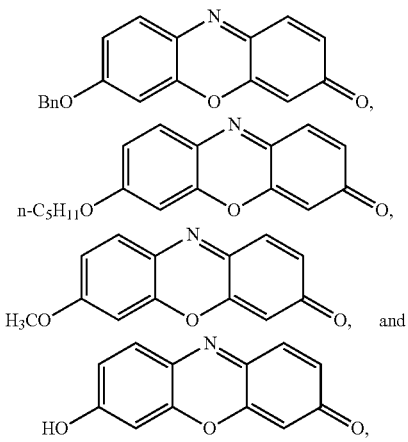

or a stereoisomer, mixture of stereoisomers, solvate, hydrate, or pharmaceutically acceptable salt thereof.

109. The method of any one of embodiments 55-108, wherein the compound is administered as a pharmaceutical formulation comprising the compound and a pharmaceutically acceptable excipient.

110. The method of any one of embodiments 55-109, wherein the method is a method of treating an oxidative stress disorder selected from the group consisting of: a mitochondrial disorder; an inherited mitochondrial disease; Alpers Disease; Barth syndrome; a Beta-oxidation Defect; Carnitine-Acyl-Carnitine Deficiency; Carnitine Deficiency; a Creatine Deficiency Syndrome; Co-Enzyme Q10 Deficiency; Complex I Deficiency; Complex II Deficiency; Complex III Deficiency; Complex IV Deficiency; Complex V Deficiency; COX Deficiency; chronic progressive external ophthalmoplegia (CPEO); CPT I Deficiency; CPT II Deficiency; Friedreich's Ataxia (FA); Glutaric Aciduria Type II; Kearns-Sayre Syndrome (KSS); Lactic Acidosis; Long-Chain Acyl-CoA Dehydrongenase Deficiency (LCAD); LCHAD; Leigh Disease; Leigh-like Syndrome; Leber's Hereditary Optic Neuropathy (LHON); Lethal Infantile Cardiomyopathy (LIC); Luft Disease; Multiple Acyl-CoA Dehydrogenase Deficiency (MAD); Medium-Chain Acyl-CoA Dehydrongenase Deficiency (MCAD); Mitochondrial Myopathy, Encephalopathy, Lactacidosis, Stroke (MELAS); Myoclonic Epilepsy with Ragged Red Fibers (MERRF); Mitochondrial Recessive Ataxia Syndrome (MIRAS); Mitochondrial Cytopathy, Mitochondrial DNA Depletion; Mitochondrial Encephalopathy; Mitochondrial Myopathy; Myoneurogastointestinal Disorder and Encephalopathy (MNGIE); Neuropathy, Ataxia, and Retinitis Pigmentosa (NARP); Pearson Syndrome; Pyruvate Carboxylase Deficiency; Pyruvate Dehydrogenase Deficiency; a POLG Mutation; a Respiratory Chain Disorder; Short-Chain Acyl-CoA Dehydrogenase Deficiency (SCAD); SCHAD; Very Long-Chain Acyl-CoA Dehydrongenase Deficiency (VLCAD); a myopathy; cardiomyopathy; encephalomyopathy; a neurodegenerative disease; Parkinson's disease; Alzheimer's disease; amyotrophic lateral sclerosis (ALS); a motor neuron disease; a neurological disease; epilepsy; an age-associated disease; macular degeneration; diabetes; metabolic syndrome; cancer; brain cancer; a genetic disease; Huntington's Disease; a mood disorder; schizophrenia; bipolar disorder; a pervasive developmental disorder; autistic disorder; Asperger's syndrome; childhood disintegrative disorder (CDD); Rett's disorder; PDD-not otherwise specified (PDD-NOS); a cerebrovascular accident; stroke; a vision impairment; optic neuropathy; dominant inherited juvenile optic atrophy; optic neuropathy caused by a toxic agent; glaucoma; Stargardt's macular dystrophy; diabetic retinopathy; diabetic maculopathy; retinopathy of prematurity; ischemic reperfusion-related retinal injury; oxygen poisoning; a haemoglobionopathy; thalassemia; sickle cell anemia; seizures; ischemia; renal tubular acidosis; attention deficit/hyperactivity disorder (ADHD); a neurodegenerative disorder resulting in hearing or balance impairment; Dominant Optic Atrophy (DOA); Maternally inherited diabetes and deafness (MIDD); chronic fatigue; contrast-induced kidney damage; contrast-induced retinopathy damage; Abetalipoproteinemia; retinitis pigmentosum; Wolfram's disease; Tourette syndrome; cobalamin c defect; methylmalonic aciduria; glioblastoma; Down's syndrome; acute tubular necrosis; a muscular dystrophy; a leukodystrophy; Progressive Supranuclear Palsy; spinal muscle atropy; hearing loss; noise induced hearing loss; and traumatic brain injury.

111. The method of embodiment 110, wherein the oxidative stress disorder is a mitochondrial disorder.

112. The method of embodiment 110, wherein the oxidative stress disorder is an inherited mitochondrial disease.

113. The method of embodiment 110, wherein the oxidative stress disorder is Friedreich's Ataxia (FA).

114. The method of embodiment 110, wherein the oxidative stress disorder is Kearns-Sayre Syndrome (KSS).

115. The method of embodiment 110, wherein the oxidative stress disorder is Leigh Disease or Leigh-like Syndrome.

116. The method of embodiment 110, wherein the oxidative stress disorder is Leber's Hereditary Optic Neuropathy (LHON).

117. The method of embodiment 110, wherein the oxidative stress disorder is Mitochondrial Myopathy, Encephalopathy, Lactacidosis, Stroke (MELAS).

118. The method of embodiment 110, wherein the oxidative stress disorder is Myoclonic Epilepsy with Ragged Red Fibers (MERRF).

119. The method of embodiment 110, wherein the oxidative stress disorder is Parkinson's disease.

120. The method of embodiment 110, wherein the oxidative stress disorder is Alzheimer's disease.

121. The method of embodiment 110, wherein the oxidative stress disorder is amyotrophic lateral sclerosis (ALS).

122. The method of embodiment 110, wherein the oxidative stress disorder is epilepsy.

123. The method of embodiment 110, wherein the oxidative stress disorder is macular degeneration.

124. The method of embodiment 110, wherein the oxidative stress disorder is brain cancer.

125. The method of embodiment 110, wherein the oxidative stress disorder is Huntington's diseaseDisease.

126. The method of embodiment 110, wherein the oxidative stress disorder is autistic disorder.

127. The method of embodiment 110, wherein the oxidative stress disorder is Rett's disorder.

128. The method of embodiment 110, wherein the oxidative stress disorder is stroke.

129. The method of embodiment 110, wherein the oxidative stress disorder is Maternally inherited diabetes and deafness (MIDD).

130. The method of embodiment 110, wherein the oxidative stress disorder is chronic fatigue.

131. The method of embodiment 110, wherein the oxidative stress disorder is contrast-induced kidney damage.

132. The method of embodiment 110, wherein the oxidative stress disorder is contrast-induced retinopathy damage.

133. The method of embodiment 110, wherein the oxidative stress disorder is cobalamin c defect.

134. The method of any one of embodiments 55-109, wherein the method is a method for modulating one or more energy biomarkers, normalizing one or more energy biomarkers, or enhancing one or more energy biomarkers, wherein the one or more energy biomarkers are selected from the group consisting of: lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; total, reduced or oxidized glutathione levels, or reduced/oxidized glutathione ratio either in whole blood, plasma, lymphocytes, cerebrospinal fluid, or cerebral ventricular fluid; total, reduced or oxidized cysteine levels, or reduced/oxidized cysteine ratio either in whole blood, plasma, lymphocytes, cerebrospinal fluid, or cerebral ventricular fluid; phosphocreatine levels, NADH (NADH+H+) levels; NADPH (NADPH+H+) levels; NAD levels; NADP levels; ATP levels; reduced coenzyme Q ($CoQ_{red}$) levels; oxidized coenzyme Q ($CoQ_{ox}$) levels; total coenzyme Q ($CoQ_{tot}$) levels; oxidized cytochrome C levels; reduced cytochrome C levels; oxidized cytochrome C/reduced cytochrome C ratio; acetoacetate levels, β hydroxy butyrate levels, acetoacetate/β hydroxy butyrate ratio, 8-hydroxy-2'-deoxyguanosine (8-OHdG) levels; levels of reactive oxygen species; levels of oxygen consumption (VO2); levels of carbon dioxide output (VCO2); respiratory quotient (VCO2/VO2); exercise tolerance; and anaerobic threshold.

What is claimed is:

1. A compound of formula (I):

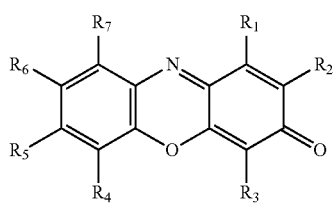

(I)

wherein:
$R_1$ and $R_2$ are independently selected from the group consisting of: —$C_1$-$C_4$ alkyl, —O—$C_1$-$C_4$ alkyl, and —$C_1$-$C_4$ haloalkyl, and $R_3$ is selected from the group consisting of: —$C_1$-$C_{12}$ alkyl, and —$C_1$-$C_{12}$ haloalkyl; or
$R_1$ and $R_2$ are both —$CH_3$ or $R_1$ and $R_2$ are both —$OCH_3$, and $R_3$ is selected from the group consisting of:

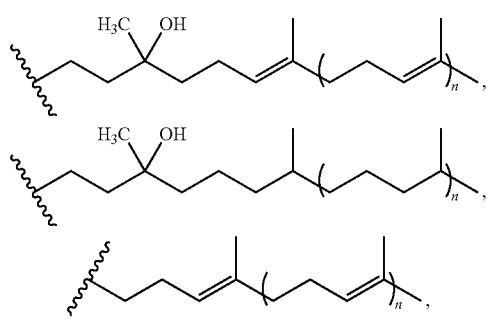

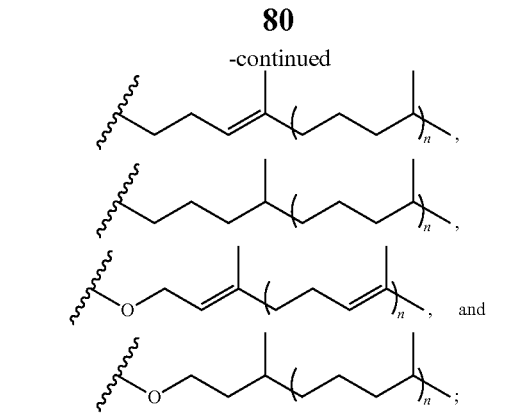

n is 0, 1, 2, 3, or 4;
$R_4$, $R_5$, $R_6$, and $R_7$ are independently selected from the group consisting of: —H, —$C_1$-$C_{12}$ alkyl, —$C_2$-$C_{12}$ alkenyl, —$C_1$-$C_{12}$ haloalkyl, —O—$C_1$-$C_{12}$ alkyl, —O—$C_1$-$C_{12}$ haloalkyl, —$C_6$-$C_{10}$ aryl, —O—$C_6$-$C_{10}$ aryl, —$C_1$-$C_6$ alkyl-$C_6$-$C_{10}$ aryl, —O—$C_1$-$C_6$ alkyl-$C_6$-$C_{10}$ aryl, —N—($R_8$)($R_9$),

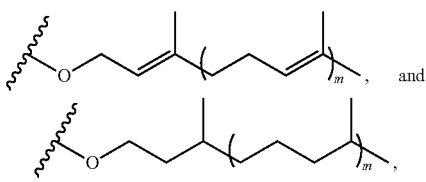

with the proviso that at least two of $R_4$, $R_5$, $R_6$, and $R_7$ are independently selected from the group consisting of: —H and —$CH_3$;
$R_8$ and $R_9$ are independently —$C_1$-$C_{12}$ alkyl; and
m is 0, 1, 2, or 3;
or a stereoisomer, mixture of stereoisomers, solvate, hydrate, or pharmaceutically acceptable salt thereof.

2. The compound of claim 1, wherein $R_1$, $R_2$, and $R_3$ are —$CH_3$.

3. The compound of claim 1, wherein $R_1$ and $R_2$ are —$OCH_3$, and $R_3$ is —$CH_3$.

4. The compound of claim 1, wherein $R_1$ and $R_2$ are —$CH_3$, and wherein $R_3$ is -n-$C_1$-$C_{12}$ alkyl.

5. The compound of claim 1, wherein $R_1$ and $R_2$ are —$OCH_3$, and wherein $R_3$ is -n-$C_1$-$C_{12}$ alkyl.

6. The compound of claim 1, wherein $R_1$ and $R_2$ are —$CH_3$, and wherein $R_3$ is selected from the group consisting of:

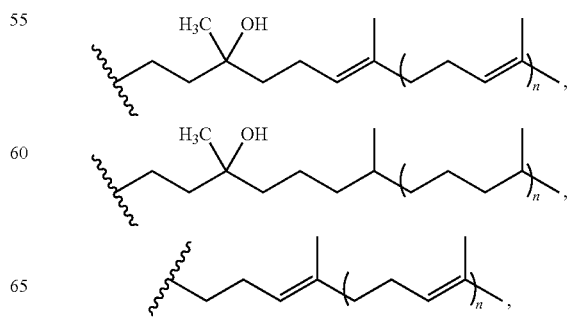

-continued

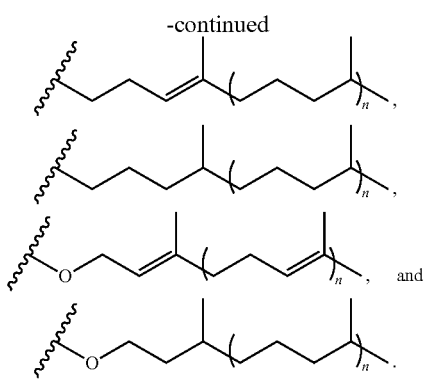

7. The compound of claim 1, wherein $R_1$ and $R_2$ are —$OCH_3$, and wherein $R_3$ is selected from the group consisting of:

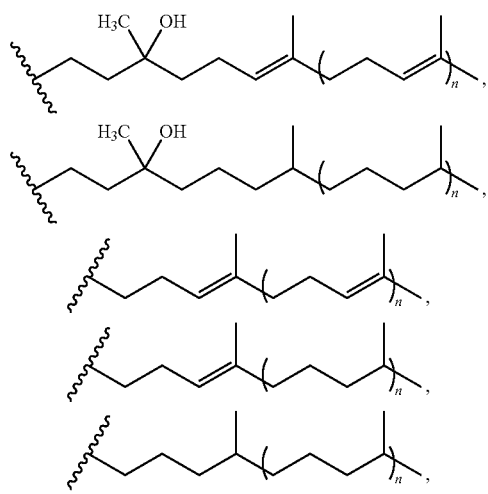

-continued

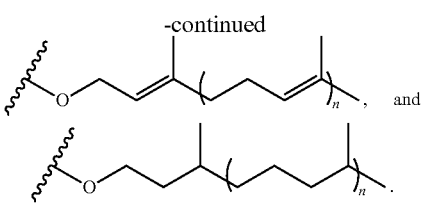

8. The compound of claim 1, wherein three of $R_4$, $R_5$, $R_6$, and $R_7$ are —H.

9. The compound of claim 1, wherein $R_4$, $R_5$, $R_6$, and $R_7$ are —H.

10. The compound of claim 1, wherein at least one of $R_4$, $R_5$, $R_6$, and $R_7$ is independently selected from the group consisting of: —$C_1$-$C_6$ alkyl, —O—$C_1$-$C_6$ alkyl, —N—($R_8$)($R_9$), —$CF_3$, —O-benzyl, and

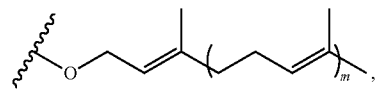

wherein m is 1 or 2; and wherein $R_8$ and $R_9$ are independently —$C_1$-$C_4$ alkyl.

11. The compound of claim 1, wherein three of $R_4$, $R_5$, $R_6$, and $R_7$ are —H, and the other is selected from the group consisting of —$N(CH_3)_2$, —O-benzyl, —O—$CH_3$, —O-n-$C_2$-$C_5$ alkyl, —$CF_3$, —$CH_3$, and

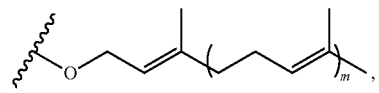

wherein m is 1 or 2.

12. The compound of claim 1, wherein the compound is selected from the group consisting of:

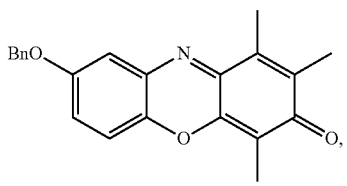 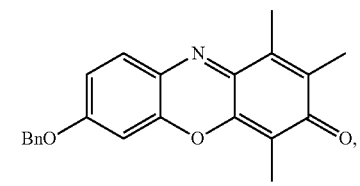 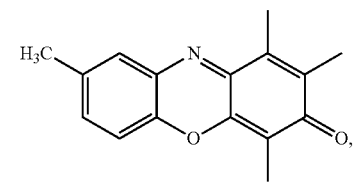

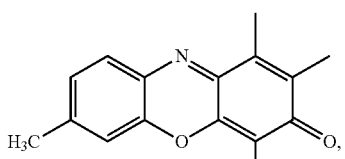 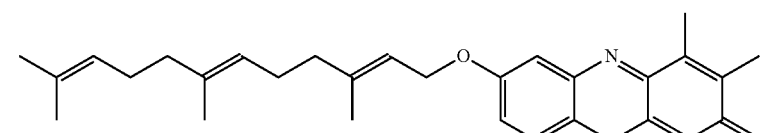

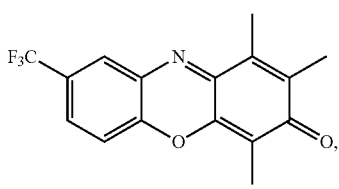 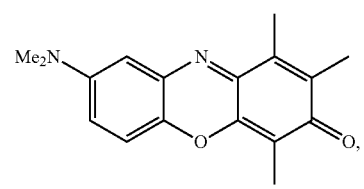 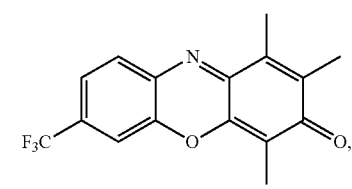

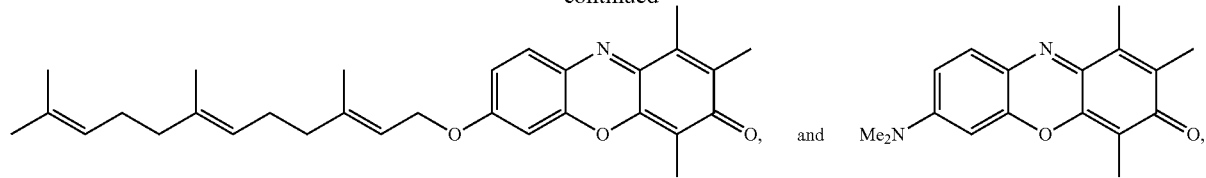

or a stereoisomer, mixture of stereoisomers, solvate, hydrate, or pharmaceutically acceptable salt thereof.

13. The compound of claim 1, wherein the compound is selected from the group consisting of:

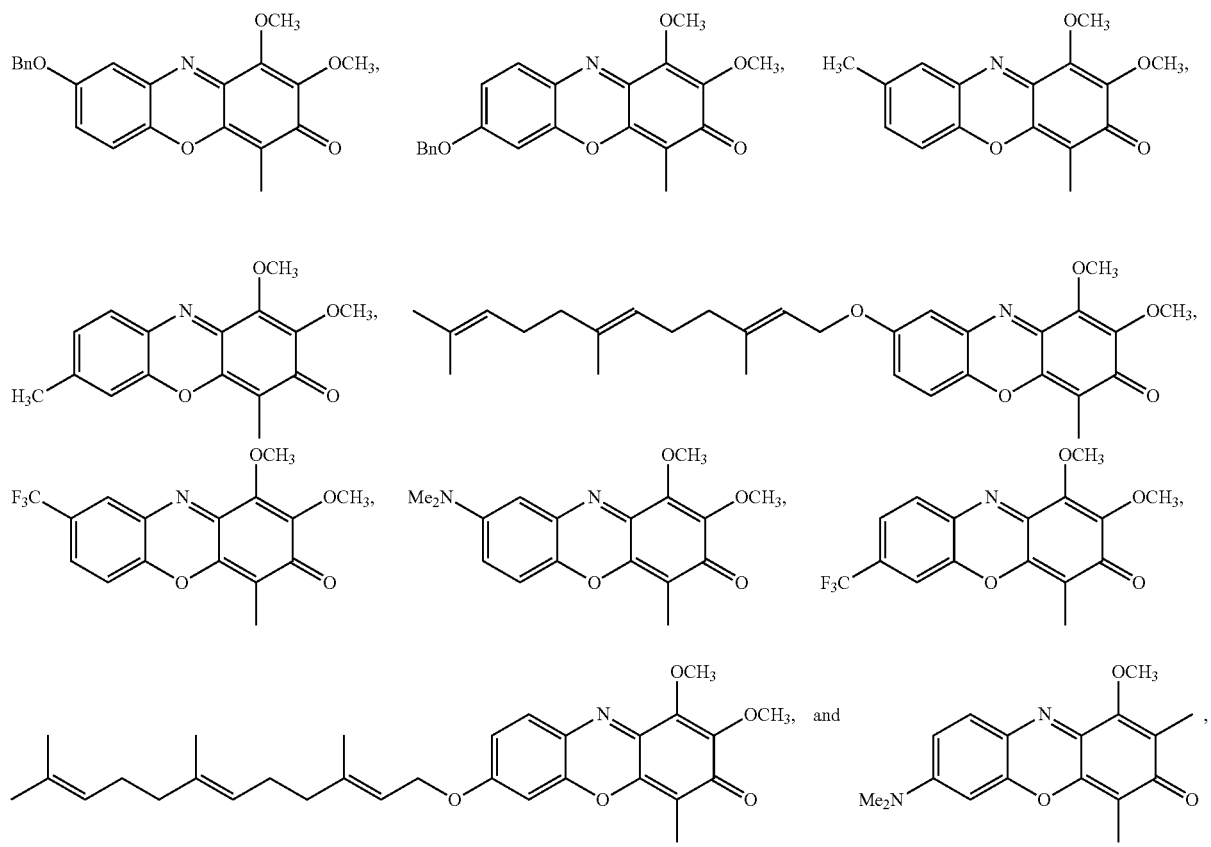

or a stereoisomer, mixture of stereoisomers, solvate, hydrate, or pharmaceutically acceptable salt thereof.

14. The compound of claim 1, wherein the compound is selected from the group consisting of:

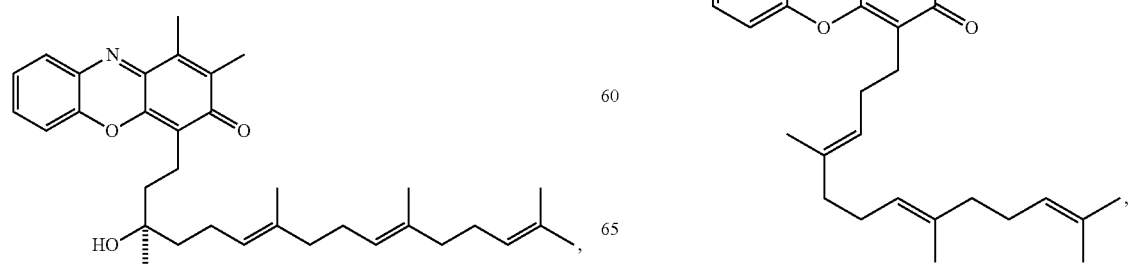

-continued

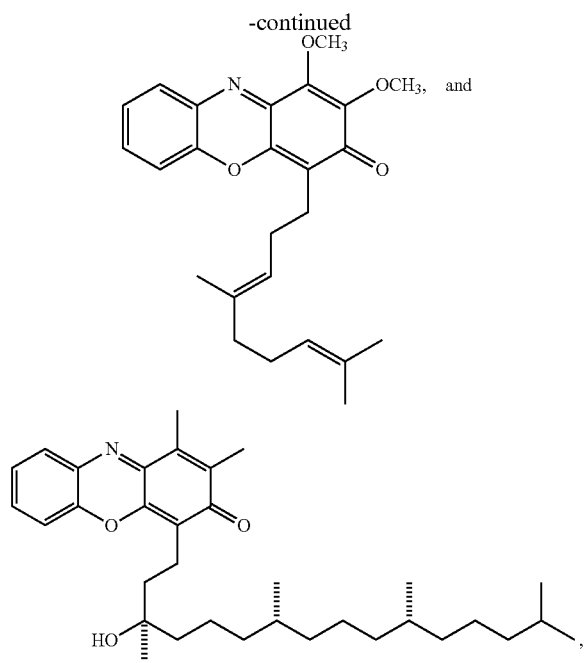

or a stereoisomer, mixture of stereoisomers, solvate, hydrate, or pharmaceutically acceptable salt thereof.

15. A pharmaceutical formulation comprising a compound according to claim 1 and a pharmaceutically acceptable excipient.

16. A method of treating or suppressing an oxidative stress disorder selected from the group consisting of: a mitochondrial disorder; an inherited mitochondrial disease; Alpers Disease; Barth syndrome; a Beta-oxidation Defect; Carnitine-Acyl-Carnitine Deficiency; Carnitine Deficiency; a Creatine Deficiency Syndrome; Co-Enzyme Q10 Deficiency; Complex I Deficiency; Complex II Deficiency; Complex III Deficiency; Complex IV Deficiency; Complex V Deficiency; COX Deficiency; chronic progressive external ophthalmoplegia (CPEO); CPT I Deficiency; CPT II Deficiency; Friedreich's Ataxia (FA); Glutaric Aciduria Type II; Kearns-Sayre Syndrome (KSS); Lactic Acidosis; Long-Chain Acyl-CoA Dehydrogenase Deficiency (LCAD); LCHAD; Leigh Syndrome; Leigh-like Syndrome; Leber's Hereditary Optic Neuropathy (LHON); Lethal Infantile Cardiomyopathy (LIC); Luft Disease; Multiple Acyl-CoA Dehydrogenase Deficiency (MAD); Medium-Chain Acyl-CoA Dehydrogenase Deficiency (MCAD); Mitochondrial Myopathy, Encephalopathy, Lactacidosis, Stroke (MELAS); Myoclonic Epilepsy with Ragged Red Fibers (MERRF); Mitochondrial Recessive Ataxia Syndrome (MIRAS); Mitochondrial Cytopathy, Mitochondrial DNA Depletion; Mitochondrial Encephalopathy; Mitochondrial Myopathy; Myoneurogastrointestinal Disorder and Encephalopathy (MNGIE); Neuropathy, Ataxia, and Retinitis Pigmentosa (NARP); Pearson Syndrome; Pyruvate Carboxylase Deficiency; Pyruvate Dehydrogenase Deficiency; a POLG Mutation; a Respiratory Chain Disorder; Short-Chain Acyl-CoA Dehydrogenase Deficiency (SCAD); SCHAD; Very Long-Chain Acyl-CoA Dehydrogenase Deficiency (VLCAD); a myopathy; cardiomyopathy; encephalomyopathy; Parkinson's disease; amyotrophic lateral sclerosis (ALS); a motor neuron disease; epilepsy; macular degeneration; metabolic syndrome; brain cancer; Huntington's Disease; a mood disorder; schizophrenia; bipolar disorder; a pervasive developmental disorder; autistic disorder; Asperger's syndrome,; childhood disintegrative disorder (CDD); Rett's disorder; PDD-not otherwise specified (PDD-NOS); a cerebrovascular accident; stroke; a vision impairment; optic neuropathy; dominant inherited juvenile optic atrophy; optic neuropathy caused by a toxic agent; glaucoma; Stargardt's macular dystrophy; diabetic retinopathy; diabetic maculopathy; retinopathy of prematurity; ischemic reperfusion-related retinal injury; oxygen poisoning; a haemoglobinopathy; thalassemia; sickle cell anemia; seizures; ischemia; renal tubular acidosis; attention deficit/hyperactivity disorder (ADHD); a neurodegenerative disorder resulting in hearing or balance impairment; Dominant Optic Atrophy (DOA); Maternally inherited diabetes and deafness (MIDD); chronic fatigue; contrast-induced kidney damage; contrast-induced retinopathy damage; Abetalipoproteinemia; retinitis pigmentosum; Wolfram's disease; Tourette syndrome; cobalamin c defect; methylmalonic aciduria; glioblastoma; Down's syndrome; acute tubular necrosis; a muscular dystrophy; a leukodystrophy; Progressive Supranuclear Palsy; spinal muscle atrophy; hearing loss; noise induced hearing loss; and traumatic brain injury; comprising administering to a subject in need thereof a therapeutically effective amount of a compound of formula (I):

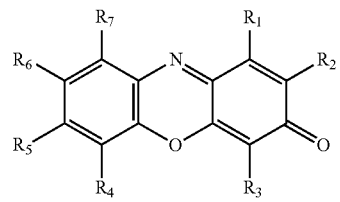

wherein:

$R_1$ and $R_2$ are independently selected from the group consisting of: —$C_1$-$C_4$ alkyl, —O—$C_1$-$C_4$ alkyl, and —$C_1$-$C_4$ haloalkyl, and $R_3$ is selected from the group consisting of: —$C_1$-$C_{12}$ alkyl, —O—$C_1$-$C_{12}$ alkyl, and —$C_1$-$C_{12}$ haloalkyl; or $R_1$ and $R_2$ are both —$CH_3$ or $R_1$ and $R_2$ are both —$OCH_3$ and $R_3$ is selected from the group consisting of:

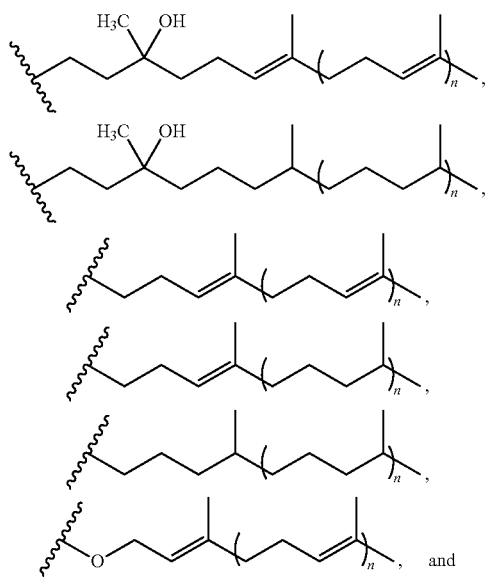

-continued

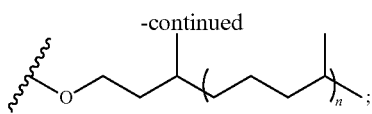

n is 0, 1, 2, 3, or 4;

$R_4$, $R_5$, $R_6$, and $R_7$ are independently selected from the group consisting of: —H, —$C_1$-$C_{12}$ alkyl, —$C_2$-$C_{12}$ alkenyl, —$C_1$-$C_{12}$ haloalkyl, —O—$C_1$-$C_{12}$ alkyl, —O—$C_1$-$C_{12}$ haloalkyl, —$C_6$-$C_{10}$ aryl, —O—$C_6$-$C_{10}$ aryl, —$C_1$-$C_6$ alkyl-$C_6$-$C_{10}$ aryl, —O—$C_1$-$C_6$ alkyl-$C_6$-$C_{10}$ aryl, —N—($R_8$)($R_9$),

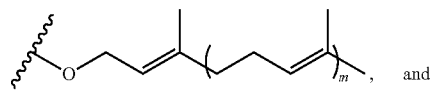, and

-continued

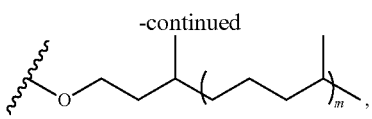

with the proviso that at least two of $R_4$, $R_5$, $R_6$, and $R_7$ are independently selected from the group consisting of: —H and —$CH_3$;

$R_8$ and $R_9$ are independently —H or —$C_1$-$C_{12}$ alkyl; and m is 0, 1, 2, or 3;

or a stereoisomer, mixture of stereoisomers, solvate, hydrate, or pharmaceutically acceptable salt thereof.

17. The method of claim 16, wherein $R_1$, $R_2$, and $R_3$ are —$CH_3$.

18. The method of claim 16, wherein $R_1$ and $R_2$ are —$OCH_3$, and $R_3$ is —$CH_3$.

19. The method of claim 16, wherein three of $R_4$, $R_5$, $R_6$, and $R_7$ are —H.

* * * * *